US012241057B2

(12) United States Patent
Hudson et al.

(10) Patent No.: US 12,241,057 B2
(45) Date of Patent: *Mar. 4, 2025

(54) METHODS FOR NUCLEIC ACID ASSEMBLY AND HIGH THROUGHPUT SEQUENCING

(71) Applicant: Gen9, Inc., Boston, MA (US)

(72) Inventors: Michael E. Hudson, Boston, MA (US); Li-Yun A. Kung, Boston, MA (US); Daniel Schindler, Boston, MA (US); Stephen Archer, Boston, MA (US); Ishtiaq Saaem, Boston, MA (US)

(73) Assignee: Gen9, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/361,091

(22) Filed: Jun. 28, 2021

(65) Prior Publication Data

US 2021/0395724 A1 Dec. 23, 2021

Related U.S. Application Data

(63) Continuation of application No. 16/714,208, filed on Dec. 13, 2019, now Pat. No. 11,072,789, which is a continuation of application No. 14/408,103, filed as application No. PCT/US2013/047370 on Jun. 24, 2013, now abandoned.

(60) Provisional application No. 61/731,627, filed on Nov. 30, 2012, provisional application No. 61/664,118, filed on Jun. 25, 2012.

(51) Int. Cl.
| C12Q 1/686 | (2018.01) |
| C12N 15/10 | (2006.01) |
| C12N 15/66 | (2006.01) |

(52) U.S. Cl.
CPC ..... *C12N 15/1031* (2013.01); *C12N 15/1093* (2013.01); *C12N 15/66* (2013.01); *C12Q 1/686* (2013.01)

(58) Field of Classification Search
CPC ........ C12Q 2521/301; C12Q 2521/501; C12Q 1/686; C12N 15/1031; C12N 15/1093
See application file for complete search history.

(56) References Cited

U.S. PATENT DOCUMENTS

| 4,500,707 A | 2/1985 | Caruthers et al. |
| 4,683,195 A | 7/1987 | Mullis et al. |
| 4,683,202 A | 7/1987 | Mullis |
| 4,689,405 A | 8/1987 | Frank et al. |
| 4,725,677 A | 2/1988 | Koster et al. |
| 4,800,159 A | 1/1989 | Mullis et al. |
| 4,888,286 A | 12/1989 | Crea |
| 4,959,317 A | 9/1990 | Sauer |
| 4,965,188 A | 10/1990 | Mullis et al. |
| 4,999,294 A | 3/1991 | Looney et al. |
| 5,047,524 A | 9/1991 | Andrus et al. |
| 5,093,251 A | 3/1992 | Richards et al. |
| 5,096,825 A | 3/1992 | Barr et al. |
| 5,104,789 A | 4/1992 | Permar et al. |
| 5,104,792 A | 4/1992 | Silver et al. |
| 5,132,215 A | 7/1992 | Jayaraman et al. |
| 5,143,854 A | 9/1992 | Pirrung et al. |
| 5,288,514 A | 2/1994 | Ellman |
| 5,356,802 A | 10/1994 | Chandrasegaran |
| 5,384,261 A | 1/1995 | Winkler et al. |
| 5,395,750 A | 3/1995 | Dillon et al. |
| 5,405,783 A | 4/1995 | Pirrung et al. |
| 5,424,186 A | 6/1995 | Fodor et al. |
| 5,436,150 A | 7/1995 | Chandrasegaran |
| 5,436,327 A | 7/1995 | Southern et al. |
| 5,445,934 A | 8/1995 | Fodor et al. |
| 5,459,039 A | 10/1995 | Modrich et al. |
| 5,474,796 A | 12/1995 | Brennan |
| 5,498,531 A | 3/1996 | Jarrell |
| 5,508,169 A | 4/1996 | Deugau et al. |

(Continued)

FOREIGN PATENT DOCUMENTS

| CN | 1145641 A | 3/1997 |
| CN | 1468313 A | 1/2004 |

(Continued)

OTHER PUBLICATIONS

Notice of Opposition mailed Jul. 23, 2019, for Application No. EP 2864531. 86 pages.
Proprietor's response and amended claims filed Sep. 19, 2016 for Application No. EP 13809969.2 in reply to the communication under Rules 70(2) and 70a (2) EPC. Exhibit D19 in Opposition. 7 pages.
Proprietor's response and amended claims filed Feb. 7, 2018 for Application No. EP 13809969.2 in reply to the communication under Art 94(3) EPC dated Jul. 31, 2017. Exhibit D20 in Opposition. 9 pages.
Proprietor's letter and amended claims filed Mar. 23, 2018 for Application No. EP 13809969.2. Exhibit D21 in Opposition. 7 pages.

(Continued)

*Primary Examiner* — Young J Kim
(74) *Attorney, Agent, or Firm* — Wolf, Greenfield & Sacks, P.C.

(57) ABSTRACT

Methods and apparatus of some aspects of the invention relate to the synthesis of high fidelity polynucleotides. In particular, aspects of the invention relate to concurrent enzymatic removal of amplification sequences and ligation of processed oligonucleotides into nucleic acid assemblies. According to some embodiments, the invention provides a method for producing a target nucleic acid having a predefined sequence. In some embodiments, the method comprises the step of providing a plurality of oligonucleotides, wherein each oligonucleotides comprises (i) an internal sequence identical to a different portion of a sequence of a target nucleic acid, (ii) a 5' sequence flanking the 5' end of the internal sequence and a 3' flanking sequence flanking the 3' end of the internal sequence, each of the flanking sequence comprising a primer recognition site for a primer pair and a restriction enzyme recognition site.

26 Claims, 6 Drawing Sheets

Specification includes a Sequence Listing.

(56) References Cited

U.S. PATENT DOCUMENTS

| | | |
|---|---|---|
| 5,510,270 A | 4/1996 | Fodor et al. |
| 5,512,463 A | 4/1996 | Stemmer |
| 5,514,789 A | 5/1996 | Kempe |
| 5,527,681 A | 6/1996 | Holmes |
| 5,541,061 A | 7/1996 | Fodor et al. |
| 5,556,750 A | 9/1996 | Modrich et al. |
| 5,604,097 A | 2/1997 | Brenner |
| 5,605,793 A | 2/1997 | Stemmer |
| 5,624,711 A | 4/1997 | Sundberg et al. |
| 5,639,603 A | 6/1997 | Dower et al. |
| 5,641,658 A | 6/1997 | Adams et al. |
| 5,653,939 A | 8/1997 | Hollis et al. |
| 5,674,742 A | 10/1997 | Northrup et al. |
| 5,679,522 A | 10/1997 | Modrich et al. |
| 5,695,940 A | 12/1997 | Drmanac et al. |
| 5,700,637 A | 12/1997 | Southern |
| 5,700,642 A | 12/1997 | Monforte et al. |
| 5,702,894 A | 12/1997 | Modrich et al. |
| 5,738,829 A | 4/1998 | Kempe |
| 5,739,386 A | 4/1998 | Holmes |
| 5,750,335 A | 5/1998 | Gifford |
| 5,766,550 A | 6/1998 | Kaplan et al. |
| 5,770,358 A | 6/1998 | Dower et al. |
| 5,780,272 A | 7/1998 | Jarrell |
| 5,795,714 A | 8/1998 | Cantor et al. |
| 5,830,655 A | 11/1998 | Monforte et al. |
| 5,830,721 A | 11/1998 | Stemmer et al. |
| 5,834,252 A | 11/1998 | Stemmer et al. |
| 5,858,754 A | 1/1999 | Modrich et al. |
| 5,861,482 A | 1/1999 | Modrich et al. |
| 5,871,902 A | 2/1999 | Weininger et al. |
| 5,877,280 A | 3/1999 | Wetmur |
| 5,912,129 A | 6/1999 | Vinayagamoorthy et al. |
| 5,916,794 A | 6/1999 | Chandrasegaran |
| 5,922,539 A | 7/1999 | Modrich et al. |
| 5,928,905 A | 7/1999 | Stemmer et al. |
| 5,929,208 A | 7/1999 | Heller et al. |
| 5,942,609 A | 8/1999 | Hunkapiller et al. |
| 5,953,469 A | 9/1999 | Zhou |
| 6,008,031 A | 12/1999 | Modrich et al. |
| 6,013,440 A | 1/2000 | Lipshutz et al. |
| 6,017,696 A | 1/2000 | Heller |
| 6,027,877 A | 2/2000 | Wagner, Jr. |
| 6,042,211 A | 3/2000 | Hudson et al. |
| 6,093,302 A | 7/2000 | Montgomery |
| 6,103,463 A | 8/2000 | Chetverin et al. |
| 6,110,668 A | 8/2000 | Strizhov et al. |
| 6,136,568 A | 10/2000 | Hiatt et al. |
| 6,143,527 A | 11/2000 | Pachuk et al. |
| 6,150,102 A | 11/2000 | Mills, Jr. et al. |
| 6,150,141 A | 11/2000 | Jarrell |
| 6,165,793 A | 12/2000 | Stemmer |
| 6,177,558 B1 | 1/2001 | Brennan et al. |
| 6,242,211 B1 | 6/2001 | Peterson et al. |
| 6,248,521 B1 | 6/2001 | Van Ness et al. |
| 6,261,797 B1 | 7/2001 | Sorge et al. |
| 6,271,957 B1 | 8/2001 | Quate et al. |
| 6,277,632 B1 | 8/2001 | Harney |
| 6,280,595 B1 | 8/2001 | Montgomery |
| 6,284,463 B1 | 9/2001 | Hasebe et al. |
| 6,287,825 B1 | 9/2001 | Weissman et al. |
| 6,287,861 B1 | 9/2001 | Stemmer et al. |
| 6,291,242 B1 | 9/2001 | Stemmer |
| 6,315,958 B1 | 11/2001 | Singh-Gasson et al. |
| 6,322,971 B1 | 11/2001 | Chetverin et al. |
| 6,326,489 B1 | 12/2001 | Church et al. |
| 6,333,153 B1 | 12/2001 | Fishel et al. |
| 6,346,399 B1 | 2/2002 | Weissman et al. |
| 6,355,412 B1 | 3/2002 | Stewart et al. |
| 6,355,423 B1 | 3/2002 | Rothberg et al. |
| 6,358,712 B1 | 3/2002 | Jarrell et al. |
| 6,365,355 B1 | 4/2002 | McCutchen-Maloney |
| 6,372,429 B1 | 4/2002 | Sharon |
| 6,372,434 B1 | 4/2002 | Weissman |
| 6,372,484 B1 | 4/2002 | Ronchi et al. |
| 6,375,903 B1 | 4/2002 | Cerrina et al. |
| 6,376,246 B1 | 4/2002 | Crameri et al. |
| 6,406,847 B1 | 6/2002 | Cox et al. |
| 6,410,220 B1 * | 6/2002 | Hodgson ............... C12N 15/66 435/5 |
| 6,416,164 B1 | 7/2002 | Stearns et al. |
| 6,426,184 B1 | 7/2002 | Gao et al. |
| 6,432,360 B1 | 8/2002 | Church |
| 6,444,111 B1 | 9/2002 | Montgomery |
| 6,444,175 B1 | 9/2002 | Singh-Gasson et al. |
| 6,444,650 B1 | 9/2002 | Cech et al. |
| 6,444,661 B1 | 9/2002 | Barton et al. |
| 6,472,184 B1 | 10/2002 | Hegemann et al. |
| 6,479,652 B1 | 11/2002 | Crameri et al. |
| 6,480,324 B2 | 11/2002 | Quate et al. |
| 6,489,146 B2 | 12/2002 | Stemmer |
| 6,495,318 B2 | 12/2002 | Harney |
| 6,506,603 B1 | 1/2003 | Stemmer |
| 6,509,156 B1 | 1/2003 | Stewart |
| 6,511,849 B1 | 1/2003 | Wang |
| 6,514,704 B2 | 2/2003 | Bruce et al. |
| 6,521,427 B1 | 2/2003 | Evans |
| 6,534,271 B2 | 3/2003 | Furste |
| 6,537,776 B1 | 3/2003 | Short |
| 6,565,727 B1 | 5/2003 | Shenderov |
| 6,586,211 B1 | 7/2003 | Stahler et al. |
| 6,593,111 B2 | 7/2003 | Baric et al. |
| 6,596,239 B2 | 7/2003 | Williams et al. |
| 6,605,451 B1 | 8/2003 | Marmaro et al. |
| 6,610,499 B1 | 8/2003 | Fulwyler et al. |
| 6,613,581 B1 | 9/2003 | Wada et al. |
| 6,632,641 B1 | 10/2003 | Brennan |
| 6,650,822 B1 | 11/2003 | Zhou |
| 6,658,802 B2 | 12/2003 | Lucas, Jr. et al. |
| 6,660,475 B2 | 12/2003 | Jack et al. |
| 6,664,112 B2 | 12/2003 | Mulligan et al. |
| 6,664,388 B2 | 12/2003 | Nelson |
| 6,670,127 B2 | 12/2003 | Evans |
| 6,670,605 B1 | 12/2003 | Storm, Jr. et al. |
| 6,800,439 B1 | 10/2004 | McGall et al. |
| 6,802,593 B2 | 10/2004 | Ellson et al. |
| 6,824,866 B1 | 11/2004 | Glazer et al. |
| 6,830,890 B2 | 12/2004 | Lockhart et al. |
| 6,833,450 B1 | 12/2004 | McGall et al. |
| 6,846,655 B1 | 1/2005 | Wagner et al. |
| 6,897,025 B2 | 5/2005 | Cox et al. |
| 6,911,132 B2 | 6/2005 | Pamula et al. |
| 6,921,818 B2 | 7/2005 | Sproat |
| 6,932,097 B2 | 8/2005 | Ellson et al. |
| 6,946,296 B2 | 9/2005 | Patten et al. |
| 6,955,901 B2 | 10/2005 | Schouten |
| 6,969,587 B2 | 11/2005 | Taylor |
| 6,969,847 B2 | 11/2005 | Davis et al. |
| 7,090,333 B2 | 8/2006 | Mutz et al. |
| 7,133,782 B2 | 11/2006 | Odedra |
| 7,144,734 B2 | 12/2006 | Court et al. |
| 7,169,560 B2 | 1/2007 | Lapidus et al. |
| 7,179,423 B2 | 2/2007 | Bohm et al. |
| 7,183,406 B2 | 2/2007 | Belshaw |
| 7,199,233 B1 | 4/2007 | Jensen et al. |
| 7,262,031 B2 | 8/2007 | Lathrop |
| 7,273,730 B2 | 9/2007 | Du Breuil Lastrucci |
| 7,285,835 B2 | 10/2007 | Rizzo et al. |
| 7,303,320 B1 | 12/2007 | Ashley |
| 7,303,872 B2 | 12/2007 | Sussman |
| 7,323,320 B2 | 1/2008 | Oleinikov |
| 7,399,590 B2 | 7/2008 | Piepenburg et al. |
| 7,432,055 B2 | 10/2008 | Pemov et al. |
| 7,498,176 B2 | 3/2009 | McCormick et al. |
| 7,537,897 B2 | 5/2009 | Brenner et al. |
| 7,563,600 B2 | 7/2009 | Oleinikov |
| 7,699,979 B2 | 4/2010 | Li et al. |
| 7,723,077 B2 | 5/2010 | Young et al. |
| 7,820,412 B2 | 10/2010 | Belshaw et al. |
| 7,879,580 B2 | 2/2011 | Carr et al. |
| 7,932,025 B2 | 4/2011 | Carr et al. |
| 8,053,191 B2 | 11/2011 | Blake |
| 8,058,004 B2 | 11/2011 | Oleinikov |
| 8,137,906 B2 | 3/2012 | Schatz |

(56) References Cited

U.S. PATENT DOCUMENTS

| | | |
|---|---|---|
| 8,173,368 B2 | 5/2012 | Staehler et al. |
| 8,338,091 B2 | 12/2012 | Chesnut et al. |
| 8,476,018 B2 | 7/2013 | Brenner |
| 8,716,467 B2 | 5/2014 | Jacobson |
| 8,808,986 B2 | 8/2014 | Jacobson et al. |
| 9,023,601 B2 | 5/2015 | Oleinikov |
| 9,023,649 B2 | 5/2015 | Mali et al. |
| 9,051,666 B2 | 6/2015 | Oleinikov |
| 9,150,853 B2 | 10/2015 | Hudson et al. |
| 9,295,965 B2 | 3/2016 | Jacobson et al. |
| 9,322,037 B2 | 4/2016 | Liu et al. |
| 9,752,176 B2 | 9/2017 | Kung et al. |
| 11,072,789 B2 * | 7/2021 | Hudson ............... C12N 15/1031 |
| 2001/0012537 A1 | 8/2001 | Anderson et al. |
| 2001/0031483 A1 | 10/2001 | Sorge et al. |
| 2001/0049125 A1 | 12/2001 | Stemmer et al. |
| 2001/0053519 A1 | 12/2001 | Fodor et al. |
| 2002/0012616 A1 | 1/2002 | Zhou et al. |
| 2002/0025561 A1 | 2/2002 | Hodgson |
| 2002/0037579 A1 | 3/2002 | Ellson et al. |
| 2002/0058275 A1 | 5/2002 | Fishel et al. |
| 2002/0081582 A1 | 6/2002 | Gao et al. |
| 2002/0127552 A1 | 9/2002 | Church et al. |
| 2002/0132259 A1 | 9/2002 | Wagner et al. |
| 2002/0132308 A1 | 9/2002 | Liu et al. |
| 2002/0133359 A1 | 9/2002 | Brown |
| 2003/0017552 A1 | 1/2003 | Jarrell et al. |
| 2003/0044980 A1 | 3/2003 | Mancebo et al. |
| 2003/0047688 A1 | 3/2003 | Faris et al. |
| 2003/0050437 A1 | 3/2003 | Montgomery |
| 2003/0050438 A1 | 3/2003 | Montgomery |
| 2003/0054390 A1 | 3/2003 | Crameri et al. |
| 2003/0068633 A1 | 4/2003 | Belshaw et al. |
| 2003/0068643 A1 | 4/2003 | Brennan et al. |
| 2003/0082630 A1 | 5/2003 | Kolkman et al. |
| 2003/0087298 A1 | 5/2003 | Green et al. |
| 2003/0091476 A1 | 5/2003 | Zhou et al. |
| 2003/0099952 A1 | 5/2003 | Green et al. |
| 2003/0118485 A1 | 6/2003 | Singh-Gasson et al. |
| 2003/0118486 A1 | 6/2003 | Zhou et al. |
| 2003/0120035 A1 | 6/2003 | Gao et al. |
| 2003/0134807 A1 | 7/2003 | Hardin et al. |
| 2003/0143550 A1 | 7/2003 | Green et al. |
| 2003/0143724 A1 | 7/2003 | Cerrina et al. |
| 2003/0165841 A1 | 9/2003 | Burgin et al. |
| 2003/0170616 A1 | 9/2003 | Wang et al. |
| 2003/0171325 A1 | 9/2003 | Gascoyne et al. |
| 2003/0175907 A1 | 9/2003 | Frazer et al. |
| 2003/0186226 A1 | 10/2003 | Brennan et al. |
| 2003/0198948 A1 | 10/2003 | Stahler et al. |
| 2003/0215837 A1 | 11/2003 | Frey et al. |
| 2003/0215855 A1 | 11/2003 | Dubrow et al. |
| 2003/0215856 A1 | 11/2003 | Church et al. |
| 2003/0219781 A1 | 11/2003 | Frey |
| 2003/0224521 A1 | 12/2003 | Court et al. |
| 2004/0002103 A1 | 1/2004 | Short |
| 2004/0005673 A1 | 1/2004 | Jarrell et al. |
| 2004/0009479 A1 | 1/2004 | Wohlgemuth et al. |
| 2004/0009520 A1 | 1/2004 | Albert et al. |
| 2004/0014083 A1 | 1/2004 | Yuan et al. |
| 2004/0053362 A1 | 3/2004 | De luca et al. |
| 2004/0096891 A1 | 5/2004 | Bennett |
| 2004/0101444 A1 | 5/2004 | Sommers et al. |
| 2004/0101894 A1 | 5/2004 | Albert et al. |
| 2004/0101949 A1 | 5/2004 | Green et al. |
| 2004/0106728 A1 | 6/2004 | McGall et al. |
| 2004/0110211 A1 | 6/2004 | McCormick et al. |
| 2004/0110212 A1 | 6/2004 | McCormick et al. |
| 2004/0126757 A1 | 7/2004 | Cerrina |
| 2004/0132029 A1 | 7/2004 | Sussman et al. |
| 2004/0166567 A1 | 8/2004 | Santi et al. |
| 2004/0171047 A1 | 9/2004 | Dahl et al. |
| 2004/0185484 A1 | 9/2004 | Costa et al. |
| 2004/0229359 A1 | 11/2004 | Mead et al. |
| 2004/0241655 A1 | 12/2004 | Hwang et al. |
| 2004/0259146 A1 | 12/2004 | Friend et al. |
| 2005/0053997 A1 | 3/2005 | Evans |
| 2005/0069928 A1 | 3/2005 | Nelson et al. |
| 2005/0079510 A1 | 4/2005 | Berka et al. |
| 2005/0089889 A1 | 4/2005 | Ramsing et al. |
| 2005/0106606 A1 | 5/2005 | Parker et al. |
| 2005/0118628 A1 | 6/2005 | Evans |
| 2005/0202429 A1 | 9/2005 | Trau et al. |
| 2005/0208503 A1 | 9/2005 | Yowanto et al. |
| 2005/0221340 A1 | 10/2005 | Evans |
| 2005/0227235 A1 | 10/2005 | Carr et al. |
| 2005/0227316 A1 | 10/2005 | Santi et al. |
| 2005/0255477 A1 | 11/2005 | Carr et al. |
| 2005/0287585 A1 | 12/2005 | Oleinikov |
| 2006/0003347 A1 | 1/2006 | Griffiths et al. |
| 2006/0008833 A1 | 1/2006 | Jacobson |
| 2006/0014146 A1 | 1/2006 | Sucaille et al. |
| 2006/0035218 A1 | 2/2006 | Oleinikov |
| 2006/0040297 A1 | 2/2006 | Leamon et al. |
| 2006/0054503 A1 | 3/2006 | Pamula et al. |
| 2006/0127920 A1 | 6/2006 | Church et al. |
| 2006/0127926 A1 | 6/2006 | Belshaw et al. |
| 2006/0134638 A1 | 6/2006 | Mulligan et al. |
| 2006/0160138 A1 | 7/2006 | Church et al. |
| 2006/0194214 A1 | 8/2006 | Church et al. |
| 2006/0281113 A1 | 12/2006 | Church et al. |
| 2007/0004041 A1 | 1/2007 | Church et al. |
| 2007/0009928 A1* | 1/2007 | Lathrop ............ C12N 15/1093 702/20 |
| 2007/0122817 A1 | 5/2007 | Church et al. |
| 2007/0231805 A1 | 10/2007 | Baynes et al. |
| 2007/0269870 A1 | 11/2007 | Church et al. |
| 2007/0281309 A1 | 12/2007 | Kong et al. |
| 2008/0003571 A1 | 1/2008 | McKernan et al. |
| 2008/0009420 A1 | 1/2008 | Schroth et al. |
| 2008/0044862 A1 | 2/2008 | Schatz et al. |
| 2008/0064610 A1 | 3/2008 | Lipovsek et al. |
| 2008/0105829 A1 | 5/2008 | Faris et al. |
| 2008/0214408 A1 | 9/2008 | Chatterjee et al. |
| 2008/0261300 A1 | 10/2008 | Santi et al. |
| 2008/0274510 A1 | 11/2008 | Santi et al. |
| 2008/0274513 A1 | 11/2008 | Shenderov et al. |
| 2008/0287320 A1 | 11/2008 | Baynes et al. |
| 2008/0300842 A1 | 12/2008 | Govindarajan et al. |
| 2009/0016932 A1 | 1/2009 | Curcio et al. |
| 2009/0036323 A1 | 2/2009 | van Eijk et al. |
| 2009/0087840 A1 | 4/2009 | Baynes et al. |
| 2009/0093378 A1 | 4/2009 | Bignell et al. |
| 2009/0137408 A1 | 5/2009 | Jacobson |
| 2009/0155858 A1 | 6/2009 | Blake |
| 2009/0280497 A1 | 11/2009 | Woudenberg et al. |
| 2009/0280697 A1 | 11/2009 | Li et al. |
| 2009/0305233 A1 | 12/2009 | Borovkov et al. |
| 2010/0015614 A1 | 1/2010 | Beer et al. |
| 2010/0015668 A1 | 1/2010 | Staehler et al. |
| 2010/0016178 A1 | 1/2010 | Sussman et al. |
| 2010/0028873 A1 | 2/2010 | Belouchi et al. |
| 2010/0028885 A1 | 2/2010 | Balasubramanian et al. |
| 2010/0124764 A1 | 5/2010 | Hufton et al. |
| 2010/0124767 A1* | 5/2010 | Oleinikov ............ B82Y 30/00 435/91.5 |
| 2010/0273219 A1 | 10/2010 | May et al. |
| 2010/0311058 A1 | 12/2010 | Kim et al. |
| 2011/0117625 A1 | 5/2011 | Lippow et al. |
| 2011/0124049 A1* | 5/2011 | Li ..................... C12N 15/1031 435/91.2 |
| 2011/0160078 A1 | 6/2011 | Fodor et al. |
| 2011/0172127 A1 | 7/2011 | Jacobson et al. |
| 2011/0217738 A1 | 9/2011 | Jacobson |
| 2011/0244521 A1 | 10/2011 | Nagai et al. |
| 2011/0283110 A1 | 11/2011 | Dapkus et al. |
| 2011/0287490 A1 | 11/2011 | Coope et al. |
| 2012/0028843 A1 | 2/2012 | Ramu et al. |
| 2012/0115756 A1 | 5/2012 | Williams et al. |
| 2012/0185965 A1 | 7/2012 | Senger et al. |
| 2012/0220497 A1 | 8/2012 | Jacobson et al. |
| 2012/0270750 A1 | 10/2012 | Oleinikov |
| 2012/0270754 A1 | 10/2012 | Blake |
| 2012/0283110 A1 | 11/2012 | Shendure et al. |

(56) References Cited

U.S. PATENT DOCUMENTS

| | | |
|---|---|---|
| 2012/0283140 A1 | 11/2012 | Chu |
| 2012/0315670 A1 | 12/2012 | Jacobson et al. |
| 2012/0322681 A1 | 12/2012 | Kung et al. |
| 2013/0005582 A1 | 1/2013 | Lower |
| 2013/0017977 A1 | 1/2013 | Oleinikov |
| 2013/0059296 A1 | 3/2013 | Jacobson et al. |
| 2013/0059344 A1 | 3/2013 | Striedner et al. |
| 2013/0059761 A1 | 3/2013 | Jacobson et al. |
| 2013/0085083 A1 | 4/2013 | Kamberov et al. |
| 2013/0130347 A1 | 5/2013 | Delisa et al. |
| 2013/0163263 A1 | 6/2013 | Jacobson et al. |
| 2013/0196373 A1 | 8/2013 | Gregory et al. |
| 2013/0224729 A1 | 8/2013 | Church et al. |
| 2013/0225421 A1 | 8/2013 | Li et al. |
| 2013/0244884 A1 | 9/2013 | Jacobson et al. |
| 2013/0252849 A1 | 9/2013 | Hudson et al. |
| 2013/0274135 A1 | 10/2013 | Zhang et al. |
| 2013/0281308 A1 | 10/2013 | Kung et al. |
| 2013/0296192 A1 | 11/2013 | Jacobson |
| 2013/0296194 A1 | 11/2013 | Jacobson |
| 2013/0309725 A1 | 11/2013 | Jacobson |
| 2014/0141982 A1 | 5/2014 | Jacobson et al. |
| 2014/0295556 A1 | 10/2014 | Joung et al. |
| 2014/0309119 A1 | 10/2014 | Jacobson et al. |
| 2015/0031089 A1 | 1/2015 | Lindstrom |
| 2015/0065393 A1 | 3/2015 | Jacobson |
| 2015/0203839 A1 | 7/2015 | Jacobson et al. |
| 2015/0315547 A1 | 11/2015 | Oberg |
| 2015/0361420 A1 | 12/2015 | Hudson et al. |
| 2015/0368687 A1 | 12/2015 | Saaem et al. |
| 2015/0376602 A1 | 12/2015 | Jacobson et al. |
| 2016/0001247 A1 | 1/2016 | Oleinikov |
| 2016/0097051 A1 | 4/2016 | Jacobson et al. |
| 2016/0122755 A1 | 5/2016 | Hall et al. |
| 2016/0144332 A1 | 5/2016 | Chu |
| 2016/0144333 A1 | 5/2016 | Jacobson et al. |
| 2016/0168564 A1 | 6/2016 | Jacobson et al. |
| 2016/0215381 A1 | 7/2016 | Levine et al. |
| 2016/0250613 A1 | 9/2016 | Jacobson et al. |
| 2016/0326520 A1 | 11/2016 | Ramu et al. |
| 2017/0137858 A1 | 5/2017 | Carr et al. |
| 2017/0175110 A1 | 6/2017 | Jacobson et al. |
| 2017/0198268 A1 | 7/2017 | Jacobson et al. |
| 2017/0349925 A1 | 12/2017 | Jacobson et al. |
| 2018/0023120 A1 | 1/2018 | Kung et al. |
| 2018/0355353 A1 | 12/2018 | Saaem |
| 2019/0010530 A1 | 1/2019 | Saaem |
| 2019/0100751 A1 | 4/2019 | Jacobson et al. |

FOREIGN PATENT DOCUMENTS

| | | |
|---|---|---|
| CN | 101921840 A | 12/2010 |
| DE | 4343591 A1 | 6/1995 |
| EP | 259160 | 3/1988 |
| EP | 1015576 A1 | 7/2000 |
| EP | 1159285 A1 | 12/2001 |
| EP | 1180548 A2 | 2/2002 |
| EP | 1314783 A1 | 5/2003 |
| EP | 1411122 A1 | 4/2004 |
| EP | 2017356 A2 | 1/2009 |
| EP | 2175021 A2 | 4/2010 |
| JP | 2005-538725 A | 12/2005 |
| JP | 2007-533308 A | 11/2007 |
| KR | 100491810 B1 | 10/2005 |
| WO | WO 1990/000626 A1 | 1/1990 |
| WO | WO 1992/015694 A1 | 9/1992 |
| WO | WO 1993/017126 A1 | 9/1993 |
| WO | WO 1993/020092 A1 | 10/1993 |
| WO | WO 1994/018226 A1 | 8/1994 |
| WO | WO 1995/017413 A1 | 6/1995 |
| WO | WO 1996/033207 A1 | 10/1996 |
| WO | WO 1996/034112 A1 | 10/1996 |
| WO | WO 1997/035957 A1 | 10/1997 |
| WO | WO 1998/005765 A1 | 2/1998 |
| WO | WO 1998/020020 A2 | 5/1998 |
| WO | WO 1998/038299 A1 | 9/1998 |
| WO | WO 1998/038326 A1 | 9/1998 |
| WO | WO 1999/014318 A1 | 3/1999 |
| WO | WO 1999/019341 A1 | 4/1999 |
| WO | WO 1999/025724 A2 | 5/1999 |
| WO | WO 1999/042813 A1 | 8/1999 |
| WO | WO 1999/047536 A2 | 9/1999 |
| WO | WO 2000/029616 A1 | 5/2000 |
| WO | WO 2000/040715 A2 | 7/2000 |
| WO | WO 2000/046386 A2 | 8/2000 |
| WO | WO 2000/049142 A1 | 8/2000 |
| WO | WO 2000/053617 A1 | 9/2000 |
| WO | WO 2000/075368 A2 | 12/2000 |
| WO | WO 2001/081568 A1 | 11/2001 |
| WO | WO 2001/085075 A1 | 11/2001 |
| WO | WO 2001/088173 A2 | 11/2001 |
| WO | WO 2002/004597 A2 | 1/2002 |
| WO | WO 2002/024597 A2 | 3/2002 |
| WO | WO 2002/081490 A2 | 10/2002 |
| WO | WO 2002/095073 A1 | 11/2002 |
| WO | WO 2002/101004 A2 | 12/2002 |
| WO | WO 2003/010311 A2 | 2/2003 |
| WO | WO 2003/033718 A1 | 4/2003 |
| WO | WO 2003/040410 A1 | 5/2003 |
| WO | WO 2003/044193 A2 | 5/2003 |
| WO | WO 2003/046223 A1 | 6/2003 |
| WO | WO 2003/054232 A2 | 7/2003 |
| WO | WO 2003/060084 A2 | 7/2003 |
| WO | WO 2003/064026 A1 | 8/2003 |
| WO | WO 2003/064027 A2 | 8/2003 |
| WO | WO 2003/064611 A2 | 8/2003 |
| WO | WO 2003/064699 A2 | 8/2003 |
| WO | WO 2003/065038 A2 | 8/2003 |
| WO | WO 2003/066212 A2 | 8/2003 |
| WO | WO 2003/083604 A2 | 10/2003 |
| WO | WO 2003/085094 A2 | 10/2003 |
| WO | WO 2003/089605 A2 | 10/2003 |
| WO | WO 2003/100012 A2 | 12/2003 |
| WO | WO 2004/002627 A2 | 1/2004 |
| WO | WO 2004/024886 | 3/2004 |
| WO | WO 2004/029586 A1 | 4/2004 |
| WO | WO 2004/031351 A2 | 4/2004 |
| WO | WO 2004/031399 A2 | 4/2004 |
| WO | WO 2004/034028 A2 | 4/2004 |
| WO | WO 2004/090170 A1 | 10/2004 |
| WO | WO 2005/059096 A2 | 6/2005 |
| WO | WO 2005/071077 A1 | 8/2005 |
| WO | WO 2005/089110 A2 | 9/2005 |
| WO | WO 2005/103279 A2 | 11/2005 |
| WO | WO 2005/107939 A1 | 11/2005 |
| WO | WO 2005/123956 A2 | 12/2005 |
| WO | WO 2006/031745 A2 | 3/2006 |
| WO | WO 2006/044956 A1 | 4/2006 |
| WO | WO 2006/049843 A1 | 5/2006 |
| WO | WO 2006/076679 A1 | 7/2006 |
| WO | WO 2006/086209 A2 | 8/2006 |
| WO | WO 2006/127423 A2 | 11/2006 |
| WO | WO 2007/008951 A1 | 1/2007 |
| WO | WO 2007/009082 A1 | 1/2007 |
| WO | WO 2007/010252 A1 | 1/2007 |
| WO | WO 2007/075438 A2 | 7/2007 |
| WO | WO 2007/087347 A2 | 8/2007 |
| WO | WO 2007/113688 A2 | 10/2007 |
| WO | WO 2007/117396 A1 | 10/2007 |
| WO | WO 2007/120624 A2 | 10/2007 |
| WO | WO 2007/123742 A2 | 11/2007 |
| WO | WO 2007/136736 A2 | 11/2007 |
| WO | WO 2007/136833 A2 | 11/2007 |
| WO | WO 2007/136834 A2 | 11/2007 |
| WO | WO 2007/136835 A2 | 11/2007 |
| WO | WO 2007/136840 A2 | 11/2007 |
| WO | WO 2008/024319 A2 | 2/2008 |
| WO | WO 2008/027558 A2 | 3/2008 |
| WO | WO 2008/041002 A2 | 4/2008 |
| WO | WO 2008/045380 A2 | 4/2008 |
| WO | WO 2008/054543 A2 | 5/2008 |
| WO | WO 2008/076368 A2 | 6/2008 |
| WO | WO 2008/095927 A1 | 8/2008 |
| WO | WO 2008/109176 A2 | 9/2008 |

(56) References Cited

FOREIGN PATENT DOCUMENTS

| WO | WO 2008/130629 A2 | 10/2008 |
|---|---|---|
| WO | WO 2009/032167 A1 | 3/2009 |
| WO | WO 2010/025310 A2 | 3/2010 |
| WO | WO 2010/070295 A1 | 6/2010 |
| WO | WO 2010/115100 A1 | 10/2010 |
| WO | WO 2010/115154 A1 | 10/2010 |
| WO | WO 2011/056872 A2 | 5/2011 |
| WO | WO 2011/066185 A1 | 6/2011 |
| WO | WO 2011/066186 A1 | 6/2011 |
| WO | WO 2011/085075 A2 | 7/2011 |
| WO | WO 2011/143556 A1 | 11/2011 |
| WO | WO 2011/150168 A1 | 12/2011 |
| WO | WO 2011/154147 A1 | 12/2011 |
| WO | WO 2011/161413 A2 | 12/2011 |
| WO | WO 2012/064975 A1 | 5/2012 |
| WO | WO 2012/078312 A2 | 6/2012 |
| WO | WO 2012/084923 A1 | 6/2012 |
| WO | WO 2012/174337 A1 | 12/2012 |
| WO | WO 2013/032850 A2 | 3/2013 |
| WO | WO 2013/163263 A2 | 10/2013 |
| WO | WO 2014/004393 A1 | 1/2014 |
| WO | WO 2014/089290 A1 | 6/2014 |
| WO | WO 2014/093694 A1 | 6/2014 |
| WO | WO 2014/144288 A1 | 9/2014 |
| WO | WO 2014/151696 A1 | 9/2014 |
| WO | WO 2014/160004 A1 | 10/2014 |
| WO | WO 2014/160059 A1 | 10/2014 |
| WO | WO 2014/191518 A1 | 12/2014 |
| WO | WO 2015/017527 A2 | 2/2015 |
| WO | WO 2015/035162 A2 | 3/2015 |
| WO | WO 2015/081114 A2 | 6/2015 |

OTHER PUBLICATIONS

Extended European Search Report mailed Feb. 18, 2019 for Application No. EP 18194361.4.
International Preliminary Report on Patentability mailed Dec. 31, 2014, for Application No. PCT/US2013/047370.
Extended European Search Report mailed Feb. 22, 2016 for Application No. EP 13809969.2.
Written Opinion dated Nov. 20, 2013, for Application No. PCT/US2013/047370.
International Search Report mailed Nov. 20, 2013 for Application No. PCT/US2013/047370.
[No Author Listed], TnT® coupled reticulocyte lysate system, Technical Bulletin (Promega, Madison, Wis), 2013.
Abremski et al. Studies on the properties of P 1 site-specific recombination: evidence for topologically unlinked products following recombination. Cell 32:1301-1311 (1983).
Abremski K. et al. Bacteriophage Pl site-specific recombination. Purification and properties of the Cre recombinase protein (1984) J. Mol. Biol. 259: 1509-1514.
Adessi et al., Solid phase DNA amplification: characterisation of primer attachment and amplification mechanisms. Nucleic Acids Research, 28(20):E87, (Oct. 15, 2000).
Afshari et al. Application of Complementary DNA Microarray Technology to Carcinogen Identification, Toxicology, and Drug Safety. Cancer Research, 59, 4759-4760, Oct. 1, 1999.
Aihara, H., et al. A Conformational Switch Controls the DNA Cleavage Activity of a Integrase, Molecular Cell, 12: 187-198, (Jul. 2003).
Akhundova A.A. et al. RNA synthesis on immobilized DNA templates in vitro. Biochemistry—Moscow, 43(5):626-628 (1978).
Altschul et al., Iterated profile searches with PSI-BLAST—a tool for discovery in protein databases, Trends Biochem. Sci., 23:444-447, (1998).
Altschul, S., et al. Basic local alignment search tool. J Mol Biol., 215(3):403-10, (1990).
Andersen, J., et al. New Unstable Variants of Green Fluorescent Protein for Studies of Transient Gene Expression in Bacteria. Applied and Environmental Microbiology, 64(6):2240-2246 (Jun. 1998).

Ashkin, Applications of laser radiation pressure Science, 210(4474): 1081-1088, (Dec. 5, 1980).
Aslanzadeh, Brief Review: Preventing PCR Amplification Carry-over Contamination in a Clinical Laboratory. Annals of Clinical & Laboratory Science 34(4) :389 (2004).
Au et al. Gene Synthesis by a LCR-Based Approach: High Level Production of Leptin-L54 Using Synthetic Gene in *Escherichia coli*, Biochemical and Biophysical Research Communications, 248:200-203 (1998).
Babineau et al. The FLP Protein of the 2 micron Plasmid of Yeast (1985) J. Biol. Chem. 260: 12313-12319.
Bar et al., Dendrimer-modified silicon oxide surfaces as platforms for the deposition of gold and silver colloid monolayers: preparation method, characterization, and correlation between microstructure and optical properties, Langmuir, 12(5): 1172-1179, (Mar. 6, 1996).
Bartsevich, V., et al. Engineered Zinc Finger Proteins for Controlling Stem Cell Fate. Stem Cells, 21:632-637 (2003).
Bath et al., Many type IIs restriction endonucleases interact with two recognition sites before cleaving DNA. J Biol Chem. Feb. 8, 2002;277(6):4024-33. Epub Nov. 29, 2001.
Beer et al., On-chip, real time single-copy polymerase chain reaction in picoliter droplets, Analytical Chemistry, 79(22):8471-8475, (Nov. 15, 2007).
Beier M. et al., Analysis of DNA-microarray produced by inverse in situ oligonucleotide synthesis. J. Biotechnology, 94:15-22 (2002).
Bennett, Solexa Ltd., Pharmacogenomics, 5(4):433-8, (Jun. 2004).
Berlin, DNA splicing by directed ligation (SDL), Current Issues Molec. Biol. 1:21-30, 1999.
Bethell et al. From monolayers to nanostructured materials: an organic chemist's view of self-assembly, J. Electroanal. Chem., 409:137-143, (1996).
Binkowski et al. Correcting errors in synthetic DNA through consensus shuffling Nucl. Acids Res., vol. 33, No. 6, e55, 2005.
Blanchard, A., Synthetic DNA Arrays. Genetic Engineering, 20:111-123, Plenum Press, (1998).
Boal et al. Cleavage of oligodeoxyribonucleotides from controlled-pore glass supports and their rapid deprotection by gaseous amines, NAR, 24(15):3115-3117, (1996).
Boltner, D., et al., R391: A Conjugative Integrating Mosaic Comprised of Phage, Plasmid, and Transposon Elements. J. of Bacteriology, 184(18):5158-5169 (Sep. 2002).
Booth, P.M., et al. Assembly and cloning of coding sequences for neurotrophic factors directly from genomic DNA using polymerase chain reaction and uracil DNA glycosylase. Gene 146:303-308 (1994).
Braatsch et al., *Escherichia coli* strains with promoter libraries constructed by Red/ET recombination pave the way for transcriptional fine-tuning, Biotechniques. 45(3): 335-337 (2008).
Brown, Chappell, BioBricks to help reverse-engineer life. URL: http://eetimes.com/news/latest/showArticle.ihtml?articleiD=21700333 (Jun. 11, 2004).
Burge et al., Prediction of complete gene structures in human genomic DNA. J Mol Biol., 268(1):78-94, (1997).
Cai et al. Immunogenicity of Polyepitope Libraries Assembled by Epitope Shuffling: An Approach to the Development of Chimeric Gene Vaccination Against Malaria, Vaccine, 23:267-277, (2004).
Carr, P., et al. Protein-mediated error-correction for de novo DNA synthesis. Nucleic Acids Research, 32(20), e162 (9 pages), (2004).
Caruthers et al. CXV. Total synthesis of the structural gene for an alanine transfer RNA from yeast. Enzymic joining to form the total DNA duplex. J Mol Biol. Dec. 28, 1972;72(2):475-92.
Cassell et al., Mechanism of Inhibition of Site-specific Recombination by the Holliday Junction-trapping Peptide WKHYNY: Insights into Phage I integrase-mediated Strand Exchange. J. Mol. Biol., 327:413-429, (2003).
Chakrabarti et al., Novel Sulfoxides facilitate GC-rich template amplification., 2002, BioTechniques 32(4):866-873.
Chalmers, F.P., et al. Scaling Up the Ligase Chain Reaction-Based Approach to Gene Synthesis. BioTechniques 30:249-252 (2001).
Chan, L. et al. Refactoring bacteriophage T7, Molecular Systems Biol., doi: 10.1038/msb4100025, (Published online Sep. 13, 2005).
Chandrasegaran, S., et al. Chimeric Restriction Enzymes: What is Next? Biol. Chern., 380:841-848 (1999).

(56) References Cited

OTHER PUBLICATIONS

Chang, C., et al. Evolution of a cytokine using DNA family shuffling, NatureBiotechnology, 17: 793-797(1999).
Che, A. BioBricks++: Simplifying Assembly of Standard DNA Components, [Online] XP002412778, URL:http://austinche.name/docs/bbpp.pdf (Jun. 9, 2004).
Chen, H.B., et al. A new method for the synthesis of a structural gene, Nucleic Acids Research 18(4):871-878 (1990).
Cherepanov A Joining of short DNA oligonucleotides with base pair mismatches by T4 DNA ligase J Biochem. Jan. 2001;129(1):61-8.
Chetverin, A.B. et al., Sequencing of Pools of Nucleic Acids on Oligonucleotide Arrays, Biosystems, vol. 30, pp. 215-231, 1993.
Chevalier, B., et al. Design, Activity, and Structure of a Highly Specific Artificial Endonuclease, Molecular Cell, 10:895-905 (2002).
Chevalier, B., et al. Homing endonucleases: structural and functional insight into the catalysts of intron/intein mobility, Nucl. Acids Res., 29(18):3757-3774 (2001).
Cho et al. Creating, transporting, cutting and merging liquid droplets by electrowetting-based actuation for digital microfluidic circuits, J. of Microelectromechanical Systems, 12(1):70-80, (Feb. 2003).
Christians, F., et al. Directed evolution of thymidine kinase for AZT phosphorylation using DNA family shuffling, Nature Biotechnology, 17:259-264(1999).
Coco, W., et al. Growth Factor Engineering by Degenerate Homoduplex Gene Family Recombination, Nature Biotechnology, 20: 1246-1250, (Dec. 2002).
Colvin, V., et al. Semiconductor nanocrystals covalently bound to metal surfaces with self-assembled monolayers, J. Am. Chem. Soc., 114(13):5221-5230, 1992.
Crameri, A, et al. DNA shuffling of a family of genes from diverse species accelerates directed evolution, Nature, 391:288-291(1998).
Crameri, A, et al. Improved Green Fluorescent Protein by Molecular Evolution Using DNA Shuffling, Nature Biotechnology, vol. 14, Mar. 1996, pp. 315-319.
Crameri, A, et al. Molecular evolution of an arsenate detoxification pathway by DNA shuffling, Nature Biotechnology, 15:436-438 (1997).
Cui T. et al. Sepharose-supported DNA as template for RNA synthesis J. Biotechnology, 66: 225-228 (1998).
Dafhnis-Calas, F., et al. Iterative in vivo assembly of large and complex transgenes by combining the activities of <DC31 integrase and Cre recombinase, Nucleic Acids Research, 33(22):1-14 (2005).
Datsenko K.A. et al. One-step inactivation of chromosomal genes in *Escherichia coli* K-12 using PCR products PNAS (2000) 97: 6640-6645.
Dedkova, L. et al. Enhanced D-Amino Acid Incorporation into Protein by modified Ribosomes. J. Am. Chem. Soc., 125:6616-6617, (2003).
Demeler et al. Neural network optimization for E.coli promoter prediction. Nucl. Acids. Res. 19:1593-1599 (1991).
Dillon, P.J. et al., A Rapid Method for the Construction of Synthetic Genes Using the Polymerase Chain Reaction, Biotechniques, vol. 9, No. 3, pp. 298-300, 1990.
Doyon et al., Enhancing zinc-finger-nuclease activity with improved obligate heterodimeric architectures. Nat Methods. Jan. 2011;8(1):74-9. Doi: 10.1038/nmeth.1539. Epub Dec. 5, 2010.
Duggan et al., Expression Profiling Using cDNA Microarrays. Nat. Genet. S21:10-14 (1999).
Ellson, Picoliter: Enabling Precise Transfer of Nanoliter and Picoliter Volumes Drug Discovery Today 7(5 Suppl.):s32 (2002).
Elowitz et al., A synthetic oscillatory network of transcriptional regulators. Nature. 2000;403;335-338.
Engler et al., A one pot, one step, precision cloning method with high throughput capability. PLoS One. 2008;3(11):e3647. doi: 10.1371/journal.pone.0003647. Epub Nov. 5, 2008.
Engler, C. et al., Golden Gate Shuffling: A One-Pot DNA Shuffling Method Based on Type Ils Restriction Enzymes, PLoS One, Public Library of Science, US, vol. 4, No. 5, pp. e5553-1, May 19, 2009.

Evans, E. & Alani, E. Roles for Mismatch Repair Factors in Regulating Genetic Recombination, Molecular & Cellular Biology, 20(21):7839-7844 (Nov. 2000).
Ferretti, L. et al. Total synthesis of a gene for bovine rhodopsin, PNAS, 83:599-603 (Feb. 1986).
Ferrin, L.J., et al. Sequence-specific ligation of DNA using RecA protein, Proc. Natl. Acad. Sci. USA, 95: 2152-2157 (1998).
Fidalgo et al., Surface induced droplet fusion in microfluidic devices, Lab on Chip, 7(8)984-986, (2007).
Fisch, I. et al. A Strategy of Exon Shuffling For Making Large Peptide Repertoires Displayed on Filamentous Bacteriophage, Proceedings of the National Academy of Sciences of USA, 93:7761-7766, (Jul. 1996).
Flanagan et al. Analysis of inhibitors of the site-specific recombination reaction mediated by Tn3 resolvase (1989) J. Mol. Biol. 206: 295-304.
Fleck, O. & Nielsen O. DNA Repair, J. Cell Science, 117:515-517 (2004).
Fodor, S., et al., Light-directed, spatially addressable parallel chemical synthesis, Science, 251(4995):767-773, (Feb. 15, 1991).
Fujita K. and Silver J. Surprising liability of biotin-streptavidin bond during transcription of biotinylated DNA bound to paramagnetic streptavidin beads., BioTechniques, 14:608-617 (1993).
Fullwood et al., Next-generation DNA sequencing of paired-end tags (PET) for transcriptome and genome analyses. Genome Res. Apr. 2009;19(4):521-32. doi: 10.1101/gr.074906.107.
Gabsalilow et al., Site- and strand-specific nicking of DNA by fusion proteins derived from MutH and I-ScoI or TALE repeats. Nucleic Acids Res. Apr. 2013;41(7):e83. doi:10.1093/nar/gkt080. Epub Feb. 13, 2013.
Gao, X. et al. Thermodynamically balanced inside-out (TBIO) PCR-based gene synthesis: a novel method of primer design for high fidelity assembly of longer gene sequences. Nucleic Acids Research, 31(22):e143 (11 pages) (2003).
Gardner, T., et al. Construction of a genetic toggle switch in *Escherichia coli*, Nature, 403:339-342 (Jan. 2000).
Gasiunas et al., Cas9-crRNA ribonucleoprotein complex mediates specific DNA cleavage for adaptive immunity in bacteria. Proc Natl Acad Sci U S A. Sep. 25, 2012;109(39):E2579-86. Epub Sep. 4, 2012.
Gibbs, W. Synthetic Life, Scientific American, [Online] URL: http://www.sciam.com/orintversion.cfm?articleiD=0009FCA4, (Apr. 26, 2004).
Glasgow A.C. et al. DNA-binding properties of the Hin recombinase (1989) J. Biol. Chem. 264: 10072-10082.
Goler, J. BioJADE: A Design and Simulation Tool for Synthetic Biological Systems. MIT Computer Science and Artificial Intelligence Laboratory, AI Technical Report, [Online] URL:http://dspace.mit.edu/bitstream/1721.1/30475/2/MIT-CSAIL-TR-2004-036.pdf, (May 2004).
Grabar et al., Preparation and Characterization Monolayers, Anal. Chem., 67:735-743, (1995).
Greenberg et al., Cleavage of oligonucleotides from solid-phase support using o-nitrobenzyl photochemistry, J. of Org. Chem., 59(4):746-753, (Feb. 1994).
Griffith et al., Coordinating Multiple Droplets in Planar Array Digital Microfluidic Systems, The International Journal of Robotics Research, 24(11):933-949, (Nov. 2005).
Gronostajski et al., The FLP protein of the 2 micron plasmid of yeast (1985) J. Biol. Chem. 260: 12328-12335.
Guilinger et al., Fusion of catalytically inactive Cas9 to FokI nuclease improves the specificity of genome modification. Nat Biotechnol. Jun. 2014;32(6):577-582. doi:10.1038/nbt.2909. Epub Apr. 25, 2014.
Gulati et al. Opportunities for microfluidic technologies in synthetic biology. Journal of the Royal Society, vol. 6, Suppl. 4, pp. S493-S506, (2009).
Guntas, G., et al. A molecular switch created by in vitro recombination of nonhomologous genes, Chern. & Biol., 11: 1483-1487 (Nov. 2004).
Guntas, G., et al. Directed Evolution of Protein Switches and Their Application to the Creation of Ligand-Binding Proteins, Proc. Natl. Acad. Sci. USA, 102(32):11224-11229 (Aug. 9, 2005).

(56) References Cited

OTHER PUBLICATIONS

Gupta et al. Studies on Polynucleotides, LXXXVIII. Enzymatic Joining of Chemically Synthesized Segments Corresponding to the Gene for Alanine-tRNA, PNAS, 60:1338-1344, (1968).
Hacia J.G. Resequencing and mutational analysis using oligonucleotide microarrays, Nature Genetics, 21(1 suppl): 42-47, 1999.
Hacia J.G. et al. Applications of DNA chips for genomic analysis. Mol Psychiatry. Nov. 1998;3(6):483-92.
Haeberle et al., Microfluidic platforms for lab-on-chip applications, Lab on a Chip 7(9):1094-1110, (2007).
Haffter et al. Enhancer independent mutants of the Cin recombinase have a relaxed topological specificity. (1988) EMBO J. 7:3991-3996.
Hansen, W. & Kelley M. Review of Mammalian DNA Repair and Transcriptional Implications, J. Pharmacol. & Exper. Therapeutics, 295(1):1-9, (2000).
Hardy et al., Reagents for the preparation of two oligonucleotides per synthesis (TOPSTM), Nucleic Acids Research, 22(15):2998-3004, (1994).
Hawley et al., Compilation and analysis of *Escherichia coli* promoter DNA sequences Nucl. Acid. Res. 11:2237-2255. 1983.
Hecker, K.H., et al. Error Analysis of chemically Synthesized Polynucleotides, BioTechniques, 24:256-260 (1998).
Heeb, S., et al. Small, Stable Shuttle Vectors Based on the Minimal pVS1 Replicon for Use in Gram-Negative Plant-Associated Bacteria. MPMI, 13(2):232-237 (2000).
Henegariu et al. Multiplex PCR: critical parameters and step-by-step protocol Biotechniques, 23(3): 504-511, (Sep. 1997).
Hermeling, S., et al. Structure-Immunogenicity Relationships of Therapeutic Proteins, Pharmaceutical Research, 21(6): 897-903, (Jun. 2004).
Higuchi et al. A general method of in vitro preparation and specific mutagenesis of DNA fragments: study of protein and DNA interactions, Nucleic Acids Research, 16(15):7351-7367 (1988).
Hoess et al. Interaction of the bacteriophage P 1 recombinase Cre with the recombining site loxP (1984) Proc. Natl. Acad. Sci. USA 81: 1026-1029.
Hoess et al. P 1 site-specific recombination: nucleotide sequence of the recombining sites (1982) Proc. Natl. Acad. Sci. USA 79: 3398-3402.
Hoess et al. The role of the loxP spacer region in PI site-specific recombination (1986), Nucleic Acids Res. 14: 2287-2300.
Hoess et al., Mechanism of strand cleavage and exchange in the Cre-lox site-specific recombination system (1985) J. Mol. Biol. 181: 351-362.
Holmes, Model studies for new o-nitrobenzyl photolabile linkers: substituent effects on the rates of photochemical cleavage, J. of Org. Chem., 62(8):2370-2380, (Apr. 18, 1997).
Hoover et al., DNAWorks: an automated method for designing oligonucleotides for PCR-based gene synthesis, Nucleic Acids Research, 30(10):e43 (7 pages), (2002).
Horton, R., et al. Engineering hybrid genes without the use of restriction enzymes: Gene splicing by overlap extension, Gene, 77:61-68, (1989).
Hyman, E., A new method of sequencing DNA, Analytical Biochemistry, 174(2):423-436, (Nov. 1, 1988).
Ibrahim EC et al. Serine/arginine-rich protein-dependent suppression of exon skipping by exonic splicing enhancers Proc Natl Acad Sci US A. Apr. 5, 2005;102(14):4927-8.
Ito R et al. Novel muteins of human necrosis factor alpha Biochimica Biophysica Acta (1991), vol. 1096, pp. 245-252.
Jayaraman K. et al. Polymerase chain reaction-mediated gene synthesis: synthesis of a gene coding for isozyme c of horseradish peroxidase. Proc Natl Acad Sci US A. May 15, 1991; 88(10): 4084-4088.
Jayaraman, et al. A PCR-mediated Gene synthesis strategy involving the assembly of oligonucleotides representing only one of the strands, Biotechniques, 12(3):392-398, (1992).
Jayaraman, K et al., A PCR-Mediated Gene Synthesis Strategy Involving the Assembly of Oligonucleotides Representing Only One of the Strands, Biotechniques, vol. 12, No. 3, pp. 392-398, 1992.
Jensen P.R. et al. The sequence of spacers between the consensus sequences modulates the strength of prokaryotic promoters Appl. Env. Microbiol. 64:82-87, 1998.
Jinek et al., A programmable dual-RNA-guided DNA endonuclease in adaptive bacterial immunity. Science. Aug. 17, 2012;337(6096):816-21. doi: 10.1126/science.1225829. Epub Jun. 28, 2012.
Johnston M. Gene chips: Array of hope for understanding gene regulation. Current Biology, 8: (5) R171, 1998.
Jones, T., et al. The Development of a Modified Human IFN-alpha2b Linked to the Fe Portion of Human IgG1 as a Novel Potential Therapeutic for the Treatment of Hepatitis C Virus Infection, Journal of Interferon & Cytokine Research, 24:560-572, (2004).
Kahl, J., et al. Solution-Phase Bioconjugate Synthesis Using Protected Oligonucleotides Containing 3'-Alkyl Carboxylic Acids, J. of Org. Chem., 64(2):507-510, (1999).
Kahl, J., et al., High-Yielding Method for On-Column Derivatization of Protected Oligodeoxy-nucleotides and Its Application to the Convergent Synthesis of 5',3'-Bis-conjugates, J. of Org. Chem., 63(15):4870, (1998).
Kampke T. Efficient primer design algorithms Bioinformatics, 2001, vol. 17, No. 3, pp. 214-225.
Kelly, B., et al., Miniaturizing chemistry and biology in microdroplets, Chem. Commun., 1773-1788, (2007).
Khaitovich, P., et al. Characterization of functionally active subribosomal particles from Thermus aquaticus, Proc. Natl. Acad. Sci., 96:85-90 (1999).
Kim et al., Precision genome engineering with programmable DNA-nicking enzymes. Genome Res. Jul. 2012;22(7):1327-33. doi:10.1101/gr.138792.112. Epub Apr. 20, 2012.
Kim J.H. et al. Solid-phase genetic engineering with DNA immobilized on a gold surface. J. Biotechnology, 2002, 96:213-22.
Kim, C., et al. Biological lithography: Improvements in DNA synthesis methods, J. Vac. Sci. Technol. B 22(6):3163-3167 (2004).
Kim, Y., et al. Insertion and Deletion Mutants of FokI Restriction Endonuclease, J. Biol. Chem., 269(50):31978-31982 (1994).
Kinde et al., Detection and quantification of rare mutations with massively parallel sequencing. Proc Natl Acad Sci U S A. Jun. 7, 2011;108(23):9530-5. doi: 10.1073/pnas.1105422108. Epub May 17, 2011. Supplemental Information.
Kisselev, L., et al. Termination of translation: interplay of mRNA, rRNAS and release factors?, The EMBO J., 22(2):175-182, (2003).
Kitamura, K., et al. Construction of Block-Shuffled Libraries of DNA for Evolutionary Protein Engineering: Y-Ligation- Based Block Shuffling. Protein Engineering, 15(10): 843-853, (Oct. 2002).
Kleppe K., et al. Studies of polynucleotides: repair replication of short synthetic DNA's as catalyzed by DNA polymerases, J. Mol. Biol. 56:341-361, (1971).
Kodumal., S., et al. Total synthesis of long DNA sequences: Synthesis of a contiguous 32-kb polyketide synthase gene cluster, PNAS, 101(44):15573-15578, (Nov. 2, 2004).
Kolisnychenko, V., et al. Engineering a Reduced *Escherichia coli* Genome, Genome Research, 12:640-647, (2002).
Kong, D., et al., Parallel gene synthesis in microfluidic device, Nucleic Acids Research, vol. 35, No. 8, pp. e61-1 (9 pages), (2007).
Kosuri et al. (Scalable gene synthesis by selective amplification of DNA pools from high-fidelity microchips, Nature Biotechnology 28, 1295-1299 (2010), Published online Nov. 28, 2010).
Kotera et al., A high-throughput and single-tube recombination of crude PCR products using a DNA polymerase inhibitor and type IIS restriction enzyme. J Biotechnol. Oct. 10, 2008;137(1-4):1-7. doi: 10.1016/j.jbiotec.2008.07.1816. Epub Jul. 23, 2008.
Kotsopoulou, E., et al. A Rev-Independent Human Immunodeficiency Virus Type 1 (HIV-1)-Based Vector That Exploits a Codon-Optimized HIV-1 gag-pol Gene, Journal of Virology, 74(10):4839-4852, (May 2000).
Kowalczykowski, S. In vitro reconstitution of homologous recombination reactions, Experientia, 50:204-215, (1994).
Kowalczykowski, S. Initiation of genetic recombination and recombination-dependent replication, TIBS, 25:156-165, (Apr. 2000).

(56) References Cited

OTHER PUBLICATIONS

Krieg a Real-time detection of nucleotide incorporation during complementary DNA strand analysis Chern. Bio. Chern. 4:589-592 (2003).

Kurian et al. DNA chip technology. J Pathol. Feb. 1999; 187(3):267-71.

Lamers, M., et al. ATP Increases the Affinity between MutS ATPase Domains, J. Biol. Chem., 279(42):43879-43885, (Oct. 15, 2004).

Lashkari et al. An automated multiplex oligonucleotide synthesizer: Development of high throughpout, low cost DNA synthesis. 1995, PNAS 92(17): 7912-7915.

Leamon, J., et al., A massively parallel PicoTiterPlate™ based platform for discrete picoliter- scale polymerase chain reactions, Electrophoresis, 24(21):3769-3777, (Nov. 2003).

Lebedenko et al. Method of artificial DNA splicing by directed ligation Nucleic Acids Research, 19: 6757-6761, 1991.

Lederman et al., DNA-directed peptide synthesis I. A comparison of T2 and *Escherichia coli* DNA-Directed Peptide Synthesis in Two Cell-Free Systems, Biochim, Biophys. Acta, vol. 149, pp. 235-258, (1967).

Lee, K., et al. Genetic approaches to Studying Protein Synthesis: Effects of Mutations at ?I516 and A535 in *Escherichia coli* 16S rRNA, J. Nutr., 131:2994S-3004S, (2001).

Leslie et al., Site-specific recombination in the replication terminus region of *Escherichia coli*: functional replacement of dif. (1995) EMBO J. 14: 1561-1570.

Lewis et al. Gene modification via plug and socket gene targeting. J Clin Invest. Jan. 1, 1996;97(1):3-5.

Lewis, J. & Hatfull, G. Control of directionality in intergrase-mediated recombination: examination of recombination directionality factors (RDFs) including Xis and Cox proteins, Nucl. Acids Res., 29(11):2205-2216 (2001).

Li et al., Alteration of the cleavage distance of Fok I restriction endonuclease by insertion mutagenesis. Proc Natl Acad Sci USA. 90(7): 2764-2768 (Apr. 1993).

Li, C., and Evans, R. Ligation independent cloning irrespective of restriction site compatibility, Nucl. Acids Res., 25(20):4165-4166 (1997).

Link, A., et al. Methods for generating precise deletions and insertions in the genome of wild-type *Escherichia coli*: Application to open reading frame characterization, J. Bacteriol., 179(20):6228-6237, (Oct. 1997).

Liu G. et al. DNA computing on surfaces. Nature, 403:175179 (2000).

Liu, W. et al. Genetic Incorporation of Unnatural Amino Acids Into Proteins in Mammalian Cells, Nature Methods, 4(3):239-244, (Mar. 2007).

Liu, Y., et al., DNA ligation of ultramicrovolume using EWOD microfluidic system with coplanar electrodes: DNA ligation of ultramicrovolume using a EWOD microfluidic system, J. of Micromechanics and Microengineering, 18(4):45017 (7 pages), (2008).

Lodish et al., Section 7.1 , DNA Cloning with Plasmid Vectors. Molecular Cell Biology, 4th Ed. W.H. Freeman. New York. 2000. Available from: www.ncbi.nlm.nih.gov/books/NBK21498.

Lu et al., Conjugative transposition: Tn916 integrase contains two independent DNA binding domains that recognize different DNA sequences '(1994) EMBO J. 13: 1541-1548.

Luo, P., et al. Development of a Cytokine Analog with Enhanced Stability Using Computational Ultrahigh Throughput Screening, Protein Science, 11:1218-1226, (2002).

Lutz, S. & Benkovic, J. Homology-Independent Protein Engineering, Current Opinion in Biotechnology, 11:319-324, (2000).

Mandecki et al. FokI method of gene synthesis Gene, 68:101-107 (1988).

Mandecki W. Oligonucleotide-directed double-strand break repair in plasmids of *Escherichia coli*: A method for site-specific mutagenesis. 1986, PNAS, 83:7177-7181.

Mannervik, B. Optimizing the Heterologous Expression of Glutathione Transferase, Methods in Enzymology, 401:254-265, (2005).

Margulies et al., Genome Sequencing in Microfabricated High-Density Picolitre Reactors, Nature. 437: 376-380 (2005). Supplemental materials.

Matzas et al. (High-fidelity gene synthesis by retrieval of sequence-verified DNA identified using high-throughput pyrosequencing, Nature Biotechnology 28, 1291-1294 (2010), Published online Nov. 28, 2010).

McCaughan et al., Single-Molecule Genomics, The Journal of Pathology, 220: 297-306, (Jan. 1, 2009).

McClain et al., Genome Sequence Analysis of Helicobacter Pylori Strains Associated with Gastric Ulceration and Gastric Cancer, BMC Genomics, Biomed Central Ltd, London, IK. 10(1):3 (2009).

McGall et al., Light-Directed Synthesis of High-Density Oligonucleotide Arrays Using Semiconductor Photoresists, Pro. Natl. Acad. Sci. 93(24):13555-13560 (1996).

Mei et al., Cell-Free Protein Synthesis in Microfluidic Array Devices, Biotechnol. Prog. 2007, 23:1305-1311.

Mercier et al. Structural and functional characterization of tnpI, a recombinase locus in Tn21 and related beta-lactamase transposons. (1990) J. Bacteriol. 172: 3745.

Metzker et al., Termination of DNA synthesis by novel 3'-modified-deoxyribonucleoside 5'-triphosphates, NAR, 22(20):4259-4267, (1994).

Metzker, Emerging technologies in DNA sequencing. Genome Res. Dec. 2005;15(12):1767-76.

Meyer-Leon et al. Purification of the FLP site-specific recombinase by affinity chromatography and re-examination of basic properties of the system (1987) Nucleic Acids Res. 15: 6469.

Mezard, C., et al. Recombination Between Similar But Not Identical DNA Sequences During Yeast Transformation Occurs Within Short Stretches Of Identity, Cell, 70:659-670, (Aug. 21, 1992).

Miick, S., et al. Crossover isomer bias is the primary sequence-dependent property of immobilized Holliday junctions, Proc. Natl. Acad. Sci. USA, 94:9080-9084, (Aug. 1997).

Milton, R., et al. Total Chemical Synthesis of a D-Enzyme: The Enantiomers ofHIV-1 Protease Show Demonstration of Reciprocal Chiral Substrate Specificity, Science, 256:1445-1448, (Jun. 5, 1992).

Mir et al. Sequencing by cyclic ligation and cleavage (CycLic) directly on a microarray captured template. Nucl. Acids Rse. vol. 37, No. 1 e5, 2008.

Mitra R.D. et al. Fluorescent in situ sequencing on polymerase colonies. Analytical Biochemistry, 320: 55-65 (2003).

Modrich, P. Strand-specific Mismatch Repair in Mammalian Cells, J. Biol. Chem., 272(40):24727-24730, (Oct. 3, 1997).

Moffitt et al. Recent Advances in Optical Tweezers. Annual Review of Biochemistry 77:205 (Feb. 2008).

Moore, G. & Maranas C. Computational Challenges in Combinatorial Library Design for Protein Engineering, AIChE Journal, 50(2):262-272, (Feb. 2004).

Morton, Oliver Life, Reinvented, Wired, http:www.wired.com/wired/archive!13.01/mit_pr.html (2005).

Muller, Ten years of gene targeting: targeted mouse mutants, from vector design to phenotype analysis. Mech Dev. Apr. 1999;82(1-2):3-21.

Nakamaye, K., et al. Direct sequencing of polymerase chain reaction amplified DNA fragments through the incorporation of deoxynucleoside alpha-thiotriphosphates, Nucleic Acids Research, 16(21):9947-9959, (1988).

Nakamura, Y. & Ito, K. How protein reads the stop codon and terminates translation, Genes to Cells, 3:265-278, (1998).

Nakayama et al., A system using convertible vectors for screening soluble recombinant proteins produced in *Escherichia coli* from randomly fragmented cDNAs, Bioch. and Biophys. Res. Comm., 312:825-830, (2003).

Ness, J., et al. DNA shuffling of subgenomic sequences of subtilisin, Nature Biotechnology 17: 893-896 (1999).

Ness, J., et al. Synthetic Shuffling Expands Functional Protein Diversity by Allowing Amino Acids to Recombine Independently Nature Biotechnology, 20:1251-1255, (Dec. 2002).

Neuman et al., Optical trapping. Rev Sci Instrum. Sep. 2004;75(9):2787-809.

Nilsson P. et al. Real-Time monitoring of DNA manipulations using biosensor technology Analytical Biochemistry, 1995, 224:400-408.

(56) References Cited

OTHER PUBLICATIONS

Nilsson, L., et al. Improved Heterologous Expression of Human Glutathione Transferase A4-4 by Random Silent Mutagenesis of Codons in the 5' Region, Biochemica et Biophysica Acta, 1528: 101-106, (2001).
Noirot, P. & Kolodner, R. DNA Strand Invasion Promoted by *Esherichia coli* RecT Protein, J. Biol. Chern., 273(20):12274-12280, (May 15, 1998).
Novy, R., et al. Ligation Independent Cloning: Efficient Directional Cloning of PCR Products, Novagen, Inc., InNovations, 5:1-3, (http://www.emdbiosciences.com/html/NVG/inNovations.html), (1996).
Orban et al. Tissue- and site-specific DNA recombination in transgenic mice (1992) Proc. Natl. Acad. Sci. 89: 6861-6865.
Osawa, S., et al. Recent Evidence for Evolution of the Genetic Code, Microbiological Reviews, 56(1):229-264, (Mar. 1992).
Osborn, A. & Boltner, D. When phage, plasmids, and transposons collide: genomic islands, and conjugative and mobilizable-transposons as a mosaic continuum, Plasmid, 48:202-212, (2002).
Pachuk et al. Chain reaction cloning: one step method for directional ligation of multiple DNA fragments Gene, 243(1-2): 19-25 (2000).
Padgett et al.. Creating seamless junctions independent of restriction sites in PCR cloning, Gene, Feb. 2, 1996, vol. 168, No. 1, pp. 31-35.
Pan et al., An approach for global scanning of single nucleotide variations, PNAS, 99(14):9346-9351, (Jul. 9, 2002).
Panet A. and Khorana G.H. Studies of polynucleotides: the linkage of deoxyribopolynucleotides templates to cellulaose and its use in their replication. J. Biol. Chern. 249(16):5213-5221 (1974).
Parr, R. & Ball, J. New donor vector for generation of histidine-tagged fusion proteins using the Gateway Cloning System, Plasmid, 49:179-183, (2003).
Pemov et al., DNA analysis with multiplex microarray-enhanced PCR. Nucleic Acids Res. Jan. 20, 2005;33(2):e11.
Peters, J. & Craig, N. Tn7: Smarter Than We Thought, Nature, 2:806-814, (Nov. 2001).
Petrik et al., Advances in Transfusion Medicine in the First Decade of the 21.sup.st Century: Advances in Miniaturized Technologies, Transfusion and Apheresis Science. 45(1): 45-51 (2011).
Pingoud et al., Type II restriction endonucleases—a historical perspective and more. Nucleic Acids Res. Jul. 2014;42(12):7489-527. doi: 10.1093/nar/gku447. Epub May 30, 2014. Review. Erratum in: Nucleic Acids Res. Sep. 19, 2016;44(16):8011.
Pon, Solid-phase supports for oligonucleotide synthesis, Methods Mol. Biol., 20:465-496, (1993).
Posfai, G., et al. In vivo excision and amplification of large segments of the *Escherichia coli* genome, Nucl. Acids Res., 22(12):2392-2398, (1994).
Posfai, G., et al. Markerless gene replacement in Escherichia coli stimulated by a double-strand break in the chromosome, Nucl. Acids Res., 27(22):4409-4415, (1999).
Prodromou, C. et al., Recursive PCR: A novel technique for total gene synthesis, Protein Engineering, vol. 5, No. 8, pp. 827-829, 1992.
Ramachandran et al., End-Point Limiting-Dilution Real-Time PCR Assay for Evaluation of Hepatitis C Virus Quasispecies in Serum: Performance Under Optimal and Suboptimal Conditions, Journal of Virological Methods. 151(2): 217-224 (2008).
Ramirez et al., Engineered zinc finger nickases induce homology-directed repair with reduced mutagenic effects. Nucleic Acids Res. Jul. 2012;40(12):5560-8. doi: 10.1093/nar/gks179. Epub Feb. 28, 2012.
Randegger et al., Real-time PCR and melting curve analysis for reliable and rapid detection of SHV extended-spectrum beta-lactamases. Antimicrob Agents Chemother. Jun. 2001;45(6):1730-6.
Regalado, A. Next Dream for Venter: Create Entire Set of Genes From Scratch, Wall Street Journal, A1, (Jun. 29, 2005).
Reyrat, J., et al. Counterselectable Markers: Untapped Tools for Bacterial Genetics and Pathogenesis, Infection and Immunity, 66(9):4011-4017, (Sep. 1998).

Richmond, K., et al., Amplification and assembly of chip-eluted DNA (AACED): a method for high-throughput gene synthesis, Nucleic Acids Research, 32(17): 5011-5018 (2004).
Roberts et al., RNA-peptide fusions for the in vitro selection of peptides and proteins, Proc Natl Acad Sci USA. 94(23): 12297-302, 1997.
Rouillard, J. et al. Gen2Oligo: Oligonucleotide design for in vitro gene synthesis, Nucleic Acids Research, 32: W176-W180, (2004).
Rouwendal, G., et al. Enhanced Expression in Tobacco of the Gene Encoding Green Fluorescent Protein by Modification of its Codon Usage, Plant Molecular Biology, 33:989-999, (1997).
Ryu, D.D.Y., et al. Recent Progress in Biomolecular Engineering, Biotechnol. Prog. 16:2-16 (2000).
Sa-Ardyen, P., et al. The flexibility of DNA double crossover molecules, Biophys. J., 84:3829-3837, (Jun. 2003).
Saha et al., The promoter of the Chinese hamster ovary dihydrofolate reductase gene regulates the activity of the local origin and helps define its boundaries. Genes Dev. Feb. 15, 2004;18(4):397-410. Epub Feb. 20, 2004.
Saiki, R., et al. Analysis of enzymatically amplified beta-globin and HLA-DQ alpha DNA with allele-specific oligonucleotide probes, Nature, 324(6093):163-166, (Nov. 13, 1986).
Sakabe, N., et al. A Bioinformatics Analysis of Alternative Exon Usage in Human Genes Coding for Extracellular Matrix Proteins, Genetics and Molecular Research, 3(4):532-544, (2004).
Sakamoto, K., et al. Site-Specific Incorporation of an Unnatural Amino Acid Into Proteins in Mammalian Cells, Nucleic Acids Research, 30(21):4692-4699, (2002).
Saks, M. Making sense out of nonsense, PNAS, 98(5): 2125-2127, (Feb. 27, 2001).
Saks, M., et al. An Engineered Tetrahymena tRNAGLn, for in Vivo Incorporation of Unnatural Amino Acids into Proteins by Nonsense Suppression, J. of Biol. Chem., 271(38):23169-23175, (Sep. 20, 1996).
Salyers, A., et al. Conjugative Transposons: an Unusual and Diverse Set of Integrated Gene Transfer Elements, Microbiological Reviews, 59(4):579-590, (Dec. 1995).
Sanjana, N. et al., A Transcription activator-like effector toolbox for genome engineering, Nature Protocols, Nature Publishing Group, GB, Vo. 7. No. 1, pp. 171-192, Jan. 1, 2012.
Sarrion-Perdigones et al., GoldenBraid: an iterative cloning system for standardized assembly of reusable genetic modules. PLoS One. 2011;6(7):e21622. doi:10.1371/journal.pone.0021622. Epub Jul. 7, 2011.
Sato et al. The cisA cistron of Bacillus subtilis sporulation gene spoIVC encodes a protein homologous to a site-specific recombinase (1990) J. Bacteriol. 172: 1092-1098.
Sato, T., et al. Production of menaquinone (vitamin K2)-7 by Bacillus subtilis, J. of Bioscience and Engineering, 91(1):16-20, (2001).
Sauer, Functional expression of the ere-lox site-specific recombination system in the yeast *Saccharomyces cerevisiae* (1987) Mol. Cell. Biol. 7: 2087-2096.
Schaerli, Y., et al., ContinuoFlow polymerase Chain reaction of single-copy DNA Microfluidic Microdroplets, Anal. Chem., 81: 302-306, (2009).
Scior, Annike et al., Directed PCR-free engineering of highly repetitive DNA sequences, BMC Biotechnology, Biomed Central Ltd., London, GB, vol. 11, No. 1, pp. 87, Sep. 23, 2011.
Semizarov, D., et al. Stereoisomers of Deoxynucleoside 5'-Triphosphates as Substrates for Template-dependent and- independent DNA Polymerases, J. Biol. Chem., 272(14) 9556-9560 (1997).
Seo, T., et al. Four-color DNA sequencing by synthesis on a chip using photocleavable fluorescent nucleotides, PNAS, 102(17):5926-5933, (Apr. 26, 2005).
Sgaramella, V., et al. Studies of polynucleotides, C.: A novel joining reaction catalyzed by T4-polynucleotide ligase, PNAS, 67(3): 1468-1475, (Nov. 1970).
Shabarova, Z., et al., Chemical ligation of DNA: the first non-enzymatic assembly of a biologically active gene, Nucl. Acids Res., 19(15):4247-4251, (1991).

(56) References Cited

OTHER PUBLICATIONS

Shao, Z., et al. Random-Priming in Vitro Recombination: An Effective Tool for Directed Evolution, Nucleic Acids Research, 26(2):681-683, (1998).

Shendure et al., Accurate Multiplex Polony Sequencing of an Evolved Bacterial Genome, Science. 309:1728-1732 (2005).

Shpaer, GeneAssist. Smith-Waterman and other database similarity searches and identification of motifs: Methods Mol. Biol. 70: 173-187, 1997.

Sieber, V., et al. Libraries of Hybrid Proteins From Distantly Related Sequences, Nature Biotechnology, 19:456-460, (May 2001).

Simon, D., et al. N-methyl-D-aspartate receptor antagonists disrupt the formation of a mammalian neural map Proc Natl Acad Sci USA, 89: 10593-10597, (Nov. 1992).

Smith et al., Single-step purification of polypeptides expressed in *Escherichia coli* as fusions with glutathione S-transferase, Gene, vol. 67, Issue 1, pp. 31-40, (1988).

Smith, H.O., et al. Generating a synthetic genome by whole genome assembly:<DX174 bacteriophage from synthetic oligonucleotides, PNAS, 100(26):15440-15445 (2003).

Smith, J. & Modrich, P. Mutation Detection with MutH, MutL, and MutS Mismatch Repair Proteins, Proc. Natl. Acad. Sci. USA, 93:4374-4379, (Apr. 1996).

Smith, J., et al. A detailed study of the substrate specificity of a chimeric restriction enzyme. Nucleic Acids Research 27(2):674-681 (1999).

Soderlind et al. Domain libraries: Synthetic diversity for de novo design of antibody V-regions. Gene, 160 (1995) 269-272.

Sprinzl, M. & Vassilenko, K. Compilation of tRNA sequences and sequences of tRNA genes, Nucleic Acids Research, 33:D139-D140 (2005).

Stamm et al., Sanchored PCR: PCR with CDNA Coupled to a solid phase, Nucleic Acids Research, 19(6):1350, (Mar. 25, 1991).

Stekel, Microarrays: Making Them and Using Them, Microarray Bioinformatics. Cambridge University Press. pp. 211-230 (2003).

Stemmer, DNA shuffling by random fragmentation and reassembly: in vitro recombination for molecular evolution, Proc. Natl. Acad. Sci. USA, 91:10747-10751, (1994).

Stemmer, W.P.C. et al., Single-step assembly of a gene and entire plasmid from large numbers of oligodeoxyribonucleotides, Gene, vol. 164, No. 1, pp. 49-53, 1995.

Sternberg et al. Site-specific Recombination and Its Role in the Life Cycle of Bacteriophage Pl Cold Spring Harbor Symp. Quant. Biol. 45: 297-309, 1981.

Steuer, Shawn et al. Chimeras of the Homing Endonuclease Pi-SceI and the Homologous Candida Tropicalis Intein A Study to Explore the Possibility of Exchanging DNA-Binding Modules to Obtain Highly Specific Endonucleases With Altered Specificity ChemBioChem, vol. 5 Issue 2, pp. 206-213, (2004).

Strizhov et al. A synthetic cryiC gene, encoding a Bacillus Thuringiensis delta-endotoxin, confers Spodotera resistance in Alfafa and Tobacco p. N.AS., 1996, vol. 93, No. 26, pp. 15012-15017.

Szybalski et al., Class-IIS restriction enzymes—a review. Gene. Apr. 1991;100:13-26. Review. Erratum in: Gene Dec. 20, 1991;109(1):169.

Tan, S., et al. Zinc-finger protein-targeted gene regulation: Genomewide single-gene specificity, PNAS, 100(21):11997-12002, (Oct. 14, 2003).

Tang K. et al. Chip-based genotyping by mass spectrometry. PNAS, 96: 10016-10020 (1999).

Teh et al., Droplet microfluidics, Lab on Chip. 2008;8(2):198-220.

Third Party Observation under Article 115 EPC for EP publication No. 2864531, filed May 18, 2018.

Tian et al. Accurate multiplex gene synthesis from programmable DNA microchips, Nature, 432:1050-1054, (Dec. 2004).

Tsai et al., Dimeric CRISPR RNA-guided FokI nucleases for highly specific genome editing. Nat Biotechnol. Jun. 2014;32(6):569-76. doi: 10.1038/nbt.2908. Epub Apr. 25, 2014. Online Methods.

Tsutakawa, S. & Morikawa, K. The Structural Basis of Damaged DNA Recognition and Endonucleolytic Cleavage for Very Short Patch Repair Endonuclease, Nucleic Acids Research, 29(18):3775-3783, (2001).

Tucker et al., Massively parallel sequencing: the next big thing in genetic medicine. Am J Hum Genet. Aug. 2009;85(2):142-54. doi:10.1016/j.ajhg.2009.06.022.

Urata, H., et al. Synthesis and properties of mirror-image DNA, 20(13):3325-3332 (1992).

Venkatesan et al., Improved Utility of Photolabile Solid Phase Synthesis Supports for the Synthesis of Oligonucleotides Containing 3'-Hydroxyl Termini, J. of Org. Chem., 61:525-529, (Jan. 26, 1996).

Verma et al., Modified Oligonucleotides: Synthesis and Strategy for Users, Annu. Rev. Biochem., 67:99-134, (1998).

Vogelstein et al., Digital PCR, Pro. Natl. Acad. Sci. 96(16):9236-9241 (1999).

Von Neumann T. The general and logical theory of automata, Pergamon Press, Taub A.H (Editor) vol. 5, 288-326 (1948).

Wang et al., De novo assembly and characterization of root transcriptome using Illumina paired-end sequencing and development of cSSR markers in sweet potato (*Ipomoea batatas*), BMC Genomics, 2010, vol. 11, pp. 1-14.

Wang et al., Targeted gene addition to a predetermined site in the human genome using a ZFN-based nicking enzyme. Genome Res. Jul. 2012;22(7):1316-26. doi: 10.1101/gr.122879.111. Epub Mar. 20, 2012.

Waters, V. Conjugation between bacterial and mammalian cells, Nature Genetics, 29:375-376, (Dec. 2001).

Weber, Ernst et al., A Modular Cloning System for Standardized Assembly of Multigene Constructs, PLoS One, page e16765, vol. 6, No. 2, Feb. 18, 2011.

Weiler and Hoheisel, Combining the Preparation of Oligonucleotide Arrays and Synthesis of High-Quality Primers. Analytical Biochemistry, vol. 243, Issue 2, Dec. 15, 1996, pp. 218-227.

Weiner et al., Kits and their unique role in molecular biology: a brief retrospective. Biotechniques. Apr. 2008;44(5):701-4. doi: 10.2144/000112796.

Weisberg, et al., Site-specific recombination in Phage Lambda, In: Lambda II, Hendrix, et al. Eds., Cold Spring Harbor Press, Cold Spring Harbor, NY (1983) pp. 211-250.

Werner et al., Fast track assembly of multigene constructs using Golden Gate cloning and the MoClo system, Bioengineered Bugs, Jan. 1, 2012;3(1):38-43.

Wheeler DL Database resources of the National Center for Biotechnology Information Nucleic Acids Res. 29(1): 11-6 (Jan. 2001).

White et al. (Digital PCR provides sensitive and absolute calibration for high throughput sequencing, BMC Genomics, 2009, 10:116, Published: Mar. 19, 2009).

Wiedmann, M., Ligase chain reation (:CR)—overview and applications, 3:S51-S64, http://genome.cshlp.org/content/3/4/S51.refs.html, Copyright 1994 by Cold Spring Harbor Laboratory.

Wilgenbus & Lichter DNA chip technology ante portas J. Mol. Med 1999, 77:761-768.

Williams et al., Modifying the stereochemistry of an enzyme-catalyzed reaction by directed evolution. Proc Natl Acad Sci U S A. Mar. 18, 2003;100(6):3143-8. Epub Mar. 7, 2003.

Xie, J. & Schultz, P. An Expanding Genetic Code, Methods A Companion to Methods in Enzymology, 36:227-238, (2005).

Xiong et al. PCR based accurate synthesis of long DNA sequences Nature protocols 1 (2): 791 (2006).

Xiong et al., Non-Polymerase-Cycling-Assembly-Based Chemical Gene Synthesis: Strategies, Methods, and Progress; Biotechnology Advances; Elsevier Publishing; Barking, GB; vol. 26; No. 2; pp. 121-134; Nov. 7, 2007.

Xiong, A., et al. A simple, rapid, high-fidelity and cost-effective PCR-based two-step DNA synthesis method for long gene sequences, Nucleic Acids Research, 32(12):e98 (10 pages), (2004).

Xu et al. Nonenzymatic autoligation in direct three-color detection of RNA and DNA point mutations, Nature Biotechnology, 19:148-152, (Feb. 2001).

Xu et al., High sequence fidelity in a non-enzymatic DNA autoligation reaction, Nucleic Acids Research, 27(3):875-881, (1999).

(56) References Cited

OTHER PUBLICATIONS

Xu, Y. & Kool, E. A novel 5'-iodonucleoside allows efficient nonenzymatic ligation of single-stranded and duplex DNAs, Tetrahedron Letters, 38(32):5595-5598, (1997).

Xuei et al. Use of SAM(2)(R) biotin capture membrane in microarrayed compound screening (mu ARCS) format for nucleic acid polymerization assays Journal of Biomolecular Screening 8:273-282 (2003).

Yan et al., Polymer membranes with two-dimensionally arranged pores derived from monolayers of silica particles, Chem. Mater. 16(9): 1622-1626 (2004).

Yehezkel et al. (De novo DNA synthesis using single molecule PCR, Nucleic Acids Research, 2008, vol. 36, No. 17, e107, Published online Jul. 30, 2008).

Yolov et al. RNA-synthesis by use of T7-RNA-Polymerase and immobilized DNA in a flowing-type reactor. Bioorganicheskaya Khimiya, 17:789-794 (1991 ).

Yoon, Y. & Koob, M. Efficient cloning and engineering of entire mitochondrial genomes in *Escherichia coli* and transfer into transcriptionally active mitochondria, Nucleic Acids Research, 31(5):1407-1415, (2003).

Yoon, Y., et al. Cre/loxP-mediated in vivo excision of large segments from yeast genome and their amplification based on the 2 um plasmid-derived system, Gene, 223:67-76, (1998).

Yosef et al., Restoration of gene function by homologous recombination: from PCR to gene expression in one step. Appl. Environ. Microbiol. Dec. 2004;70(12):7156-60.

Young et al., Two-step Total Gene Synthesis Method Nucleic Acids Research, 32(7):e59 (6 pages), (2004).

Zha, D., et al. Assembly of Designed Oligonucleotides as an Efficient Method for Gene Recombination: A New Tool in Directed Evolution, ChemBioChem, 4:34-39, (2003).

Zhang et al., PCR microfluidic devices for DNA amplification, Biotechnology Advances, 24(3):243-284, 2006.

Zhang, P. et al. Rational Design of a Chimeric Endonuclease Targeted to NotI Recognition Site Protein Engineering Design & Selection, 20(10):497-504, (Oct. 2007).

Zhang, Z., et al. Selective Incorporation of 5-Hydroxytryptophan Into Proteins in Mammalian Cells, Proceedings of the National Academy of Sciences of the United States of America, 101(24):8882-8887, (Jun. 15, 2004).

Zhao, H., et al. Molecular Evolution By Staggered Extension Process (Step) In Vitro Recombination, Nature Biotechnology, 16:258-261, (Mar. 1998).

Zhou X. et al. Microfluidic PicoArray synthesis of oligodeoxynucleotides and simultaneous assembling of multiple DNA sequences Nucleic Acids Research , 32(18): 5409-5417 (2004).

Zhu et al., (1995). Cleavage-dependent Ligation by the FLP Recombinase. J Biol Chem 270: 23044-23054.

\* cited by examiner

```
TCGCGCGTTTCGGTGATGACGGTGAAAACCTCTGACACATGCAGCTCCCGGAGACGGTCACAGCTTGTCTGTAAGC
GGATGCCGGGAGCAGACAAGCCCGTCAGGGCGCGTCAGCGGGTGTTGGCGGGTGTCGGGGCTGGCTTAACTATG
CGGCATCAGAGCAGATTGTACTGAGAGTGCACCATATGCGGTGTGAAATACCGCACAGATGCGTAAGGAGAAAATA
CCGCATCAGGCGCCATTCGCCATTCAGGCTGCGCAACTGTTGGGAAGGGCGATCGGTGCGGGCCTCTTCGCTATTA
CGCCAGCTGGCGAAAGGGGGATGTGCTGCAAGGCGATTAAGTTGGGTAACGCCAGGGTTTTCCCAGTCACGACGTT
GTAAAACGACGGCCAGTGAATTAGTGTTGAGACCATTCAGCTCCGGTCTCGACACTGAGCTTGGCGTAATCATGGTC
ATAGCTGTTTCCTGTGTGAAATTGTTATCCGCTCACAATTCCACACAACATACGAGCCGGAAGCATAAAGTGTAAAGC
CTGGGGTGCCTAATGAGTGAGCTAACTCACATTAATTGCGTTGCGCTCACTGCCCGCTTTCCAGTCGGGAAACCTGT
CGTGCCAGCTGCATTAATGAATCGGCCAACGCGCGGGGAGAGGCGGTTTGCGTATTGGGCGCTCTTCCGCTTCCTC
GCTCACTGACTCGCTGCGCTCGGTCGTTCGGCTGCGGCGAGCGGTATCAGCTCACTCAAAGGCGGTAATACGGTTA
TCCACAGAATCAGGGGATAACGCAGGAAAGAACATGTGAGCAAAAGGCCAGCAAAAGGCCAGGAACCGTAAAAAGG
CCGCGTTGCTGGCGTTTTTCCATAGGCTCCGCCCCCCTGACGAGCATCACAAAAATCGACGCTCAAGTCAGAGGTG
GCGAAACCCGACAGGACTATAAAGATACCAGGCGTTTCCCCCTGGAAGCTCCCTCGTGCGCTCTCCTGTTCCGACC
CTGCCGCTTACCGGATACCTGTCCGCCTTTCTCCCTTCGGGAAGCGTGGCGCTTTCTCATAGCTCACGCTGTAGGTA
TCTCAGTTCGGTGTAGGTCGTTCGCTCCAAGCTGGGCTGTGTGCACGAACCCCCCGTTCAGCCCGACCGCTGCGC
CTTATCCGGTAACTATCGTCTTGAGTCCAACCCGGTAAGACACGACTTATCGCCACTGGCAGCAGCCACTGGTAACA
GGATTAGCAGAGCGAGGTATGTAGGCGGTGCTACAGAGTTCTTGAAGTGGTGGCCTAACTACGGCTACACTAGAAG
AACAGTATTTGGTATCTGCGCTCTGCTGAAGCCAGTTACCTTCGGAAAAAGAGTTGGTAGCTCTTGATCCGGCAAAC
AAACCACCGCTGGTAGCGGTGGTTTTTTTGTTTGCAAGCAGCAGATTACGCGCAGAAAAAAAGGATCTCAAGAAGAT
CCTTTGATCTTTTCTACGGGGTCTGACGCTCAGTGGAACGAAAACTCACGTTAAGGGATTTTGGTCATGAGATTATCA
AAAAGGATCTTCACCTAGATCCTTTTAAATTAAAAATGAAGTTTTAAATCAATCTAAAGTATATATGAGTAAACTTGGTC
TGACAGTCAGAAGAACTCGTCAAGAAGGCGATAGAAGGCGATGCGCTGCGAATCGGGAGCGGCGATACCGTAAAG
CACGAGGAAGCGGTCAGCCCATTCGCCGCCAAGCTCTTCAGCAATATCACGGGTAGCCAACGCTATGTCCTGATAG
CGGTCCGCCACACCCAGCCGGCCACAGTCGATGAATCCAGAAAAGCGGGCCATTTTCCACCATGATATTCGGCAAGC
AGGCATCGCCATGGGTCACGACGAGATCCTCGCCGTCGGGCATGCTCGCCTTGAGCCTGGCGAACAGTTCGGCTG
GCGCGAGCCCCTGATGCTCTTCGTCCAGATCATCCTGATCGACAAGACCGGCTTCCATCCGAGTACGTGCTCGCTC
GATGCGATGTTTCGCTTGGTGGTCGAATGGGCAGGTAGCCGGATCAAGCGTATGCAGCCGCCGCATTGCATCAGCC
ATGATGGATACTTTCTCGGCAGGAGCAAGGTGAGATGACAGGAGATCCTGCCCCGGCACTTCGCCCAATAGCAGCC
AGTCCCTTCCCGCTTCAGTGACAACGTCGAGCACAGCTGCGCAAGGAACGCCCGTCGTGGCCAGCCACGATAGCC
GCGCTGCCTCGTCTTGCAGTTCATTCAGGGCACCGGACAGGTCGGTCTTGACAAAAGAACCGGGCGCCCCTGCG
CTGACAGCCGGAACACGGCGGCATCAGAGCAGCCGATTGTCTGTTGTGCCCAGTCATAGCCGAATAGCCTCTCCAC
CCAAGCGGCCGGAGAACCTGCGTGCAATCCATCTTGTTCAATCATACTCTTCCTTTTTCAATATTATTGAAGCATTTAT
CAGGGTTATTGTCTCATGAGCGGATACATATTTGAATGTATTTAGAAAAATAAACAAATAGGGGTTCCGCGCACATTT
CCCCGAAAAGTGCCACCTGACGTCTAAGAAACCATTATTATCATGACATTAACCTATAAAAATAGGCGTATCACGAGG
CCCTTTCGTC
```

FIG. 5

SEQUENCE LISTING

<160> NUMBER OF SEQ ID NOS: 1

<210> SEQ ID NO 1
<211> LENGTH: 2608
<212> TYPE: DNA
<213> ORGANISM: Artificial Sequence
<220> FEATURE:
<223> OTHER INFORMATION: Synthetic Polynucleotide

<400> SEQUENCE: 1

| | | | | | | |
|---|---|---|---|---|---|---|
| tcgcgcgttt | cggtgatgac | ggtgaaaacc | tctgacacat | gcagctcccg | gagacggtca | 60 |
| cagcttgtct | gtaagcggat | gccgggagca | gacaagcccg | tcagggcgcg | tcagcgggtg | 120 |
| ttggcgggtg | tcggggctgg | cttaactatg | cggcatcaga | gcagattgta | ctgagagtgc | 180 |
| accatatgcg | gtgtgaaata | ccgcacagat | gcgtaaggag | aaaataccgc | atcaggcgcc | 240 |
| attcgccatt | caggctgcgc | aactgttggg | aagggcgatc | ggtgcgggcc | tcttcgctat | 300 |
| tacgccagct | ggcgaaaggg | ggatgtgctg | caaggcgatt | aagttgggta | acgccagggt | 360 |
| tttcccagtc | acgacgttgt | aaaacgacgg | ccagtgaatt | agtgttgaga | ccattcagct | 420 |
| ccggtctcga | cactgagctt | ggcgtaatca | tggtcatagc | tgtttcctgt | gtgaaattgt | 480 |
| tatccgctca | caattccaca | acatacga | gccggaagca | taaagtgtaa | agcctggggt | 540 |
| gcctaatgag | tgagctaact | cacattaatt | gcgttgcgct | cactgcccgc | tttccagtcg | 600 |
| ggaaacctgt | cgtgccagct | gcattaatga | atcggccaac | gcgcggggag | aggcggtttg | 660 |
| cgtattgggc | gctcttccgc | ttcctcgctc | actgactcgc | tgcgctcggt | cgttcggctg | 720 |
| cggcgagcgg | tatcagctca | ctcaaaggcg | gtaatacggt | tatccacaga | atcaggggat | 780 |
| aacgcaggaa | agaacatgtg | agcaaaaggc | cagcaaaagg | ccaggaaccg | taaaaaggcc | 840 |
| gcgttgctgg | cgttttccca | taggctccgc | cccctgacg | agcatcacaa | aaatcgacgc | 900 |
| tcaagtcaga | ggtggcgaaa | cccgacagga | ctataaagat | accaggcgtt | tccccctgga | 960 |
| agctccctcg | tgcgctctcc | tgttccgacc | ctgccgctta | ccggatacct | gtccgccttt | 1020 |
| ctcccttcgg | gaagcgtggc | gctttctcat | agctcacgct | gtaggtatct | cagttcggtg | 1080 |
| taggtcgttc | gctccaagct | gggctgtgtg | cacgaacccc | ccgttcagcc | cgaccgctgc | 1140 |
| gccttatccg | gtaactatcg | tcttgagtcc | aacccggtaa | gacacgactt | atcgccactg | 1200 |
| gcagcagcca | ctggtaacag | gattagcaga | gcgaggtatg | taggcggtgc | tacagagttc | 1260 |
| ttgaagtggt | ggcctaacta | cggctacact | agaagaacag | tatttggtat | ctgcgctctg | 1320 |
| ctgaagccag | ttaccttcgg | aaaaagagtt | ggtagctctt | gatccggcaa | acaaaccacc | 1380 |
| gctggtagcg | gtggtttttt | tgtttgcaag | cagcagatta | cgcgcagaaa | aaaaggatct | 1440 |
| caagaagatc | ctttgatctt | ttctacgggg | tctgacgctc | agtggaacga | aaactcacgt | 1500 |
| taagggattt | tggtcatgag | attatcaaaa | aggatcttca | cctagatcct | ttaaattaa | 1560 |
| aaatgaagtt | ttaaatcaat | ctaaagtata | tatgagtaaa | cttggtctga | cagtcagaag | 1620 |
| aactcgtcaa | gaaggcgata | gaaggcgatg | cgctgcgaat | cgggagcggc | gataccgtaa | 1680 |
| agcacgagga | agcggtcagc | ccattcgccg | ccaagctctt | cagcaatatc | acgggtagcc | 1740 |
| aacgctatgt | cctgatagcg | gtccgccaca | cccagccggc | cacagtcgat | gaatccagaa | 1800 |
| aagcggccat | tttccaccat | gatattcggc | aagcaggcat | cgccatgggt | cacgacgaga | 1860 |
| tcctcgccgt | cgggcatgct | cgccttgagc | ctggcgaaca | gttcggctgg | cgcgagcccc | 1920 |

```
tgatgctctt cgtccagatc atcctgatcg acaagaccgg cttccatccg agtacgtgct    1980
cgctcgatgc gatgtttcgc ttggtggtcg aatgggcagg tagccggatc aagcgtatgc    2040
agccgccgca ttgcatcagc catgatggat actttctcgg caggagcaag gtgagatgac    2100
aggagatcct gccccggcac ttcgcccaat agcagccagt cccttcccgc ttcagtgaca    2160
acgtcgagca cagctgcgca aggaacgccc gtcgtggcca gccacgatag ccgcgctgcc    2220
tcgtcttgca gttcattcag ggcaccggac aggtcggtct tgacaaaaag aaccgggcgc    2280
ccctgcgctg acagccggaa cacggcggca tcagagcagc cgattgtctg ttgtgcccag    2340
tcatagccga atagcctctc cacccaagcg gccggagaac ctgcgtgcaa tccatcttgt    2400
tcaatcatac tcttcctttt tcaatattat tgaagcattt atcagggtta ttgtctcatg    2460
agcggataca tatttgaatg tatttagaaa aataaacaaa taggggttcc gcgcacattt    2520
ccccgaaaag tgccacctga cgtctaagaa accattatta tcatgacatt aacctataaa    2580
aataggcgta tcacgaggcc ctttcgtc                                        2608
```

METHODS FOR NUCLEIC ACID ASSEMBLY AND HIGH THROUGHPUT SEQUENCING

RELATED APPLICATIONS

This application is a continuation under 35 U.S.C. § 120 of U.S. application Ser. No. 16/714,208, filed Dec. 13, 2019, now issued as U.S. Pat. No. 11,072,789, which is a continuation under 35 U.S.C. § 120 of U.S. application Ser. No. 14/408,103, filed Dec. 15, 2014, which is a national stage filing under 35 U.S.C. § 371 of International Application No. PCT/US2013/047370, filed Jun. 24, 2013, which claims the benefit of and priority to U.S. Provisional Application No. 61/664,118, filed Jun. 25, 2012, and U.S. Provisional Application No. 61/731,627, filed Nov. 30, 2012. The entire content of each of the above referenced applications is incorporated herein by reference in its entirety.

FIELD OF THE INVENTION

Methods and apparatuses provided herein relate to the synthesis and assembly of high fidelity nucleic acids and nucleic acid libraries having a predefined sequence. More particularly, methods and apparatuses are provided for polynucleotide synthesis, error reduction, and/or high throughput sequence verification.

BACKGROUND

Using the techniques of recombinant DNA chemistry, it is now common for DNA sequences to be replicated and amplified from nature and then disassembled into component parts. As component parts, the sequences are then recombined or reassembled into new DNA sequences. However, reliance on naturally available sequences significantly limits the possibilities that may be explored by researchers. While it is now possible for short DNA sequences to be directly synthesized from individual nucleosides, it has been generally impractical to directly construct large segments or assemblies of polynucleotides, i.e., polynucleotide sequences longer than about 400 base pairs.

Oligonucleotide synthesis can be performed through massively parallel custom syntheses on microchips (Zhou et al. (2004) Nucleic Acids Res. 32:5409; Fodor et al. (1991) Science 251:767). However, current microchips have very low surface areas and hence only small amounts of oligonucleotides can be produced. When released into solution, the oligonucleotides are present at picomolar or lower concentrations per sequence, concentrations that are insufficiently high to drive bimolecular priming reactions efficiently. Current methods for assembling small numbers of variant nucleic acids cannot be scaled up in a cost-effective manner to generate large numbers of specified variants. As such, a need remains for improved methods and devices for high-fidelity gene assembly and the like.

Furthermore, oligonucleotides on microchips are generally synthesized via chemical reactions. Spurious chemical reactions cause random base errors in oligonucleotides. One of the critical limitations in chemical nucleic acid synthesis is the error-rate. The error rate of chemically-synthesized oligonucleotides (e.g. deletions at a rate of 1 in 100 bases and mismatches and insertions at about 1 in 400 bases) exceeds the error rate obtainable through enzymatic means of replicating an existing nucleic acid (e.g., PCR). Therefore, there is an urgent need for new technology to produce high yield high-fidelity polynucleotides in a cost efficient manner.

SUMMARY

Aspects of the invention relate to methods, systems and compositions for preparing and/or assembling high fidelity polymers. Also provided herein are devices and methods for processing nucleic acid assembly reactions and assembling nucleic acids. It is an object of this invention to provide practical, economical methods of synthesizing custom polynucleotides. It is a further object to provide methods of producing synthetic polynucleotides that have lower error rates than synthetic polynucleotides made by methods known in the art.

According to some embodiments, the invention provides a method for producing a target nucleic acid having a predefined sequence. In some embodiments, the method comprises the step of providing a plurality of oligonucleotides, wherein each oligonucleotides comprises (i) an internal sequence identical to a different portion of a sequence of a target nucleic acid, (ii) a 5' sequence flanking the 5' end of the internal sequence and a 3' flanking sequence flanking the 3' end of the internal sequence, each of the flanking sequence comprising a primer recognition site for a primer pair and a restriction enzyme recognition site. The method further comprises, in some embodiments, amplifying at least a subset of the oligonucleotides using the primer pair thereby generating a plurality of amplified oligonucleotides. The plurality of amplified oligonucleotides can then be exposed to a restriction enzyme and ligase in a single pool, wherein the restriction enzyme is capable of recognizing the restriction enzyme recognition site, thereby generating the target nucleic acid.

In some embodiments, the method comprises subjecting the assembled target nucleic acid to sequence verification. In some embodiments, the amplified double stranded oligonucleotides can comprise a sequence error or mismatch. In some embodiments, the method comprises subjecting the plurality of amplified oligonucleotides to error removal. In some embodiments, the plurality of amplified oligonucleotides can be contacted with a mismatch binding agent. The mismatch binding agent can selectively associate with the double-stranded oligonucleotides comprising a mismatch, resulting in a binding and cleaving action. In some embodiments, the plurality of amplified oligonucleotides can be contacted with a mismatch recognizing agent, for example, a chemical such as lysine, piperidine or the like.

In some embodiments, the restriction enzyme and the ligase are added to a single pool of amplified oligonucleotides under conditions suitable to promote digestion and ligation thereby generating a mixture comprising the assembled target nucleic acid sequences, and the flanking regions. In some embodiments, each flanking region comprises a common primer recognition site. In some embodiments, the restriction enzyme is a type IIS restriction enzyme. Digestion with the type IIS restriction enzyme can produce a plurality of cohesive end double-stranded construction oligonucleotides and the plurality of cohesive end double stranded construction oligonucleotides can be ligated in a unique linear arrangement.

In some embodiments, the method comprises amplifying the target nucleic acid using a primer pair capable of recognizing the primer recognition sites at the 5' end and 3' end of the target nucleic acid. In some embodiments, the method comprises sequencing the target nucleic acid to confirm its sequence accuracy, for example, by high throughput sequencing. In some embodiments, the method comprises isolating at least one target nucleic acid having the predefined sequence from a pool of nucleic acid sequences.

According to some embodiments, the invention provides a method for further processing the isolated nucleic acids. In some embodiments, the method comprises assembling at least two target nucleic acids. The step of assembling can be by hierarchical assembly. In some embodiments, the at least two target nucleic acids are subjected to restriction enzyme digestion and ligation thereby forming a long target nucleic acid construct, for example, at least about 10 kilobases or 100 kilobases in length.

According to some embodiments, the invention provides a method for producing a target nucleic acid having a predefined sequence in a vector. In some embodiments, a plurality of oligonucleotides are provided, each oligonucleotide comprising (i) an internal sequence identical to a different portion of a sequence of a target nucleic acid, (ii) a 5' flanking sequence flanking the 5' end of the internal sequence and a 3' flanking sequence flanking the 3' end of the internal sequence, each of the flanking sequence comprising a primer recognition site for a primer pair and a restriction enzyme recognition site for a restriction endonuclease. In some embodiments, at least a subset of the oligonucleotides can be amplified using the primer pair thereby generating a plurality of amplified oligonucleotides. In some embodiments, the plurality of amplified oligonucleotides can be subjected to error removal and/or correction. In some embodiments, a circular vector having a restriction enzyme recognition site for the restriction endonuclease is provided. In some embodiments, the plurality of amplified oligonucleotides and circular vector can be exposed to the restriction enzyme and ligase in a single pool, wherein the restriction enzyme is capable of recognizing the restriction enzyme recognition sites, thereby assembling the target nucleic acid in the vector. In some embodiments, the method further comprises transforming the vector into a host cell and sequence verifying the target nucleic acid sequence.

According to some embodiments, the invention provides a composition for the assembly of a target nucleic acid having a predefined sequence. In some embodiments, the composition comprises a plurality of oligonucleotides, wherein each oligonucleotide comprises (i) an internal sequence identical to a different portion of a sequence of a target nucleic acid, (ii) 5' flanking sequence flanking the 5' end of the internal sequence and 3' flanking sequence flanking the 3' end of the internal sequence, each of the flanking sequence comprising a primer recognition site for a primer pair and a restriction enzyme recognition site for a restriction endonuclease. In some embodiments, the composition further comprises a restriction endonuclease and/or a ligase. In some embodiments, the composition further comprises a vector comprising a pair of enzyme recognition sites for a restriction endonuclease. In some embodiments, the restriction endonuclease is a type IIS restriction endonuclease.

In some embodiments, the plurality of oligonucleotides is amplified and/or error corrected.

In some aspects of the invention, the method of producing a target nucleic acid having a predefined sequence comprises providing a first mixture comprising (i) a restriction enzyme, and (ii) a first pool of oligonucleotides comprising a first oligonucleotide comprising a sequence identical to the 5' end of the target nucleic acid, a second oligonucleotide comprising a sequence identical to the 3' end of the target nucleic acid; and a plurality of oligonucleotides comprising a sequence identical to a different portion of a sequence of a target nucleic acid, each of the oligonucleotides having an overlapping sequence region corresponding to a sequence region in a next oligonucleotide, the oligonucleotides in the first pool together comprising the target nucleic acid sequence; and exposing the mixture to a ligase, thereby generating the target nucleic acid. The target nucleic acid can then be subjected to sequence verification.

In some embodiments, the methods of the invention comprise providing a pool of construction oligonucleotides and involve amplification of the oligonucleotides at different stages. The term "construction oligonucleotide" refers to a single stranded oligonucleotide that may be used for assembling nucleic acid molecules that are longer than the construction oligonucleotide itself. Construction oligonucleotides may be single stranded oligonucleotides or double stranded oligonucleotides. In some embodiments, construction oligonucleotides are synthetic oligonucleotides and may be synthesized in parallel on a substrate.

In some embodiments, the method further comprises prior to providing the first mixture, the step of providing a plurality of construction oligonucleotides, wherein each construction oligonucleotide comprises (i) an internal sequence identical to a different portion of a sequence of a target nucleic acid, (ii) 5' flanking sequence flanking the 5' end of the internal sequence and a 3' flanking sequence flanking the 3' end of the internal sequence, each flanking region comprising a primer recognition site for a primer pair and a restriction enzyme recognition site. In some embodiments, each flanking region can comprise a common primer recognition site. In some embodiments, the plurality of construction oligonucleotides can be amplified. In some embodiments, the oligonucleotides can comprise a sequence error or mismatch. In some embodiments, the plurality of amplified oligonucleotides can be subjected to error removal. For example, the plurality of amplified oligonucleotides can be contacted with a mismatch binding agent, wherein the mismatch binding agent selectively binds and cleaves the double-stranded oligonucleotides comprising a mismatch.

In some embodiments, the restriction enzyme and the ligase can be added to a single pool of amplified oligonucleotides under conditions suitable to promote digestion and ligation thereby generating a mixture comprising the assembled target nucleic acid sequences, and the flanking regions. In some embodiments, the restriction enzyme can be a type IIS restriction enzyme and digestion with the type IIS restriction enzyme can produce a plurality of cohesive end double-stranded oligonucleotides and wherein the plurality of cohesive end double stranded oligonucleotides are ligated in a unique linear arrangement.

In some embodiments, the method further comprises amplifying the target nucleic acid using a primer pair capable of recognizing a primer recognition site at the 5' end of the first oligonucleotide and 3' end of second oligonucleotide.

In some embodiments, the method further comprises sequencing the target nucleic acid to confirm its sequence accuracy, for example, by high throughput sequencing.

In some embodiments, the method further comprises isolating at least one target nucleic acid having the predefined sequence from a pool of nucleic acid sequences.

In some embodiments, the method further comprises processing the target nucleic acids.

In some embodiments, the method further comprises providing a second mixture comprising (i) a restriction enzyme, and (ii) a second pool of oligonucleotides comprising a first oligonucleotide comprising a sequence identical to the 5' end of the target nucleic acid, a second oligonucleotide comprising a sequence identical to the 3' end of the target nucleic acid; and a plurality of oligonucleotides comprising a sequence identical to a different portion of a sequence of a target nucleic acid, each oligonucleotide having an overlapping sequence region corresponding to a sequence region in a next oligonucleotide, the oligonucleotides in the second pool together comprising the second target nucleic acid. In some embodiments, the second mixture is exposed to a ligase, thereby generating a second target nucleic acid. In some embodiments, the second oligonucleotide of the first pool comprises a restriction endonuclease recognition site for a restriction endonuclease and the first oligonucleotide of the second pool comprises a restriction endonuclease recognition site for the restriction endonuclease.

In some embodiments, the method further comprises assembling at least two target nucleic acids. In some embodiments, the step of assembling is by hierarchical assembly. In some embodiments, the at least two target nucleic acids are subjected to restriction endonuclease digestion and ligation thereby forming a long target nucleic acid construct. In some embodiments, the long target nucleic acid construct is at least about 10 kilobases in length or at least about 100 kilobases in length.

In some aspects, the invention relates to a composition for the assembly of a target nucleic acid having a predefined sequence, the composition comprising a plurality of oligonucleotides comprising a first oligonucleotide comprising a sequence identical to the 5' end of the target nucleic acid, a second oligonucleotide comprising a sequence identical to the 3' end of the target nucleic acid; and one or more oligonucleotides comprising a sequence identical to a different portion of a sequence of a target nucleic acid, each of the oligonucleotides having an overlapping sequence region corresponding to a sequence region in a next oligonucleotide, the plurality of oligonucleotides together comprising the target nucleic acid; a plurality of common sequences comprising a primer recognition site for a primer pair and a restriction endonuclease recognition site. In some embodiments, the composition further comprises a restriction endonuclease and/or a ligase. The restriction endonuclease can be a type IIS restriction endonuclease.

In some embodiments, the plurality of oligonucleotides can be amplified and/or error-corrected. In some embodiments, the composition can further comprise a linearized vector having a 5' compatible with the first oligonucleotide and a 3' end compatible with the second oligonucleotide.

BRIEF DESCRIPTION OF THE FIGURES

FIG. 5 illustrates the nucleotide sequence of plasmid pG9-1 (SEQ ID NO.: 1) with restriction endonuclease recognition sites (underlined).

DETAILED DESCRIPTION OF THE INVENTION

Figure 1:
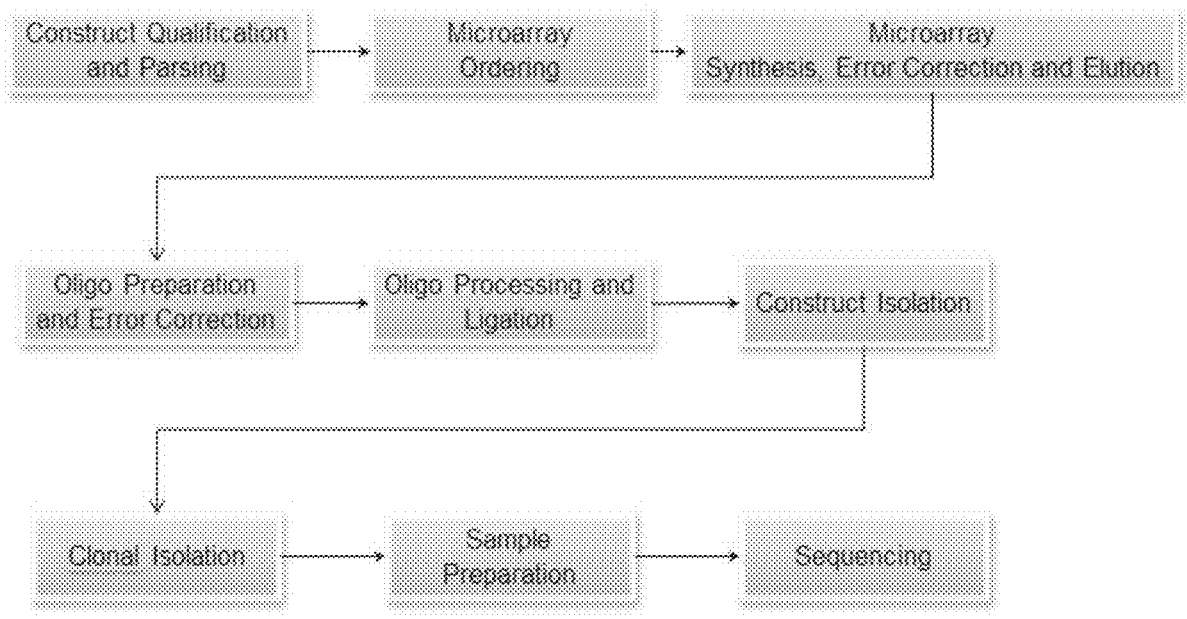
FIG. 1 illustrates an exemplary process for high fidelity nucleic acid assembly according to one embodiment of the invention.

Aspects of the invention may be useful for optimizing nucleic acid assembly reactions and to reduce the number of incorrectly assembled nucleic acids. The methods and composition of the invention can facilitate the process of obtaining a target sequence having a predefined sequence. Accordingly, the methods and composition of the invention may increase the probability of obtaining a correctly assembled nucleic acid and thereby reduce the cost and time associated with the production of a nucleic acid having a predetermined sequence.

Aspects of the invention may be used to improve the yield of one or more initial or intermediate assembly reactions. In some embodiments, the methods and compositions of the invention can improve the efficiency of the overall assembly procedure by avoiding the requirement to separate a number of assembly steps, such as for example, enzymatic digestion, purification and ligation steps. Accordingly, some aspects of the invention allows for predictable and/or reliable assembly strategies and can significantly decrease the time and steps needed for gene synthesis and increase the yield and/or accuracy of intermediate product or final nucleic acid products.

In some aspects of the invention, the assembly process comprises designing and implementing nucleic acid assembly strategies that can accommodate sequence features known or predicted to interfere with one or more assembly steps. For example, the nucleic acid sequence to be synthesized can be analyzed for sequence features, such as repeated sequences, sequences having a significantly high or low GC content, and/or other sequences associated with secondary structures, that can interfere with one or more assembly steps. One of skill in the art will understand that certain sequence features may interfere with multiplex assembly reactions (e.g. polymerase-based extension reactions) and/or promote the formation of unwanted assembly products thereby reducing or preventing the assembly of correct nucleic acid products. In some embodiments, if a plurality of interfering sequence features is identified in a target nucleic acid sequence, a useful strategy may involve separating the interfering sequence features during assembly. For example, a target nucleic acid may be assembled in a process involving a plurality of intermediate fragments or building blocks that are designed to contain only a small number of interfering sequences (e.g., 0, 1, 2, or 3). In some embodiments, each intermediate fragment or building block may contain at most one interfering sequence feature. Accordingly, each intermediate fragment may be assembled efficiently. In some embodiments, the design of the nucleic acids fragments or building blocks may exclude interfering sequence features from their 5' and/or 3' ends. Accordingly, the interfering sequence features may be excluded from complementary overlapping regions between adjacent starting nucleic acids that are designed for use assembly reaction. This may prevent or reduce interference with sequence-specific hybridization reactions that are important for correct assembly of the nucleic acids. In some embodiments, it may be sufficient to exclude an interfering sequence feature from the immediate 3' and/or 5' end of a building block. For example, an interfering sequence feature may be located at least one nucleotide in from a 3' end and/or 5' end, and preferably 2, 3, 4, 5, or more nucleotides (e.g., 5-10, 10-15, 15-20, or more nucleotides) in from a 3' end and/or 5' end of a building block.

Aspects of the invention may be used in conjunction with in vitro and/or in vivo nucleic acid assembly procedures.

Aspects of the methods and compositions provided herein are useful for increasing the accuracy, yield, throughput, and/or cost efficiency of nucleic acid synthesis and assembly reactions. As used herein the terms "nucleic acid", "polynucleotide", "oligonucleotide" are used interchangeably and refer to naturally-occurring or synthetic polymeric forms of nucleotides. The oligonucleotides and nucleic acid molecules of the present invention may be formed from naturally occurring nucleotides, for example forming deoxyribonucleic acid (DNA) or ribonucleic acid (RNA) molecules. Alternatively, the naturally occurring oligonucleotides may include structural modifications to alter their properties, such as in peptide nucleic acids (PNA) or in locked nucleic acids (LNA). The solid phase synthesis of oligonucleotides and nucleic acid molecules with naturally occurring or artificial bases is well known in the art. The terms should be understood to include equivalents, analogs of either RNA or DNA made from nucleotide analogs and as applicable to the embodiment being described, single-stranded or double-stranded polynucleotides. Nucleotides useful in the invention include, for example, naturally-occurring nucleotides (for example, ribonucleotides or deoxyribonucleotides), or natural or synthetic modifications of nucleotides, or artificial bases. As used herein, the term monomer refers to a member of a set of small molecules which are and can be joined together to from an oligomer, a polymer or a compound composed of two or more members. The particular ordering of monomers within a polymer is referred to herein as the "sequence" of the polymer. The set of monomers includes but is not limited to example, the set of common L-amino acids, the set of D-amino acids, the set of synthetic and/or natural amino acids, the set of nucleotides and the set of pentoses and hexoses. Aspects of the invention described herein primarily with regard to the preparation of oligonucleotides, but could readily be applied in the preparation of other polymers such as peptides or polypeptides, polysaccharides, phospholipids, heteropolymers, polyesters, polycarbonates, polyureas, polyamides, polyethyleneimines, polyarylene sulfides, polysiloxanes, polyimides, polyacetates, or any other polymers.

Target Nucleic Acids

As used herein, the term "predetermined sequence" means that the sequence of the polymer is known and chosen before synthesis or assembly of the polymer. In particular, aspects of the invention is described herein primarily with regard to the preparation of nucleic acids molecules, the sequence of the oligonucleotide or polynucleotide being known and chosen before the synthesis or assembly of the nucleic acid molecules. In some embodiments of the technology provided herein, immobilized oligonucleotides or polynucleotides are used as a source of material. In various embodiments, the methods described herein use pluralities of oligonucleotides, each sequence being determined based on the sequence of the final polynucleotides constructs to be synthesized. In one embodiment, oligonucleotides are short nucleic acid molecules. For example, oligonucleotides may be from 10 to about 300 nucleotides, from 20 to about 400 nucleotides, from 30 to about 500 nucleotides, from 40 to about 600 nucleotides, or more than about 600 nucleotides long. However, shorter or longer oligonucleotides may be used. Oligonucleotides may be designed to have different length. In some embodiments, the sequence of the polynucleotide construct may be divided up into a plurality of shorter sequences that can be synthesized in parallel and assembled into a single or a plurality of desired polynucleotide constructs using the methods described herein.

In some embodiments, a target nucleic acid may have a sequence of a naturally occurring gene and/or other naturally occurring nucleic acid (e.g., a naturally occurring coding sequence, regulatory sequence, non-coding sequence, chromosomal structural sequence such as a telomere or centromere sequence, etc., any fragment thereof or any combination of two or more thereof) or a sequence that is not naturally-occurring. In some embodiments, a target nucleic acid may be designed to have a sequence that differs from a natural sequence at one or more positions. In other embodiments, a target nucleic acid may be designed to have an entirely novel sequence. However, it should be appreciated that target nucleic acids may include one or more naturally occurring sequences, non-naturally occurring sequences, or combinations thereof.

In some embodiments, methods of assembling libraries containing nucleic acids having predetermined sequence variations are provided herein. Assembly strategies provided herein can be used to generate very large libraries representative of many different nucleic acid sequences of interest. For example, the methods provided herein can be used to assemble libraries having more than 10 different sequence variants. In some embodiments, libraries of nucleic acid are libraries of sequence variants. Sequence variants may be variants of a single naturally-occurring protein encoding sequence. However, in some embodiments, sequence variants may be variants of a plurality of different protein-encoding sequences. Accordingly, one aspect of the invention provided herein relates to the design of assembly strategies for preparing precise high-density nucleic acid libraries. Another aspect of the technology provided herein relates to assembling precise high-density nucleic acid libraries. Aspects of the technology provided herein also provide precise high-density nucleic acid libraries. A high-density nucleic acid library may include more that 100 different sequence variants (e.g., about $10^2$ to $10^3$; about $10^3$ to $10^4$; about $10^4$ to $10^5$; about $10^5$ to $10^6$; about $10^6$ to $10^7$; about $10^7$ to $10^8$; about $10^8$ to $10^9$; about $10^9$ to $10^{10}$; about $10^{10}$ to $10^{11}$; about $10^{11}$ to $10^{12}$; about $10^{12}$ to $10^{13}$; about $10^{13}$ to $10^{14}$; about $10^{14}$ to $10^{15}$; or more different sequences) wherein a high percentage of the different sequences are specified sequences as opposed to random sequences (e.g., more than about 50%, more than about 60%, more than about 70%, more than about 75%, more than about 80%, more than about 85%, more than about 90%, about 91%, about 92%, about 93%, about 94%, about 95%, about 96%, about 97%, about 98%, about 99%, or more of the sequences are predetermined sequences of interest).

In certain embodiments, a target nucleic acid may include a functional sequence (e.g., a protein binding sequence, a regulatory sequence, a sequence encoding a functional protein, etc., or any combination thereof). However, in some embodiments the target nucleic acid may lack a specific functional sequence (e.g., a target nucleic acid may include only non-functional fragments or variants of a protein binding sequence, regulatory sequence, or protein encoding sequence, or any other non-functional naturally-occurring or synthetic sequence, or any non-functional combination thereof). Certain target nucleic acids may include both functional and non-functional sequences. These and other aspects of target nucleic acids and their uses are described in more detail herein.

A target nucleic acid may, in some embodiments, be assembled in a single multiplex assembly reaction (e.g., a single oligonucleotide assembly reaction). However, a target nucleic acid may also be assembled from a plurality of nucleic acid fragments, each of which may have been generated in a separate multiplex oligonucleotide assembly reactions. It should be appreciated that one or more nucleic acid fragments generated via multiplex oligonucleotide assembly may, in some embodiments, be combined with one or more nucleic acid molecules obtained from another source (e.g., a restriction fragment, a nucleic acid amplification product, etc.) to form a target nucleic acid. In some embodiments, a target nucleic acid that is assembled in a first reaction may be used as an input nucleic acid fragment for a subsequent assembly reaction to produce a larger target nucleic acid. The terms "multiplex assembly" and "multiplex oligonucleotide assembly reaction" used herein generally refer to assembly reactions involving a plurality of starting nucleic acids (e.g., a plurality of at least partially overlapping nucleic acids) that are assembled to produce a larger final nucleic acid.

Assembly Process

FIG. 1 illustrates a process for assembling a nucleic acid in accordance with one embodiment of the invention. Initially, sequence information is obtained. The sequence information may be the sequence of a predetermined target nucleic acid that is to be assembled. In some embodiments, the sequence may be received in the form of an order from a customer. In some embodiments, the sequence may be received as a nucleic acid sequence (e.g., DNA or RNA). In some embodiments, the sequence may be received as a protein sequence. The sequence may be converted into a DNA sequence. For example, if the sequence obtained is an RNA sequence, the Us may be replaced with Ts to obtain the corresponding DNA sequence. If the sequence obtained is a protein sequence, the protein sequence may be converted into a DNA sequence using appropriate codons for the amino acids.

In some embodiments, the sequence information may be analyzed to determine an assembly strategy, such as the number and the sequences of the fragments (also referred herein as building blocks, oligonucleotides or intermediate fragments) to be assembled to generate the predefined sequence of the target nucleic acid. In some embodiments, the sequence analysis may involve scanning for the presence of one or more interfering sequence features that are known or predicted to interfere with oligonucleotide synthesis, amplification or assembly. For example, an interfering sequence structure may be a sequence that has a low GC content (e.g., less than 30% GC, less than 20% GC, less than 10% GC, etc.) over a length of at least 10 bases (e.g., 10-20, 20-50, 50-100, or more than 100 bases), or a sequence that may be forming secondary structures or stem-loop structures. Once passing this filter, the nucleic acid sequence can be divided into smaller pieces, such as oligonucleotide building blocks.

In some embodiments, after the construct qualification and parsing step, synthetic oligonucleotides for the assembly may be designed (e.g. sequence, size, and number). Synthetic oligonucleotides can be generated using standard DNA synthesis chemistry (e.g. phosphoramidite method). Synthetic oligonucleotides may be synthesized on a solid support, such as for example a microarray, using any appropriate technique known in the art or as described in more detail herein. Oligonucleotides can be eluted from the microarray prior to be subjected to amplification or can be amplified on the microarray. It should be appreciated that different oligonucleotides may be designed to have different lengths.

In some embodiments, the building blocks oligonucleotides for each target sequence can be amplified. For example, the oligonucleotides can be designed such as having at their 3' end and 5' end a primer binding sequence and the oligonucleotides can be amplified by polymerase chain reaction (PCR) using the appropriate primers pair(s).

It should be appreciated that synthetic oligonucleotides may have sequence errors. Accordingly, oligonucleotide preparations may be selected or screened to remove error-containing molecules as described in more detail herein. Error containing-oligonucleotides may be double-stranded homoduplexes having the error on both strands (i.e., incorrect complementary nucleotide(s), deletion(s), or addition(s) on both strands). In some embodiments, sequence errors may be removed using a technique that involves denaturing and reannealing the double-stranded nucleic acids. In some embodiments, single strands of nucleic acids that contain complementary errors may be unlikely to reanneal together if nucleic acids containing each individual error are present in the nucleic acid preparation at a lower frequency than nucleic acids having the correct sequence at the same position. Rather, error containing single strands may reanneal with a complementary strand that contains no errors or that contains one or more different errors. As a result, error-containing strands may end up in the form of heteroduplex molecules in the re-annealed reaction product. Nucleic acid strands that are error-free may reanneal with error-containing strands or with other error-free strands. Reannealed error-free strands form homoduplexes in the reannealed sample. Accordingly, by removing heteroduplex molecules from the re-annealed preparation of oligonucleotides, the amount or frequency of error containing nucleic acids may be reduced. Any suitable method known in the art for removing heteroduplex molecules may be used, including chromatography, electrophoresis, selective binding of heteroduplex molecules, etc. In some embodiments, mismatch binding proteins that selectively (e.g., specifically) bind to heteroduplex nucleic acid molecules may be used. In some embodiments, the mismatch binding protein may be used on double-stranded oligonucleotides or polynucleotides in solution or immobilized onto a support.

In some embodiments, the oligonucleotides containing errors are removed using a MutS filtration process, for example, using MutS, a MutS homolog, or a combination thereof. In *E. coli*, the MutS protein, which appears to function as a homodimer, serves as a mismatch recognition factor. In eukaryotes, at least three MutS Homolog (MSH) proteins have been identified; namely, MSH2, MSH3, and MSH6, and they form heterodimers. For example in the yeast, *Saccharomyces cerevisiae*, the MSH2-MSH6 complex (also known as MutS alpha) recognizes base mismatches and single nucleotide insertion/deletion loops, while the MSH2-MSH3 complex (also known as MutSbeta) recognizes insertions/deletions of up to 12-16 nucleotides, although they exert substantially redundant functions. A mismatch binding protein may be obtained from recombinant or natural sources. A mismatch binding protein may be heat-stable. In some embodiments, a thermostable mismatch binding protein from a thermophilic organism may be used. Examples of thermostable DNA mismatch binding proteins include, but are not limited to: Tth MutS (from *Thermus thermophilus*), Taq MutS (from *Thermus aquaticus*), Apy MutS (from *Aquifex pyrophilus*), Tma MutS (from *Thermo-*

*toga maritima*), homologs thereof any other suitable MutS or any combination of two or more thereof.

It has been shown that MutS obtained from different species can have different affinity for a specific mismatch or for different mismatch. In some embodiments, a combination of different MutS having different affinities for different mismatch can be used.

In some embodiments, an enzyme complex using one or more repair proteins can be used. Examples of repair proteins include, but are not limited to, MutS, for mismatch recognition, MutH, for introduction of a nick in the target strand, and MutL, for mediating the interactions between MutH and MutS, homologs thereof or any combinations thereof. In some embodiments, the mismatch binding protein complex is a MutHLS enzyme complex.

In some embodiments, a sliding clamp technique may be used for enriching error-free double stranded oligonucleotides. In some embodiments, MutS or homolog thereof can interact with a DNA clamp protein. Examples of DNA clamp proteins include, but are not limited to, the bacterial sliding clamp protein DnaN, encoded by dnaN gene, which can function as a homodimer. In some embodiments, interaction of MutS protein, or homolog thereof, with a clamp protein can increase the effectiveness of MutS in binding mismatches.

In some embodiments, the oligonucleotides containing errors can be removed using an enzyme from the S1 family of proteins, for example CELI, CELII or a homolog thereof, such as RESI, or a combination thereof. Enzymes from the S1 family of proteins can recognize base mismatches, insertion and deletion loops. In some embodiments, such enzymes can bind preferentially to Holliday junctions after which the recognition site is cleaved, either through only one or both DNA strands. In some embodiments, a thermostable equivalent of a S1 protein may be used.

In some embodiments, the oligonucleotides containing errors can be removed using a small molecule, chemical or inorganic material that binds to mismatched base sites. At the mismatched site, nucleotide bases are extra-helical and can be susceptible to chemical modification reactions. Materials such permanganate, hydroxylamine, lysine, and or pentaamine ruthenium can be employed in the chemical cleavage method to modify the mismatched thymine and cytosine respectively. The resulting modified DNA can then treated with piperidine to cause a cleavage at the abasic sites. In some embodiments, specificity of cleavage can be monitored using divalent salt.

In some embodiments, in a next step, the error-corrected oligonucleotides are combined through the sequential removal of common sequences and subsequent ligation into longer, multi-oligonucleotide constructs.

In some aspects of the invention, the enzymatic digestion common sequence removal step is combined with a ligation step. One of skill in the art will appreciate that the process of the invention allows for a concurrent removal of common sequences and ligation into the target nucleic acid constructs and negate the need of enzymatic removal, bead-based capture and ligation sequential steps. In addition, one of skill in the art will appreciate that the process of the invention may present a number of advantages over the standard gene assembly process such as:

(1) Increase of the yield efficiency. Using the standard separate enzymatic removal of common sequences, the reaction is stopped after a set time point, with unreacted substrates or undigested oligonucleotides, still present which are the subject of further removal. One of skill in the art will understand that because the ligation reaction creates a desired product which is not a substrate for the enzymatic removal, the combination of the removal and ligation steps has the effect of driving the reaction toward the desired product irreversibly.

(2) Cost efficiency: The methods according to some aspects of the invention are cost efficient since there is no longer a need for the purification steps between the removal of common sequences and the ligation. Because of the elimination of purification steps, aspects of the present method also eliminate the need for biotin-labeled primers. There may be also an associated savings in the form of the reduced lead time for receipt of non-biotinylated primers over their biotin-containing counterparts.

(3) Time efficiency: The time and the number of steps needed for gene synthesis are reduced by removing the purification steps between enzymatic common sequence removal and ligation.

(4) Opportunities to add other sequences easily, without regard for their sizes. Because part of the purification step to remove undesired sequences is based on size, eliminating the purification can remove the size constraint for any additional sequences to be added for the gene synthesis. This can include a one-step ligation into a vector, or addition of common flanking sequences.

(5) The process allows for use of restriction sites in the gene which are used in the gene synthesis process itself. In previous methodologies, these restriction sites could not be used because cut sites would result in small DNA pieces which would be removed in the purification step. Enabling the usage of these restriction sites can allow for recursive (hierarchical) gene synthesis to build longer nucleic acids.

One of skill in the art would appreciate that after oligonucleotide assembly, the assembly products (e.g. final target nucleic acid or intermediate nucleic acid fragment) may contain sequences containing undesired sequences. The errors may result from sequences errors introduced during oligonucleotide synthesis or during the assembly of oligonucleotides into longer nucleic acids. In some embodiments, nucleic acids having the correct predefined sequence can be isolated from other nucleic acids sequences (also referred herein as preparative in vitro cloning). In some embodiments, the correct sequence may be isolated by selectively isolating the correct sequence from the other incorrect sequences. For example, nucleic acids having correct sequence can be selectively moved or transferred to a different feature of the support, or to another plate. Alternatively, nucleic acids having an incorrect sequence can be selectively removed from the feature comprising the nucleic acids of interest (see for example, PCT/US2007/01886, which is incorporated by reference herein in its entirety).

In some embodiments, after oligonucleotide processing and ligation, the assembly constructs or a copy of the assembled constructs can be isolated by clonal isolation. The assembly constructs can be sequence verified using, for example, high throughput sequencing. In some embodiments, sequence determination of the target nucleic acid sequences can be performed using sequencing of individual molecules, such as single molecule sequencing, or sequencing of an amplified population of target nucleic acid sequences, such as polony sequencing. Any suitable methods for sequencing, such as sequencing by hybridization, sequencing by ligation or sequencing by synthesis may be used.

Some aspects of the invention relate to a gene synthesis platform using methods described herein. In some embodiments, the gene synthesis platform can be combined with a next generation sequencing platform (e.g. sequencing by hybridization, sequencing by synthesis, sequencing by ligation or any other suitable sequencing method).

In some embodiments, the assembly procedure may include several parallel and/or sequential reaction steps in which a plurality of different nucleic acids or oligonucleotides are synthesized or immobilized, amplified, and are combined in order to be assembled (e.g., by extension or by ligation as described herein) to generate a longer nucleic acid product to be used for further assembly, cloning, or other applications (see PCT application PCT/US09/55267 which is incorporate herein by reference in its entirety).

Oligonucleotides Synthesis

In some embodiments, the methods and apparatus provided herein use oligonucleotides that are immobilized on a surface or substrate (e.g., support-bound oligonucleotides). As used herein the term "support" and "substrate" are used interchangeably and refers to a porous or non-porous solvent insoluble material on which polymers such as nucleic acids are synthesized or immobilized. As used herein "porous" means that the material contains pores having substantially uniform diameters (for example in the nm range). Porous materials include paper, synthetic filters etc. In such porous materials, the reaction may take place within the pores. The support can have any one of a number of shapes, such as pin, strip, plate, disk, rod, bends, cylindrical structure, particle, including bead, nanoparticles and the like. The support can have variable widths. The support can be hydrophilic or capable of being rendered hydrophilic and includes inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, polyethylene, polypropylene, poly (4-methylbutene), polystyrene, polymethacrylate, poly(ethylene terephthalate), nylon, poly(vinyl butyrate), polyvinylidene difluoride (PVDF) membrane, glass, controlled pore glass, magnetic controlled pore glass, ceramics, metals, and the like etc.; either used by themselves or in conjunction with other materials. In some embodiments, oligonucleotides are synthesized on an array format. For example, single-stranded oligonucleotides are synthesized in situ on a common support wherein each oligonucleotide is synthesized on a separate or discrete feature (or spot) on the substrate. In preferred embodiments, single stranded oligonucleotides are bound to the surface of the support or feature. As used herein the term "array" refers to an arrangement of discrete features for storing, routing, amplifying and releasing oligonucleotides or complementary oligonucleotides for further reactions. In a preferred embodiment, the support or array is addressable: the support includes two or more discrete addressable features at a particular predetermined location (i.e., an "address") on the support. Therefore, each oligonucleotide molecule of the array is localized to a known and defined location on the support. The sequence of each oligonucleotide can be determined from its position on the support.

In some embodiments, oligonucleotides are attached, spotted, immobilized, surface-bound, supported or synthesized on the discrete features of the surface or array. Oligonucleotides may be covalently attached to the surface or deposited on the surface. Arrays may be constructed, custom ordered or purchased from a commercial vendor (e.g., Agilent, Affymetrix, Nimblegen). Various methods of construction are well known in the art e.g., maskless array synthesizers, light directed methods utilizing masks, flow channel methods, spotting methods etc. In some embodiments, construction and/or selection oligonucleotides may be synthesized on a solid support using maskless array synthesizer (MAS). Maskless array synthesizers are described, for example, in PCT application No. WO 99/42813 and in corresponding U.S. Pat. No. 6,375,903. Other examples are known of maskless instruments which can fabricate a custom DNA microarray in which each of the features in the array has a single-stranded DNA molecule of desired sequence. Other methods for synthesizing construction and/or selection oligonucleotides include, for example, light-directed methods utilizing masks, flow channel methods, spotting methods, pin-based methods, and methods utilizing multiple supports. Light directed methods utilizing masks (e.g., VLSIPS™ methods) for the synthesis of oligonucleotides is described, for example, in U.S. Pat. Nos. 5,143,854, 5,510,270 and 5,527,681. These methods involve activating predefined regions of a solid support and then contacting the support with a preselected monomer solution. Selected regions can be activated by irradiation with a light source through a mask much in the manner of photolithography techniques used in integrated circuit fabrication. Other regions of the support remain inactive because illumination is blocked by the mask and they remain chemically protected. Thus, a light pattern defines which regions of the support react with a given monomer. By repeatedly activating different sets of predefined regions and contacting different monomer solutions with the support, a diverse array of polymers is produced on the support. Other steps, such as washing unreacted monomer solution from the support, can be optionally used. Other applicable methods include mechanical techniques such as those described in U.S. Pat. No. 5,384,261. Additional methods applicable to synthesis of construction and/or selection oligonucleotides on a single support are described, for example, in U.S. Pat. No. 5,384, 261. For example, reagents may be delivered to the support by either (1) flowing within a channel defined on predefined regions or (2) "spotting" on predefined regions. Other approaches, as well as combinations of spotting and flowing, may be employed as well. In each instance, certain activated regions of the support are mechanically separated from other regions when the monomer solutions are delivered to the various reaction sites. Flow channel methods involve, for example, microfluidic systems to control synthesis of oligonucleotides on a solid support. For example, diverse polymer sequences may be synthesized at selected regions of a solid support by forming flow channels on a surface of the support through which appropriate reagents flow or in which appropriate reagents are placed. Spotting methods for preparation of oligonucleotides on a solid support involve delivering reactants in relatively small quantities by directly depositing them in selected regions. In some steps, the entire support surface can be sprayed or otherwise coated with a solution, if it is more efficient to do so. Precisely measured aliquots of monomer solutions may be deposited dropwise by a dispenser that moves from region to region. Pin-based methods for synthesis of oligonucleotides on a solid support are described, for example, in U.S. Pat. No. 5,288,514. Pin-based methods utilize a support having a plurality of pins or other extensions. The pins are each inserted simultaneously into individual reagent containers in a tray. An array of 96 pins is commonly utilized with a 96-container tray, such as a 96-well microtiter dish. Each tray is filled with a particular reagent for coupling in a particular chemical reaction on an individual pin. Accordingly, the trays will often contain different reagents. Since the chemical reactions have been optimized such that each of the reactions can be performed under a relatively similar set of reaction conditions, it becomes possible to conduct multiple chemical coupling steps simultaneously.

In another embodiment, a plurality of oligonucleotides may be synthesized on multiple supports. One example is a bead based synthesis method which is described, for example, in U.S. Pat. Nos. 5,770,358; 5,639,603; and 5,541,061. For the synthesis of molecules such as oligonucleotides on beads, a large plurality of beads is suspended in a suitable carrier (such as water) in a container. The beads are provided with optional spacer molecules having an active site to which is complexed, optionally, a protecting group. At each step of the synthesis, the beads are divided for coupling into a plurality of containers. After the nascent oligonucleotide chains are deprotected, a different monomer solution is added to each container, so that on all beads in a given container, the same nucleotide addition reaction occurs. The beads are then washed of excess reagents, pooled in a single container, mixed and re-distributed into another plurality of containers in preparation for the next round of synthesis. It should be noted that by virtue of the large number of beads utilized at the outset, there will similarly be a large number of beads randomly dispersed in the container, each having a unique oligonucleotide sequence synthesized on a surface thereof after numerous rounds of randomized addition of bases. An individual bead may be tagged with a sequence which is unique to the double-stranded oligonucleotide thereon, to allow for identification during use.

Pre-synthesized oligonucleotide and/or polynucleotide sequences may be attached to a support or synthesized in situ using light-directed methods, flow channel and spotting methods, inkjet methods, pin-based methods and bead-based methods set forth in the following references: McGall et al. (1996) Proc. Natl. Acad. Sci. U.S.A. 93:13555: Synthetic DNA Arrays In Genetic Engineering, Vol. 20:111, Plenum Press (1998); Duggan et al. (1999) Nat. Genet. S21:10; Microarrays: Making Them and Using Them In Microaray Bioinformatics, Cambridge University Press, 2003; U.S. Patent Application Publication Nos. 2003/0068633 and 2002/0081582; U.S. Pat. Nos. 6,833,450, 6,830,890, 6,824,866, 6,800,439, 6,375,903 and 5,700,637; and PCT Publication Nos. WO 04/031399, WO 04/031351, WO 04/029586, WO 03/100012, WO 03/066212, WO 03/065038, WO 03/064699, WO 03/064027, WO 03/064026, WO 03/046223, WO 03/040410 and WO 02/24597; the disclosures of which are incorporated herein by reference in their entirety for all purposes. In some embodiments, pre-synthesized oligonucleotides are attached to a support or are synthesized using a spotting methodology wherein monomers solutions are deposited dropwise by a dispenser that moves from region to region (e.g., ink jet). In some embodiments, oligonucleotides are spotted on a support using, for example, a mechanical wave actuated dispenser.

Amplification

In some embodiments, oligonucleotides may be amplified using an appropriate primer pair with one primer corresponding to each end of the oligonucleotide (e.g., one that is complementary to the 3' end of the oligonucleotide and one that is identical to the 5' end of the oligonucleotide). In some embodiments, an oligonucleotide may be designed to contain a central or internal assembly sequence (corresponding to a target sequence, designed to be incorporated into the final product) flanked by a 5' amplification sequence (e.g., a 5' universal sequence or 5' common amplification sequence) and a 3' amplification sequence (e.g., a 3' universal sequence or 5' common amplification sequence).

In some embodiments, a synthetic oligonucleotide may include a central assembly sequence flanked by 5' and 3' amplification sequences. The central assembly sequence is designed for incorporation into an assembled nucleic acid. The flanking sequences are designed for amplification and are not intended to be incorporated into the assembled nucleic acid. The flanking amplification sequences may be used as primer sequences to amplify a plurality of different assembly oligonucleotides that share the same amplification sequences but have different central assembly sequences. In some embodiments, the flanking sequences are removed after amplification to produce an oligonucleotide that contains only the assembly sequence.

Amplification primers (e.g., between 10 and 50 nucleotides long, between 15 and 45 nucleotides long, about 25 nucleotides long, etc.) corresponding to the flanking amplification sequences may be used to amplify the oligonucleotides (e.g., one primer may be complementary to the 3' amplification sequence and one primer may have the same sequence as the 5' amplification sequence). In some embodiments, a plurality of different oligonucleotides (e.g., about 5, 10, 50, 100, or more) with different central assembly sequences may have identical 5' amplification sequences and identical 3' amplification sequences. These oligonucleotides can all be amplified in the same reaction using the same amplification primers. The amplification sequences may then be removed from the amplified oligonucleotides using any suitable technique to produce oligonucleotides that contain only the assembly sequences. In some embodiments, the amplification sequences are removed by a restriction enzyme as described in more details herein.

In some embodiments, the oligonucleotides may be amplified while still attached to the support. In some embodiments, the oligonucleotides may be removed or cleaved from the support prior to amplification.

In some embodiments, the method includes synthesizing a plurality of oligonucleotides or polynucleotides in a chain extension reaction using a first plurality of single stranded oligonucleotides as templates. As noted above, the oligonucleotides may be first synthesized onto a plurality of discrete features of the surface, or may be deposited on the plurality of features of the support. In some embodiments, the oligonucleotides are covalently attached to the support. In some embodiments, the first plurality of oligonucleotides is immobilized to a solid surface. In some embodiments, each feature of the solid surface comprises a high density of oligonucleotides having a different predetermined sequence (e.g., approximately $10^6$-$10^8$ molecules per feature). The support may comprise at least 100, at least 1,000, at least $10^4$, at least $10^5$, at least $10^6$, at least $10^7$, at least $10^8$ features. In some embodiments, after amplification, the double-stranded oligonucleotides may be eluted in solution and/or subjected to error reduction and/or assembly to form longer nucleic acid constructs.

Error Reduction

In some embodiments, each fragment is assembled and fidelity optimized to remove error containing nucleic acids (e.g., using one or more post-assembly fidelity optimization techniques described herein) before being processed to generated cohesive ends. A sequence error may include one or more nucleotide deletions, additions, substitutions (e.g., transversion or transition), inversions, duplications, or any combination of two or more thereof oligonucleotide errors may be generated during oligonucleotide synthesis. Different synthetic techniques may be prone to different error profiles and frequencies. In some embodiments, error rates may vary from 1/10 to 1/200 errors per base depending on the synthesis protocol that is used. However, in some embodiments, lower error rates may be achieved. Also, the types of errors may depend on the synthetic techniques that are used. For example, microarray-based oligonucleotide synthesis may result in relatively more deletions than column-based synthetic techniques.

Some aspects of the invention relate to a polynucleotide assembly process wherein synthetic oligonucleotides are designed and used to assemble polynucleotides into longer polynucleotides constructs. During enzymatic amplification or chain extension reactions, the error in sequence is faithfully replicated. As a result, polynucleotides population synthesized by this method contains both error-free and error-prone sequences. In some embodiments, since synthetic oligonucleotides can contain incorrect sequences due to errors introduced during oligonucleotide synthesis, it can be useful to remove polynucleotide that have incorporated one or more error-containing oligonucleotides during assembly or extension. In some embodiments, one or more assembled polynucleotides may be sequenced to determine whether they contain the predetermined sequence or not. This procedure allows fragments with the correct sequence to be identified. In other embodiments, other techniques may be used to remove error containing nucleic acid fragments. Such nucleic acid fragments can be nascently synthesized oligonucleotides or assembled nucleic acid polymers. It should be appreciated that error containing-nucleic acids can be double-stranded homoduplexes having the error on both strands (i.e., incorrect complementary nucleotide(s), deletion(s), or addition(s) on both strands), because the assembly procedure may involve one or more rounds of polymerase extension (e.g., during assembly or after assembly to amplify the assembled product). During polymerase extension, the input nucleic acid containing an error may serve as a template thereby producing a complementary strand comprising the complementary error. In certain embodiments, a preparation of double-stranded nucleic acid fragments or duplexes may be suspected to contain a mixture of nucleic acids having the correct predefined sequence as well as nucleic acids containing one or more sequence errors incorporated during assembly. The term "duplex" refers to a nucleic acid molecule that is at least partially double-stranded. A "stable duplex" refers to a duplex that is relatively more likely to remain hybridized to a complementary sequence under a given set of hybridization conditions. In an exemplary embodiment, a stable duplex refers to a duplex that does not contain a basepair mismatch, insertion, or deletion. An "unstable duplex" refers to a duplex that is relatively less likely to remain hybridized to a complementary sequence under a given set of hybridization conditions such as stringent melt. In an exemplary embodiment, an unstable duplex refers to a duplex that contains at least one base-pair mismatch, insertion, or deletion. As used herein the term "stringency" is used in reference to the conditions of temperature, ionic strength, and the presence of other compounds such as organic solvents, under which nucleic acid hybridizations are conducted. Hybridization stringency increases with temperature and/or the solution chemical properties such as the amounts of salts and/or formamide in the hybridization solution during a hybridization process. With "high stringency" conditions, nucleic acid base pairing will occur only between nucleic acid fragments that have a high frequency of complementary base sequences. Stringent conditions may be selected to be about 5° C. lower than the thermal melting point (Tm) for a given polynucleotide duplex at a defined ionic strength and pH. The length of the complementary polynucleotide strands and the GC content determine the Tm of the duplex, and thus the hybridization conditions necessary for obtaining a desired specificity of hybridization. The Tm is the temperature (under defined ionic strength and pH) at which 50% of a polynucleotide sequence hybridizes to a perfectly matched complementary strand. In certain cases it may be desirable to increase the stringency of the hybridization conditions to be about equal to the Tm for a particular duplex. Appropriate stringency conditions are known to those skilled in the art or may be determined experimentally by the skilled artisan. See, for example, Current Protocols in Molecular Biology, John Wiley & Sons, N.Y. (1989), 6.3.1-12.3.6; Sambrook et al., 1989, Molecular Cloning, A Laboratory Manual, Cold Spring Harbor Press, N.Y; S. Agrawal (ed.) Methods in Molecular Biology, volume 20; Tijssen (1993) Laboratory Techniques in biochemistry and molecular biology-hybridization with nucleic acid probes, e.g., part I chapter 2 "Overview of principles of hybridization and the strategy of nucleic acid probe assays", Elsevier, New York.

In some embodiments, sequence errors may be removed using a technique that involves denaturing and reannealing the double-stranded nucleic acids. In some embodiments, single strands of nucleic acids that contain complementary errors may be unlikely to reanneal together if nucleic acids containing each individual error are present in the nucleic acid preparation at a lower frequency than nucleic acids having the correct sequence at the same position. Rather, error containing single strands can reanneal with error-free complementary strand or complementary strands containing one or more different errors or error at different location. As a result, error-containing strands can end up in the form of heteroduplex molecules in the reannealed reaction product. Nucleic acid strands that are error-free may reanneal with error-containing strands or with other error-free strands. Reannealed error-free strands form homoduplexes in the reannealed sample. Accordingly, by removing heteroduplex molecules from the reannealed preparation of nucleic acid fragments, the amount or frequency of error containing nucleic acids can be reduced.

Heteroduplex formation thus takes place through a process that can be understood as shuffling, by which nucleic acid strands from different populations can be hybridized with one another so that perfect match and mismatch-containing duplexes can be formed. Suitable method for removing heteroduplex molecules include chromatography, electrophoresis, selective binding of heteroduplex molecules that binds preferentially to double stranded DNA having a sequence mismatch between the two strands. The term "mismatch" or "base pair mismatch" indicates a base pair combination that generally does not form in nucleic acids according to Watson and Crick base pairing rules. For example, when dealing with the bases commonly found in DNA, namely adenine, guanine, cytosine and thymidine, base pair mismatches are those base combinations other than the A-T and G-C pairs normally found in DNA. As described herein, a mismatch may be indicated, for example as C/C meaning that a cytosine residue is found opposite another cytosine, as opposed to the proper pairing partner, guanine.

In some embodiments, oligonucleotide preparations may be selected or screened to remove error-containing molecules as described in more detail herein. In some embodiments, oligonucleotides can be error-corrected using a mismatch-binding agent as described herein.

In one aspect, the invention relates to a method for producing high fidelity polynucleotides on a solid support.

The synthetic polynucleotides are at least about 1, 2, 3, 4, 5, 8, 10, 15, 20, 25, 30, 40, 50, 75, or 100 kilobases (kb), or 1 megabase (mb), or longer. In exemplary embodiments, a compositions of synthetic polynucleotides contains at least about 1%, 2%, 3%, 4%, 5%, 6%, 7%, 8%, 9%, 10%, 15%, 20%, 25%, 50%, 60%, 70%, 80%, 90%, 95% or more, copies that are error free (e.g., having a sequence that does not deviate from a predetermined sequence). The percent of error free copies is based on the number of error free copies in the compositions as compared to the total number of copies of the polynucleotide in the composition that were intended to have the correct, e.g., predefined or predetermined, sequence.

Some aspects the invention relate to the design of oligonucleotides for high fidelity polynucleotide assembly. Aspects of the invention may be useful to increase the throughput rate of a nucleic acid assembly procedure and/or reduce the number of steps or amounts of reagent used to generate a correctly assembled nucleic acid. In certain embodiments, aspects of the invention may be useful in the context of automated nucleic acid assembly to reduce the time, number of steps, amount of reagents, and other factors required for the assembly of each correct nucleic acid. Accordingly, these and other aspects of the invention may be useful to reduce the cost and time of one or more nucleic acid assembly procedures.

Single-Stranded Overhangs

In some aspects of the invention, nucleic acid fragments being assembled are designed to have overlapping complementary sequences. In some embodiments, the nucleic acid fragments are double-stranded DNA fragments with 3' and/or 5' single-stranded overhangs. These overhangs may be cohesive ends that can anneal to complementary cohesive ends on different nucleic acid fragments. According to aspects of the invention, the presence of complementary sequences (and particularly complementary cohesive ends) on two nucleic acid fragments promotes their covalent assembly. In some embodiments, a plurality of nucleic acid fragments with different overlapping complementary single-stranded cohesive ends can be assembled and their order in the assembled nucleic acid product can be determined by the identity of the cohesive ends on each fragment. For example, the nucleic acid fragments may be designed so that a first nucleic acid has a first cohesive end that is complementary to a first cohesive end of the vector and a second cohesive end that is complementary to a first cohesive end of a second nucleic acid. The second cohesive end of the second nucleic acid may be complementary to a first cohesive end of a third nucleic acid. The second cohesive end of the third nucleic acid may be complementary a first cohesive end of a fourth nucleic acid. And so on through to the final nucleic acid that has a first cohesive end that may be complementary to a second cohesive end on the penultimate nucleic acid.

In certain embodiments, the overlapping complementary regions between adjacent nucleic acid fragments are designed (or selected) to be sufficiently different to promote (e.g., thermodynamically favor) assembly of a unique alignment of nucleic acid fragments (e.g., a selected or designed alignment of fragments). It should be appreciated that overlapping regions of different length may be used. In some embodiments, longer cohesive ends may be used when higher numbers of nucleic acid fragments are being assembled. Longer cohesive ends may provide more flexibility to design or select sufficiently distinct sequences to discriminate between correct cohesive end annealing (e.g., involving cohesive ends designed to anneal to each other) and incorrect cohesive end annealing (e.g., between non-complementary cohesive ends).

In some embodiments, two or more pairs of complementary cohesive ends between different nucleic acid fragments may be designed or selected to have identical or similar sequences in order to promote the assembly of products containing a relatively random arrangement (and/or number) of the fragments that have similar or identical cohesive ends. This may be useful to generate libraries of nucleic acid products with different sequence arrangements and/or different copy numbers of certain internal sequence regions.

In some embodiments, the second cohesive end of the final nucleic acid may be complementary to a second cohesive end of the vector. According to aspects of the invention, this method may be used to generate a vector containing nucleic acid fragments assembled in a predetermined linear order (e.g., first, second, third, fourth, . . . , final). In some embodiments, each of the two terminal nucleic acid fragments (e.g., the terminal fragment at each end of an assembled product) may be designed to have a cohesive end that is complementary to a cohesive end on a vector (e.g., on a linearized vector). These cohesive ends may be identical cohesive ends that can anneal to identical complementary terminal sequences on a linearized vector. However, in some embodiments, the cohesive ends on the terminal fragments are different and the vector contains two different cohesive ends, one at each end of a linearized vector, each complementary to one of the terminal fragment cohesive ends. Accordingly, the vector may be a linearized plasmid that has two cohesive ends, each of which is complementary with one end of the assembled nucleic acid fragments.

Some aspects of the invention involve double-stranded nucleic acids with single-stranded overhangs. Overhangs may be generated using any suitable technique. In some embodiments, a double-stranded nucleic acid fragment (e.g., a fragment assembled in a multiplex assembly) may be digested with an appropriate restriction enzyme to generate a terminal single-stranded overhang. In some embodiments, fragments that are designed to be adjacent to each other in an assembled product may be digested with the same enzyme to expose complementary overhangs. In some embodiments, overhangs may be generated using a type IIS restriction enzyme. Type IIS restriction enzymes are enzymes that bind to a double stranded nucleic acid at one site, referred to as the recognition site, and make a single double stranded cut outside of the recognition site. The double stranded cut, referred to as the cleavage site, is generally situated 0-20 bases away from the recognition site. The recognition site is generally about 4-7 bp long. All type IIS restriction enzymes exhibit at least partial asymmetric recognition. Asymmetric recognition means that 5'3' recognition sequences are different for each strand of the nucleic acid. The enzyme activity also shows polarity meaning that the cleavage sites are located on only one side of the recognition site. Thus, there is generally only one double stranded cut corresponding to each recognition site. Cleavage generally produces 1-5 nucleotide single-stranded overhangs, with 5' or 3' termini, although some enzymes produce blunt ends. Either cut is useful in the context of the invention, although in some instances those producing single-stranded overhangs are produced. To date, about 80 type IIS enzymes have been identified. Examples include but are not limited to BstF5 I, BtsC I, BsrD I, Bts I, Alw I, Bcc I, BsmA I, Ear I, Mly I (blunt), Ple I, Bmr I, Bsa I, BsmB I, Fau I, Mnl I, Sap I, Bbs I, BciV I, Hph I, Mbo II, BfuA I, BspCN I, BspM I, SfaN I, Hga I, BseR I, Bbv I, Eci I, Fok I, BceA I, BsmF I, BtgZ I, BpuE I, Bsg I, Mme I, BseG I, Bse3D I, BseM I, AcIW I, Alw26 I, Bst6 I, BstMA I, Eam1104 I, Ksp632 I, Pps I, Sch I (blunt), Bfi I, Bso31 I, BspTN I, Eco31 I, Esp3 I, Smu I, Bfu I, Bpi I, BpuA I, BstV2 I, AsuHP I, Acc36 I, Lwe I, Aar I, BseM H, TspDT I, TspGW I, BseX I, BstV1 I, Eco57 I, Eco57M I, Gsu I, and Bcg I. Such enzymes and information regarding their recognition and cleavage sites are available from commercial suppliers such as New England Biolabs, Inc. (Ipswich, Mass., U.S.A.).

In some embodiments, commercial or engineered restriction enzyme may be used. In some embodiments, Type IIS restriction enzymes can be designed and engineered to produce longer overhang lengths. Designing and engineering restriction enzymes to produce longer single-stranded overhangs can allow for the joining of a larger number of oligonucleotides together to form longer nucleic acid constructs. For example, BsaI, which produces a 4 nucleotide single-stranded overhang, can be engineered to produce a 5, or 6 or longer single-stranded overhang. Increasing the length of the single-stranded overhang produced by such engineered BsaI can increase the theoretical limit of 17 nucleic acids or oligonucleotides that can be joined.

In some embodiments, each of a plurality of nucleic acid fragments designed for nucleic acid assembly may have a Type IIS restriction site at each end. The Type IIS restriction sites may be oriented so that the cleavage sites are internal relative to the recognition sequences. As a result, enzyme digestion exposes an internal sequence (e.g., an overhang within an internal sequence) and removes the recognition sequences from the ends. Accordingly, the same Type IIS sites may be used for both ends of all of the nucleic acid fragments being prepared for assembly and/or may be used for linearizing a suitable vector. However, different Type IIS sites also may be used. Two fragments that are designed to be adjacent in an assembled product each may include an identical overlapping terminal sequence and a flanking Type IIS site that is appropriately located to expose complementary overhangs within the overlapping sequence upon restriction enzyme digestion. Accordingly, a plurality of nucleic acid fragments may be generated with different complementary overhangs. The restriction site at each end of a nucleic acid fragment may be located such that digestion with the appropriate Type IIS enzyme removes the restriction site and exposes a single-stranded region that is complementary to a single-stranded region on a nucleic acid fragment that is designed to be adjacent in the assembled nucleic acid product. In some embodiments, one end of each of the two terminal nucleic acid fragments may be designed to have a single-stranded overhang (e.g., after digestion with an appropriate restriction enzyme) that is complementary to a single-stranded overhang of a linearized vector nucleic acid. Accordingly, the resulting nucleic acid fragments and vector may be transformed directly into a host cell. Alternatively, the nucleic acid fragments and vector may be incubated to promote hybridization and annealing of the complementary sequences prior to transformation in the host cell. It should be appreciated that a vector may be prepared using any one of the techniques described herein or any other suitable technique that produces a single-stranded overhang that would be complementary to an end of one of the terminal nucleic acid fragments.

Enzymatic digestions of DNA with Type II or site-specific restriction enzymes typically generate an overhang of four to six nucleotides. These short cohesive ends may be sufficient for ligating two nucleic acid fragments containing complementary termini. However, when joining multiple nucleic acid fragments together, longer complementary cohesive termini may be preferred to facilitate assembly and to ensure specificity. For example, cohesive ends may be long enough to have sufficiently different sequences to prevent or reduce mispairing between similar cohesive ends. However, their length is preferably not long enough to stabilize mispairs between similar cohesive sequences. In some embodiments, a length of about 9 to about 15 bases may be used. However, any suitable length may be selected for a region that is to be used to generate a cohesive overhang. The importance of specificity may depend on the number of different fragments that are being assembled simultaneously. Also, the appropriate length required to avoid stabilizing mispaired regions may depend on the conditions used for annealing different cohesive ends.

Ligase-Based Assembly

Ligase-based assembly techniques may involve one or more suitable ligase enzymes that can catalyze the covalent linking of adjacent 3' and 5' nucleic acid termini (e.g., a 5' phosphate and a 3' hydroxyl of nucleic acid(s) annealed on a complementary template nucleic acid such that the 3' terminus is immediately adjacent to the 5' terminus). Accordingly, a ligase may catalyze a ligation reaction between the 5' phosphate of a first nucleic acid to the 3' hydroxyl of a second nucleic acid if the first and second nucleic acids are annealed next to each other on a template nucleic acid). A ligase may be obtained from recombinant or natural sources. A ligase may be a heat-stable ligase. In some embodiments, a thermostable ligase from a thermophilic organism may be used. Examples of thermostable DNA ligases include, but are not limited to: Tth DNA ligase (from *Thermus thermophilus*, available from, for example, Eurogentec and GeneCraft); Pfu DNA ligase (a hyperthermophilic ligase from *Pyrococcus furiosus*); Taq ligase (from *Thermus aquaticus*), any other suitable heat-stable ligase, or any combination thereof. In some embodiments, one or more lower temperature ligases may be used (e.g., T4 DNA ligase). A lower temperature ligase may be useful for shorter overhangs (e.g., about 3, about 4, about 5, or about 6 base overhangs) that may not be stable at higher temperatures.

In some embodiments, ligase may be designed and engineered to have a greater degree of specificity so as to minimize unwanted ligation products formed. In some embodiments, ligase may be used in conjunction with proteins or may be fused with proteins capable of facilitating the interaction of the ligase with nucleic acid molecules and/or of increasing specificity of ligation.

Non-enzymatic techniques can be used to ligate nucleic acids. For example, a 5'-end (e.g., the 5' phosphate group) and a 3'-end (e.g., the 3' hydroxyl) of one or more nucleic acids may be covalently linked together without using enzymes (e.g., without using a ligase). In some embodiments, non-enzymatic techniques may offer certain advantages over enzyme-based ligations. For example, non-enzymatic techniques may have a high tolerance of non-natural nucleotide analogues in nucleic acid substrates, may be used to ligate short nucleic acid substrates, may be used to ligate RNA substrates, and/or may be cheaper and/or more suited to certain automated (e.g., high throughput) applications. Accordingly, a chemical ligation may be used to form a covalent linkage between a 5' terminus of a first nucleic acid end and a 3' terminus of a second nucleic acid end, wherein the first and second nucleic acid ends may be ends of a single nucleic acid or ends of separate nucleic acids. In one aspect, chemical ligation may involve at least one nucleic acid substrate having a modified end (e.g., a modified 5' and/or 3' terminus) including one or more chemically reactive moieties that facilitate or promote linkage formation. In some embodiments, chemical ligation occurs when one or more nucleic acid termini are brought together in close proximity (e.g., when the termini are brought together due to annealing between complementary nucleic acid sequences). Accordingly, annealing between complementary 3' or 5' overhangs (e.g., overhangs generated by restriction enzyme cleavage of a double-stranded nucleic acid) or between any combination of complementary nucleic acids that results in a 3' terminus being brought into close proximity with a 5' terminus (e.g., the 3' and 5' termini are adjacent to each other when the nucleic acids are annealed to a complementary template nucleic acid) may promote a template-directed chemical ligation. Examples of chemical reactions may include, but are not limited to, condensation, reduction, and/or photochemical ligation reactions. It should be appreciated that in some embodiments chemical ligation can be used to produce naturally-occurring phosphodiester internucleotide linkages, non-naturally-occurring phosphamide pyrophosphate internucleotide linkages, and/or other non-naturally-occurring internucleotide linkages.

Figure 2:
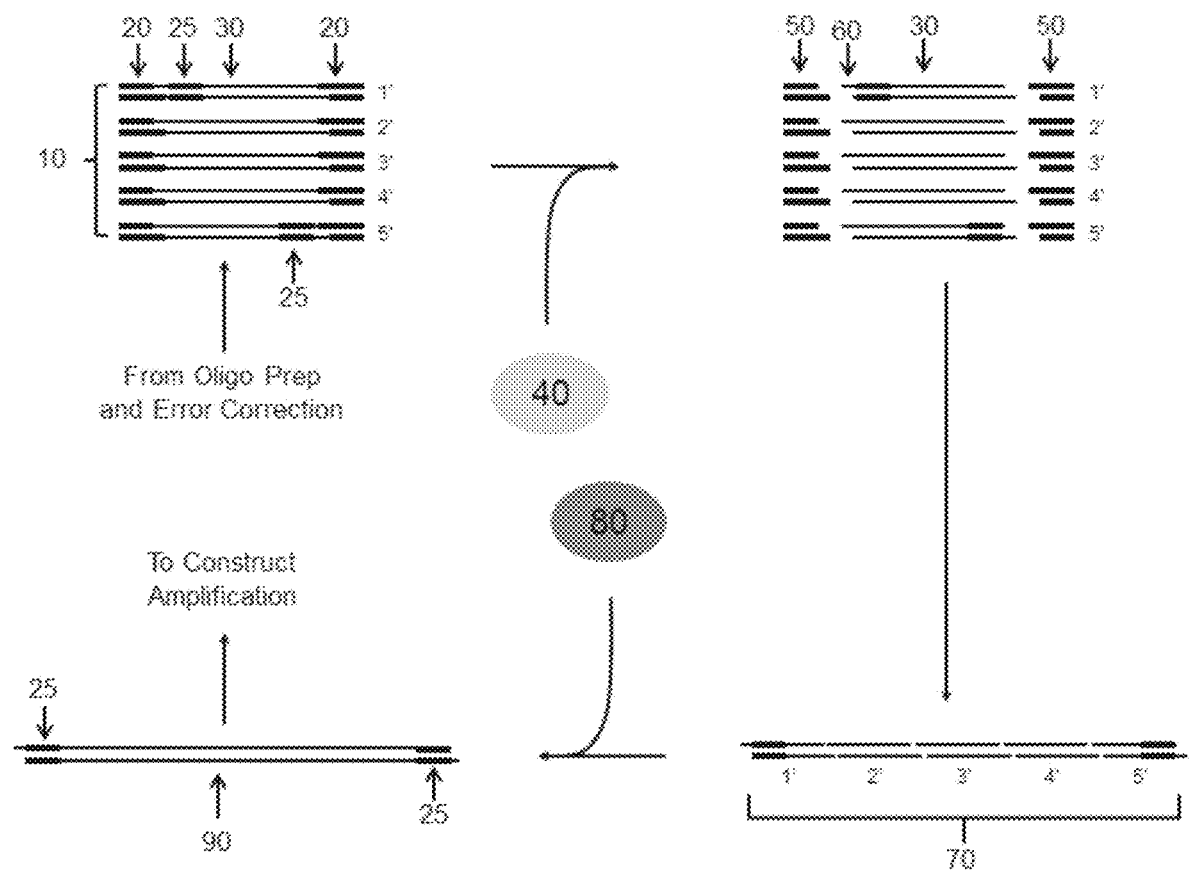
FIG. 2 illustrates a non-limiting example of assembly method of a polynucleotide having a predefined sequence.

Concurrent Enzymatic Removal of Common Oligonucleotide Sequences and Ligation of Processed Oligonucleotides into Longer Constructs FIG. 2 illustrates a method for assembling a nucleic acid in accordance with one embodiment of the invention. In some embodiments, the method comprises concurrent enzymatic removal of common oligonucleotide sequences and ligation of processed oligonucleotide sequences into longer constructs. In some embodiments, the oligonucleotides are amplified by PCR and error corrected as described herein. Amplified oligonucleotides (10), composed of a common priming (amplification) sequence (20) and construct specific payload or internal sequences regions (30) are processed by an appropriate restriction endonuclease (40). In some embodiments, the first and last oligonucleotides contain unique priming sequences (25) for amplification of the target construct. The restriction endonuclease catalyzes the cleavage of the terminal common regions (also referred herein as amplification regions or primer recognition sequences) shared by all of the oligonucleotides (50), leaving internal regions (also referred herein as free payload) with terminal single stranded DNA sequences (60). In some embodiments, the restriction endonuclease is a type IIS restriction endonuclease. These single stranded sequences are designed to instruct the specific interaction of one oligonucleotide with another, allowing the linear arrangement of a number of oligonucleotides into a defined sequence (70). Accordingly, the terminal single stranded DNA sequences can direct the appropriate interaction of oligonucleotides into the correct order, whereby ligase (80) enzyme catalyses the joining of individual oligonucleotides, generating the final target nucleic acid construct (90) or intermediate nucleic acid constructs.

One of skill in the art will appreciate that if the original common sequence is ligated back together (for example (50) using the terminal sequences complementary to (60)), the presence of the restriction endonuclease can ensure that it may be cut again to generate the free end (60). However, because of the choice of restriction endonuclease, a properly ligated junction (for example between 1' and 2') will not be recognized as a restriction site and will not be undone. The reaction should naturally drive toward the desired product (90).

Figure 4:
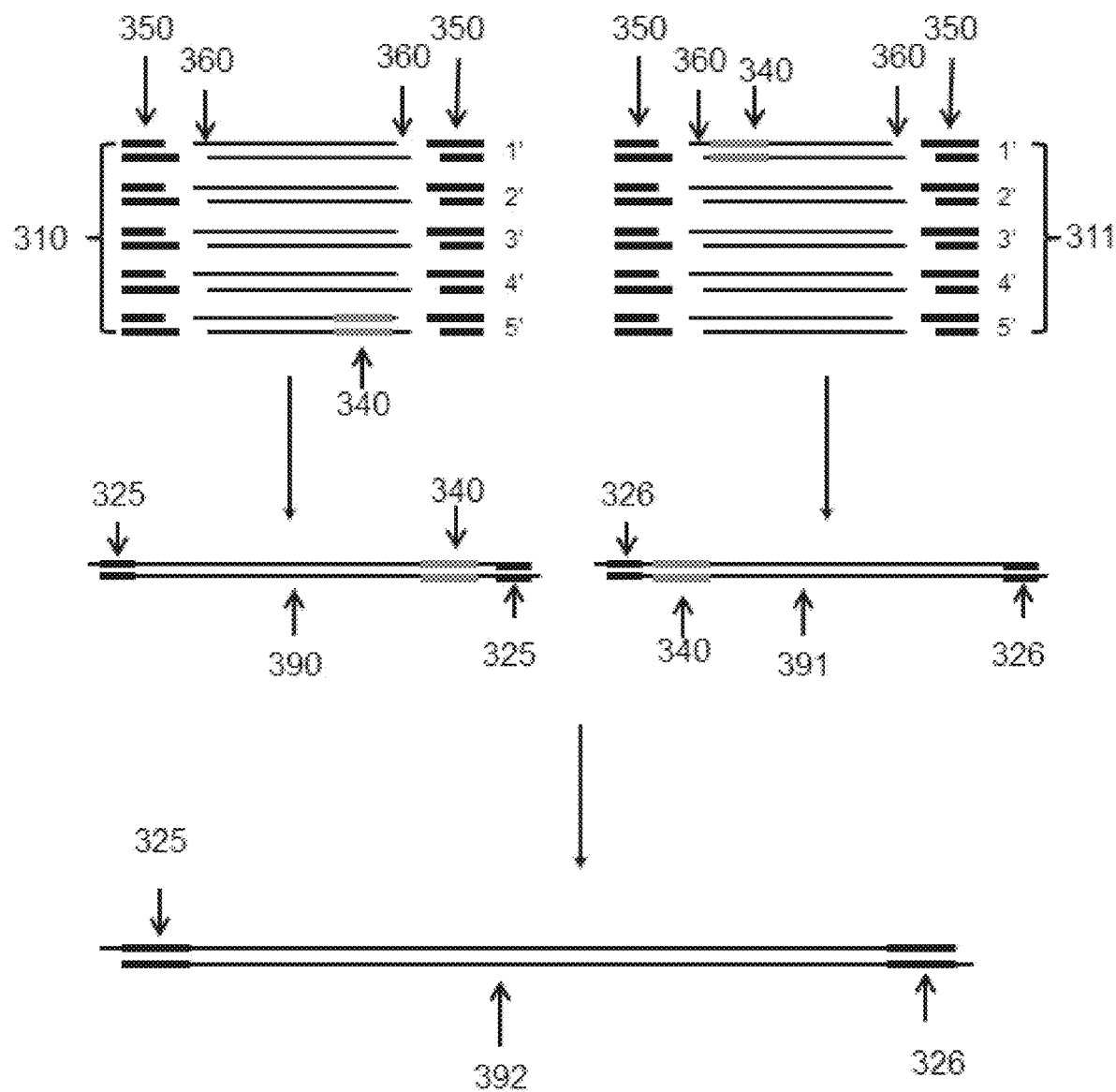
FIG. 4 illustrates a non-limiting example of hierarchical assembly method of a polynucleotide having a predefined sequence.

In some embodiments, a variant of the process recognizes that the restriction site used for common sequence removal can now be part of the gene to be synthesized. This constraint removal allows for recursive (hierarchical) applications of the gene synthesis method to build longer nucleic acid sequences (as illustrated in FIG. 4). In previous methodologies, where removal and ligation were performed as separate steps, this design was disallowed due to the necessity of a purification step in between the removal and the ligation steps, which was based partially on size selection. In such methodologies, pieces cut of the desired target sequence could be lost during the purification, resulting in failure to build the desired target sequence. In some embodiments, using the concurrent removal and ligation step of the invention, those cut sequences would be constantly cut and re-ligated, resulting in the presence of some of the target sequence of interest. The amount of the desired sequence may depend, in some embodiments, on the tuning of the relative activities of the restriction enzyme and the ligase.

As illustrated in FIG. 4, the gene synthesis pieces (390) and (391) can be assembled from oligonucleotide sets (310) and (311). The oligonucleotide sets can be designed with matching restriction endonuclease sites (340) such that the gene synthesis pieces (390) and (391) can be joined using the same concurrent digestion and ligation process (with subsequent amplification). In some embodiments, the second round can have been designed with restriction endonuclease sites (340) using a second restriction enzyme. However, this may be undesirable due to complications of using multiple enzymes in the process. In addition, without the concurrent digestion and ligation, the use of two restrictions enzymes would result in disallowing two restriction enzyme sites from the target sequence, further constraining the genes that can be synthesized.

Still referring to FIG. 4, the nucleic acid fragment (390) can be amplified using primers (325), and the nucleic acid fragment (391) can be amplified using primers (326). The nucleic acid fragment may then be mixed together and processed in a similar fashion to the previous synthesis step to create the combined nucleic acid fragment (392), where the restriction sites (340) act in a similar manner to the sites (350) in the previous round. The combined target sequence (392) can be amplified using the 5' primer from (325) and the 3' primer from (326).

In some embodiments, hierarchical assembly strategies may be used in accordance with the methods disclosed herein. One of skill the art will appreciate that the present method can be scalable to multiple nucleic acid fragments, such that the number of nucleic acid fragments in the subsequent round can be similar to the number of nucleic acid fragments in the first round. The hierarchical assembly method can be geometric, allowing very large targets to be constructed in a relatively few number of rounds. For example, a target sequence of 1000 bases (1 kbp) can be constructed from one of the pools (310) or (311). A second round of 10 nucleic acid fragments similar to (390) or (391) would result in a 10 kbp base target nucleic acid sequence. A third round, using the 10 kbp nucleic acid sequences, would result in a 100 kbp target nucleic acid sequence, derived from the original 100 source pools.

In some embodiments, a plurality of assembly reactions may be conducted in separate pools. Assembly constructs from the assembly reactions may then be mixed to together to form even longer nucleic acid sequences. In some embodiments, hierarchical assembly may be carried out using restriction endonucleases to form cohesive ends that may be joined together in a desired order. The construction oligonucleotides may be designed and synthesized to contain recognition and cleavage sites for one or more restriction endonucleases at sites that would facilitate joining in a specified order. In some embodiments, one or more Type IIS endonuclease recognition sites may be incorporated into the termini of the construction oligonucleotides to permit cleavage by a Type IIS restriction endonuclease. The order of joining can be determined by hybridization of the complementary cohesive ends.

In some embodiments, the first pool of oligonucleotides comprises a 3' end oligonucleotide designed to have an additional restriction enzyme recognition site at its 3' end and the second pool of oligonucleotides comprises a 5' end oligonucleotide designed to have an additional restriction enzyme recognition site at its 5' end. In some embodiments, the restriction enzymes are the same. After assembly of the oligonucleotides in each pool, the two subassembly constructs can be subjected to the restriction endonuclease and to ligase in accordance with the methods disclosed herein.

One of skill in the art would understand that the available assembly space of the synthesis is drastically (geometrically) improved by the aspects of the invention. Previously, to generate a construct of double the sequence size (2n), double the numbers of oligonucleotides were required. For example, to generate a construct (390), double the numbers of oligonucleotides (310) were required, and thus double the numbers of compatible single stranded ends (360) were required. Using the method illustrated in FIG. 4, the junctions for (310) and (311) only have to be compatible with junction (340), thus enabling the assembly of nucleic acids of double the size with only one extra junction used. Therefore, if oligonucleotides (310) and (311) have interfering or incompatible ends, they may still be joined by the process disclosed herein (digestion (340) and ligation) to make target nucleic acid (392), whereas joining would not be possible by solely mixing the oligonucleotide pools (310) and (311) together.

Figure 3:
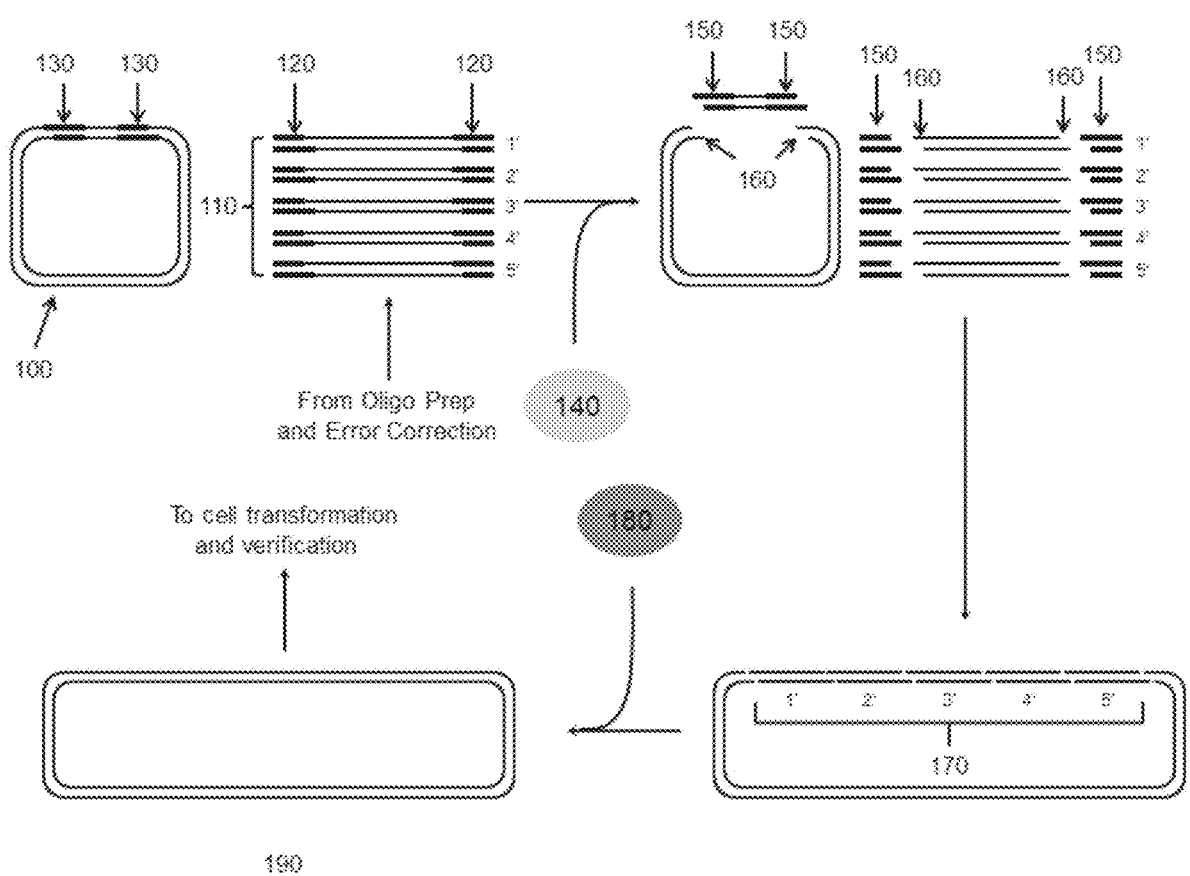
FIG. 3 illustrates a non-limiting example of assembly method of a polynucleotide having a predefined sequence into a vector.

A variant of the concurrent processing of oligonucleotides and assembly into target constructs and simultaneous entry into a plasmid is illustrated in FIG. 3. Details of the plasmid, pG9-1 (SEQ ID NO. 1) are shown in FIG. 5. The plasmid contains restriction endonuclease recognition sites (underlined text, FIG. 5) that allows a restriction endonuclease (in this case BsaI) to cut the plasmid at two positions, leaving defined single stranded sequences (FIG. 5—reverse text). Referring to FIG. 3, plasmid (100) (e.g. pG9-1) is introduced into a pool comprising a mixture of oligonucleotides (110) that have been previously amplified and error corrected as described herein. In some embodiments, these oligonucleotide sequences (110) can have common sequences (120) that are recognized by a specific restriction endonuclease (140). In some embodiments, the plasmid (130) can have sequences recognized by the same restriction endonuclease (140). Action of restriction endonuclease (140) upon these sequences results in the removal of the common sequences from the oligonucleotides ((310), (311)) and plasmid (150), exposing single stranded DNA sequences (160). In some embodiments, the restriction enzyme can be a type IS restriction enzyme. In some embodiments, the single stranded sequences are designed to instruct the specific interaction of one oligonucleotide with another, allowing the arrangement of a number of oligonucleotides into a defined sequence and entry of this ordered sequence of oligonucleotides (170) into the plasmid (100). In some embodiments, ligase (180) enzyme catalyzes the covalent joining of the individual oligonucleotides. The final product is the plasmid (e.g. pG9-1) containing the specified construct derived from joining the oligonucleotides (190). This plasmid (190) may then transformed into a bacteria and sequenced-verified.

Figure 6:
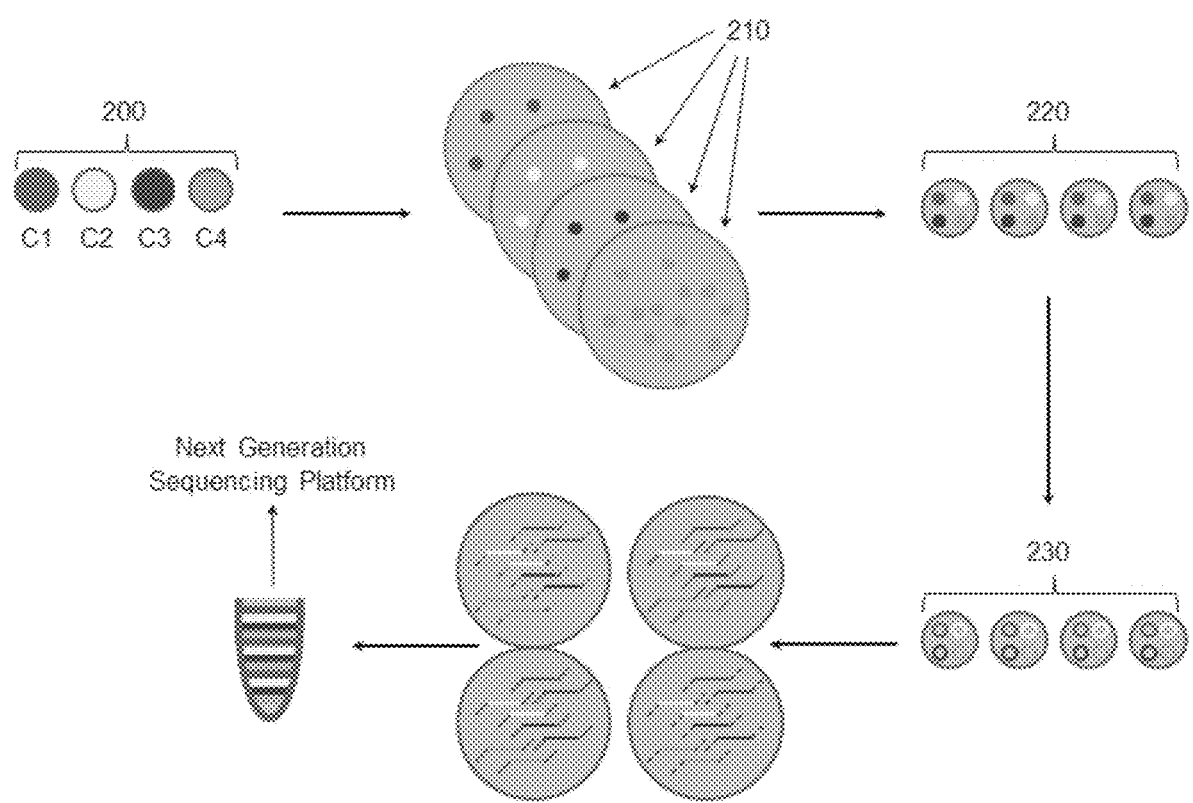
FIG. 6 illustrates non-limiting exemplary method of sequence verification.

Aspects of the invention relate to the sequence verification of the constructs assembled according to the methods of the invention. Sequence verification of constructs is illustrated in FIG. 6. In this process, a number of constructs (200, C1 to C4) can be generated as shown in FIG. 3 and transformed into bacteria. Bacterial transformants containing plasmid DNA can be selected on solid growth plates (210) using an appropriate antibiotic resistance for selection. After growth, single colonies are picked and pooled, one from each construct plate (220), generating pools of constructs, each pool containing one copy of each construct. In some embodiments, the number of pools can be dependent upon the number of individual constructs that are to be sequenced in order to identify constructs with perfect sequence. As illustrated in FIG. 6, four pools of the four constructs are generated, allowing analysis of four members of each construct. Plasmid DNA can then be prepared from the pooled material (230). Each pool of plasmid DNA molecules can then prepared for sequencing. This preparation may use one of a variety of methods that cause breakage of DNA into smaller fragments and the attachment of common sequences required for sequencing using, for example, next generation high throughput sequencing. Short pieces of DNA, unique to each of the four pools generated, are contained within these common sequences. These unique pieces of DNA can allow identification of which pool each sequenced construct is derived from. Constructs with the correct sequence can then be recovered by going back to the initial bacterial growth plate and re-growing the corresponding colony containing the plasmid with the wanted construct.

Vectors and Host Cells

Any suitable vector may be used, as the invention is not so limited. For example, a vector may be a plasmid, a bacterial vector, a viral vector, a phage vector, an insect vector, a yeast vector, a mammalian vector, a BAC, a YAC, or any other suitable vector. In some embodiments, a vector may be a vector that replicates in only one type of organism (e.g., bacterial, yeast, insect, mammalian, etc.) or in only one species of organism. Some vectors may have a broad host range. Some vectors may have different functional sequences (e.g., origins or replication, selectable markers, etc.) that are functional in different organisms. These may be used to shuttle the vector (and any nucleic acid fragment(s) that are cloned into the vector) between two different types of organism (e.g., between bacteria and mammals, yeast and mammals, etc.). In some embodiments, the type of vector that is used may be determined by the type of host cell that is chosen.

It should be appreciated that a vector may encode a detectable marker such as a selectable marker (e.g., antibiotic resistance, etc.) so that transformed cells can be selectively grown and the vector can be isolated and any insert can be characterized to determine whether it contains the desired assembled nucleic acid. The insert may be characterized using any suitable technique (e.g., size analysis, restriction fragment analysis, sequencing, etc.). In some embodiments, the presence of a correctly assembly nucleic acid in a vector may be assayed by determining whether a function predicted to be encoded by the correctly assembled nucleic acid is expressed in the host cell.

In some embodiments, host cells that harbor a vector containing a nucleic acid insert may be selected for or enriched by using one or more additional detectable or selectable markers that are only functional if a correct (e.g., designed) terminal nucleic acid fragments is cloned into the vector.

Accordingly, a host cell should have an appropriate phenotype to allow selection for one or more drug resistance markers encoded on a vector (or to allow detection of one or more detectable markers encoded on a vector). However, any suitable host cell type may be used (e.g., prokaryotic, eukaryotic, bacterial, yeast, insect, mammalian, etc.). For example, host cells may be bacterial cells (e.g., *Escherichia coli, Bacillus subtilis, Mycobacterium* spp., *M. tuberculosis*, or other suitable bacterial cells), yeast cells (for example, *Saccharomyces* spp., *Picchia* spp., *Candida* spp., or other suitable yeast species, e.g., *S. cerevisiae, C. albicans, S. pombe*, etc.), *Xenopus* cells, mouse cells, monkey cells, human cells, insect cells (e.g., SF9 cells and *Drosophila* cells), worm cells (e.g., *Caenorhabditis* spp.), plant cells, or other suitable cells, including for example, transgenic or other recombinant cell lines. In addition, a number of heterologous cell lines may be used, such as Chinese Hamster Ovary cells (CHO).

Applications

Aspects of the invention may be useful for a range of applications involving the production and/or use of synthetic nucleic acids. As described herein, the invention provides methods for assembling synthetic nucleic acids with increased efficiency. The resulting assembled nucleic acids may be amplified in vitro (e.g., using PCR, LCR, or any suitable amplification technique), amplified in vivo (e.g., via cloning into a suitable vector), isolated and/or purified. An assembled nucleic acid (alone or cloned into a vector) may be transformed into a host cell (e.g., a prokaryotic, eukaryotic, insect, mammalian, or other host cell). In some embodiments, the host cell may be used to propagate the nucleic acid. In certain embodiments, the nucleic acid may be integrated into the genome of the host cell. In some embodiments, the nucleic acid may replace a corresponding nucleic acid region on the genome of the cell (e.g., via homologous recombination). Accordingly, nucleic acids may be used to produce recombinant organisms. In some embodiments, a target nucleic acid may be an entire genome or large fragments of a genome that are used to replace all or part of the genome of a host organism. Recombinant organisms also may be used for a variety of research, industrial, agricultural, and/or medical applications.

Many of the techniques described herein can be used together, applying combinations of one or more extension-based and/or ligation-based assembly techniques at one or more points to produce long nucleic acid molecules. For example, concerted assembly may be used to assemble oligonucleotide duplexes and nucleic acid fragments of less than 100 to more than 10,000 base pairs in length (e.g., 100 mers to 500 mers, 500 mers to 1,000 mers, 1,000 mers to 5,000 mers, 5,000 mers to 10,000 mers, 25,000 mers, 50,000 mers, 75,000 mers, 100,000 mers, etc.). In an exemplary embodiment, methods described herein may be used during the assembly of an entire genome (or a large fragment thereof, e.g., about 10%, 20%, 30%, 40%, 50%, 60%, 70%, 80%, 90%, or more) of an organism (e.g., of a viral, bacterial, yeast, or other prokaryotic or eukaryotic organism), optionally incorporating specific modifications into the sequence at one or more desired locations.

Nucleic acid molecules generated using methods of the invention can be incorporated into a vector. The vector may be a cloning vector or an expression vector. A vector may comprise an origin of replication and one or more selectable markers (e.g., antibiotic resistant markers, auxotrophic markers, etc.). In some embodiments, the vector may be a viral vector. A viral vector may comprise nucleic acid sequences capable of infecting target cells. Similarly; in some embodiments, a prokaryotic expression vector operably linked to an appropriate promoter system can be used to transform target cells. In other embodiments, a eukaryotic vector operably linked to an appropriate promoter system can be used to transfect target cells or tissues.

Transcription and/or translation of the constructs described herein may be carried out in vitro (i.e., using cell-free systems) or in vivo (i.e., expressed in cells). In some embodiments, cell lysates may be prepared. In certain embodiments, expressed RNAs or polypeptides may be isolated or purified.

Aspects of the methods and devices provided herein may include automating one or more acts described herein. In some embodiments, one or more steps of an amplification and/or assembly reaction may be automated using one or more automated sample handling devices (e.g., one or more automated liquid or fluid handling devices). Automated devices and procedures may be used to deliver reaction reagents, including one or more of the following: starting nucleic acids, buffers, enzymes (e.g., one or more ligases and/or polymerases), nucleotides, salts, and any other suitable agents such as stabilizing agents. Automated devices and procedures also may be used to control the reaction conditions. For example, an automated thermal cycler may be used to control reaction temperatures and any temperature cycles that may be used. In some embodiments, a scanning laser may be automated to provide one or more reaction temperatures or temperature cycles suitable for incubating polynucleotides. Similarly, subsequent analysis of assembled polynucleotide products may be automated. For example, sequencing may be automated using a sequencing device and automated sequencing protocols. Additional steps (e.g., amplification, cloning, etc.) also may be automated using one or more appropriate devices and related protocols. It should be appreciated that one or more of the device or device components described herein may be combined in a system (e.g., a robotic system) or in a micro-environment (e.g., a micro-fluidic reaction chamber). Assembly reaction mixtures (e.g., liquid reaction samples) may be transferred from one component of the system to another using automated devices and procedures (e.g., robotic manipulation and/or transfer of samples and/or sample containers, including automated pipetting devices, micro-systems, etc.). The system and any components thereof may be controlled by a control system.

Accordingly, method steps and/or aspects of the devices provided herein may be automated using, for example, a computer system (e.g., a computer controlled system). A computer system on which aspects of the technology provided herein can be implemented may include a computer for any type of processing (e.g., sequence analysis and/or automated device control as described herein). However, it should be appreciated that certain processing steps may be provided by one or more of the automated devices that are part of the assembly system. In some embodiments, a computer system may include two or more computers. For example, one computer may be coupled, via a network, to a second computer. One computer may perform sequence analysis. The second computer may control one or more of the automated synthesis and assembly devices in the system. In other aspects, additional computers may be included in the network to control one or more of the analysis or processing acts. Each computer may include a memory and processor. The computers can take any form, as the aspects of the technology provided herein are not limited to being implemented on any particular computer platform. Similarly, the network can take any form, including a private network or a public network (e.g., the Internet). Display devices can be associated with one or more of the devices and computers. Alternatively, or in addition, a display device may be located at a remote site and connected for displaying the output of an analysis in accordance with the technology provided herein. Connections between the different components of the system may be via wire, optical fiber, wireless transmission, satellite transmission, any other suitable transmission, or any combination of two or more of the above.

Each of the different aspects, embodiments, or acts of the technology provided herein can be independently automated and implemented in any of numerous ways. For example, each aspect, embodiment, or act can be independently implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as one or more controllers that control the above-discussed functions. The one or more controllers can be implemented in numerous ways, such as with dedicated hardware, or with general purpose hardware (e.g., one or more processors) that is programmed using microcode or software to perform the functions recited above.

In this respect, it should be appreciated that one implementation of the embodiments of the technology provided herein comprises at least one computer-readable medium (e.g., a computer memory, a floppy disk, a compact disk, a tape, etc.) encoded with a computer program (i.e., a plurality of instructions), which, when executed on a processor, performs one or more of the above-discussed functions of the technology provided herein. The computer-readable medium can be transportable such that the program stored thereon can be loaded onto any computer system resource to implement one or more functions of the technology provided herein. In addition, it should be appreciated that the reference to a computer program which, when executed, performs the above-discussed functions, is not limited to an application program running on a host computer. Rather, the term computer program is used herein in a generic sense to reference any type of computer code (e.g., software or microcode) that can be employed to program a processor to implement the above-discussed aspects of the technology provided herein.

It should be appreciated that in accordance with several embodiments of the technology provided herein wherein processes are stored in a computer readable medium, the computer implemented processes may, during the course of their execution, receive input manually (e.g., from a user).

Accordingly, overall system-level control of the assembly devices or components described herein may be performed by a system controller which may provide control signals to the associated nucleic acid synthesizers, liquid handling devices, thermal cyclers, sequencing devices, associated robotic components, as well as other suitable systems for performing the desired input/output or other control functions. Thus, the system controller along with any device controllers together form a controller that controls the operation of a nucleic acid assembly system. The controller may include a general purpose data processing system, which can be a general purpose computer, or network of general purpose computers, and other associated devices, including communications devices, modems, and/or other circuitry or components to perform the desired input/output or other functions. The controller can also be implemented, at least in part, as a single special purpose integrated circuit (e.g., ASIC) or an array of ASICs, each having a main or central processor section for overall, system-level control, and separate sections dedicated to performing various different specific computations, functions and other processes under the control of the central processor section. The controller can also be implemented using a plurality of separate dedicated programmable integrated or other electronic circuits or devices, e.g., hard wired electronic or logic circuits such as discrete element circuits or programmable logic devices. The controller can also include any other components or devices, such as user input/output devices (monitors, displays, printers, a keyboard, a user pointing device, touch screen, or other user interface, etc.), data storage devices, drive motors, linkages, valve controllers, robotic devices, vacuum and other pumps, pressure sensors, detectors, power supplies, pulse sources, communication devices or other electronic circuitry or components, and so on. The controller also may control operation of other portions of a system, such as automated client order processing, quality control, packaging, shipping, billing, etc., to perform other suitable functions known in the art but not described in detail herein.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

EQUIVALENTS

The present invention provides among other things novel methods and devices for high-fidelity gene assembly. While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

INCORPORATION BY REFERENCE

Reference is made to U.S. application Ser. No. 13/986,368, filed Apr. 24, 2013, U.S. application Ser. No. 13/524,164, filed Jun. 15, 2012, and PCT publication PCT/US2009/055267. All publications, patents, patent applications, and sequence database entries mentioned herein are hereby incorporated by reference in their entirety as if each individual publication or patent was specifically and individually indicated to be incorporated by reference.

What is claimed is:

1. A method of producing a nucleic acid having a predefined sequence, the method comprising:
   (a) providing a first pool of double-stranded oligonucleotides, wherein the double-stranded oligonucleotides comprise:
      (i) internal sequences identical to different portions of a first target nucleic acid, wherein the internal sequences comprise an overlapping region with another double-stranded oligonucleotide in the first pool; and
      (ii) 5' flanking sequences and/or 3' flanking sequences, each of the flanking sequences comprising a common primer recognition site and a first restriction enzyme recognition site, the first restriction enzyme recognition site being oriented so that digestion with a first restriction enzyme that recognizes the first restriction enzyme recognition site will remove the flanking sequences and expose the internal sequence; and
   (b) exposing the first pool of double-stranded oligonucleotides to a ligase and the first restriction enzyme under conditions suitable to promote concurrent restriction enzyme digestion and ligation, thereby generating the first target nucleic acid;
   wherein the first target nucleic acid comprises:
      (i) an internal sequence identical to a portion of a final target nucleic acid; and
      (ii) a 5' flanking sequence and/or a 3' flanking sequence, each of the flanking sequences comprising a second restriction enzyme recognition site, wherein the first restriction enzyme recognition site and the second restriction enzyme recognition site have different sequences.

2. The method of claim 1, wherein the first target nucleic acid is both strands of a double-stranded molecule.

3. The method of claim 1, wherein the first target nucleic acid does not comprise a substrate of the first restriction enzyme of (b).

4. The method of claim 1, wherein the first restriction enzyme recognition site is a Type IIs restriction enzyme recognition site, and wherein the first restriction enzyme is a Type IIs restriction enzyme.

5. The method of claim 1, wherein the double-stranded oligonucleotides in the first pool are produced by amplifying a plurality of single-stranded oligonucleotides, each single-stranded oligonucleotide corresponding to one strand of a double-stranded oligonucleotide in the first pool, wherein amplification is performed using the common primer recognition sites of the single-stranded oligonucleotides.

6. The method of claim 5, further comprising subjecting the amplified oligonucleotides to mismatch binding or error removal.

7. The method of claim 6, wherein the amplified oligonucleotides are contacted with a mismatch binding agent, and wherein the mismatch binding agent is MutS.

8. The method of claim 1, further comprising, after step (b), amplifying the first target nucleic acid.

9. The method of claim 1, further comprising confirming the sequence accuracy of and isolating the first target nucleic acid.

10. The method of claim 1, further comprising:
    (c) providing a mixture comprising the first target nucleic acid and a second target nucleic acid, wherein the second target nucleic acid comprises:
       (i) an internal sequence that differs from the internal sequence of the first target nucleic acid and is identical to a portion of the final target nucleic acid;
       (ii) a 5' flanking sequence and/or a 3' flanking sequence, each of the flanking sequences comprising the second restriction enzyme recognition site; and
    (d) exposing the mixture to a ligase and a second restriction enzyme that recognizes the second restriction enzyme recognition site, thereby generating the final target nucleic acid comprising the internal sequence of the first target nucleic acid and the internal sequence of the second target nucleic acid.

11. The method of claim 10, wherein the first and the second target nucleic acids are subject in (d) to conditions suitable to promote concurrent digestion and ligation.

12. The method of claim 10, wherein the final target nucleic acid does not comprise a substrate of the second restriction enzyme of (d).

13. The method of claim 10, further comprising, prior to step (d), amplifying the first target nucleic acid and the second target nucleic acid.

14. The method of claim 10, wherein the second target nucleic acid is produced by a method comprising:
  (a) providing a second pool of double-stranded oligonucleotides, wherein the double-stranded oligonucleotides comprise:
    (i) internal sequences identical to different portions of a second target nucleic acid, wherein the internal sequences comprise an overlapping region with another oligonucleotide in the second pool; and
    (ii) 5' flanking sequences and/or 3' flanking sequences, each of the flanking sequences comprising a common primer recognition site and a third restriction enzyme recognition site, the third restriction enzyme recognition site being oriented so that digestion with a third restriction enzyme that recognizes the third restriction enzyme recognition site will remove the flanking sequences and expose the internal sequence; and
  (b) exposing the second pool of double-stranded oligonucleotides to a ligase and the third restriction enzyme under conditions suitable to promote concurrent restriction enzyme digestion and ligation, thereby generating the second target nucleic acid.

15. The method of claim 14, wherein the double-stranded oligonucleotides in the second pool are produced by amplifying a plurality of single-stranded oligonucleotides, each single-stranded oligonucleotide corresponding to one strand of a double-stranded oligonucleotide in the second pool, wherein amplification is performed using the common primer recognition sites of the single-stranded oligonucleotides, and
  wherein the method further comprises subjecting the amplified oligonucleotides to error removal, wherein the amplified oligonucleotides are contacted with a mismatch binding agent, and wherein the mismatch binding agent is MutS.

16. The method of claim 14, wherein the 5' flanking sequences and 3' flanking sequences of the second pool of double-stranded oligonucleotides have the same restriction enzyme recognition site sequences.

17. The method of claim 14, wherein the 5' flanking sequences and 3' flanking sequences of the second pool of double-stranded oligonucleotides have different restriction endonuclease recognition site sequences.

18. The method of claim 14, wherein the third restriction enzyme recognition site and the second restriction enzyme recognition site have the same sequence.

19. The method of claim 14, wherein the third restriction enzyme recognition site and the second restriction enzyme recognition site have different sequences.

20. The method of claim 14, wherein the third restriction enzyme and the second restriction enzyme are the same.

21. The method of claim 14, wherein the third restriction enzyme and the second restriction enzyme are different.

22. The method of claim 14, wherein the third restriction enzyme recognition site is a type IIs restriction enzyme recognition site, and wherein the third restriction enzyme is a type IIs restriction enzyme.

23. The method of claim 10, further comprising, after step (d), confirming the sequence accuracy of the final target nucleic acid by sequencing and/or isolating the final target nucleic acid.

24. The method of claim 10, wherein the second restriction enzyme recognition site is a Type IIs restriction enzyme recognition site, and wherein the second restriction enzyme is a Type IIs restriction enzyme.

25. The method of claim 1, wherein the 5' flanking sequences and 3' flanking sequences of the first pool of double-stranded oligonucleotides have the same restriction enzyme recognition site sequences.

26. The method of claim 1, wherein the 5' flanking sequences and 3' flanking sequences of the first pool of double-stranded oligonucleotides have different restriction enzyme recognition site sequences.

* * * * *